United States Patent
Adams et al.

(10) Patent No.: US 12,331,042 B2
(45) Date of Patent: Jun. 17, 2025

(54) COMPOUNDS SUITABLE FOR THE TREATMENT AND PROPHYLAXIS OF MUSCLE WASTING AND OTHER CONDITIONS

(71) Applicants: Volker Adams, Leipzig (DE); Siegfried Labeit, Neckargemünd (DE)

(72) Inventors: Volker Adams, Leipzig (DE); Siegfried Labeit, Neckargemünd (DE)

(*) Notice: Subject to any disclaimer, the term of this patent is extended or adjusted under 35 U.S.C. 154(b) by 702 days.

(21) Appl. No.: 17/634,174

(22) PCT Filed: Aug. 14, 2020

(86) PCT No.: PCT/EP2020/072911
§ 371 (c)(1),
(2) Date: Feb. 9, 2022

(87) PCT Pub. No.: WO2021/032643
PCT Pub. Date: Feb. 25, 2021

(65) Prior Publication Data
US 2022/0324852 A1    Oct. 13, 2022

(30) Foreign Application Priority Data
Aug. 16, 2019 (EP) .................................. 19192107

(51) Int. Cl.
| | | |
|---|---|---|
| C07D 407/12 | (2006.01) | |
| A61P 3/10 | (2006.01) | |
| A61P 9/04 | (2006.01) | |
| A61P 21/00 | (2006.01) | |
| C07D 311/18 | (2006.01) | |
| C07D 405/12 | (2006.01) | |
| C07D 411/12 | (2006.01) | |

(52) U.S. Cl.
CPC .............. C07D 407/12 (2013.01); A61P 3/10 (2018.01); A61P 9/04 (2018.01); A61P 21/00 (2018.01); C07D 311/18 (2013.01); C07D 405/12 (2013.01); C07D 411/12 (2013.01)

(58) Field of Classification Search
CPC .. C07D 407/12; C07D 311/18; C07D 405/12; C07D 411/12; A61P 21/00; A61P 3/10; A61P 9/04
USPC ....................................................... 514/337
See application file for complete search history.

(56) References Cited

FOREIGN PATENT DOCUMENTS

WO       2015010107 A1    1/2015

OTHER PUBLICATIONS

Adams, V, et al., "Induction of MuRF1 is Essential for TNF-α-Induced Loss of Muscle Function in Mice", J Mol Biol 384, 48-59 (2008).
Castillero, E, et al., "Suppression of atrogin-1 and MuRF1 prevents dexamethasone-induced atrophy of cultured myotubes", Metabolism 62, 1495-1502 (2013).
De Man, F, et al., "Diaphragm Muscle Fiber Weakness in Pulmonary Hypertension", Am J Respir Crit Care Med 183, 1411-1418 (2011).
Eddins, M, et al., "Targeting the Ubiquitin E3 Ligase MuRF1 to Inhibit Muscle Atrophy", Cell Biochem Biophys 60, 113-118 (2011).
Hooijman, P, et al., "Diaphragm Muscle Fiber Weakness and Ubiquitin-Proteasome Activation in Critically Ill Patients", American Journal of Respiratory and Critical Care Medicine 191 (10), 1126-1138 (2015).
Li, F, et al., "Nebulin deficiency in adult muscle causes sarcomere defects and muscle-type-dependent changes in trophicity: novel insights in nemaline myopathy", Human Molecular Genetics 24 (18), 5219-5233 (2015).
Patent Cooperation Treaty, International Search Report and Written Opinion for PCT/EP2020/072911, 9 pages, dated Nov. 13, 2020.

*Primary Examiner* — Kristin A Vajda
(74) *Attorney, Agent, or Firm* — Viksnins Harris Padys Malen LLP

(57) ABSTRACT

The present invention relates to a compound of the general formula I and the pharmaceutically acceptable salts thereof; where the variables are as defined in the claims and the description. The invention also relates to the compounds of formula I for use in the treatment or prophylaxis of muscle wasting conditions, of skeletal or cardial muscle atrophy, of conditions, in particular of myopathies, which are associated with an increased Muscle RING Finger 1 (MuRF1) expression and of other conditions; to the compounds of formula I for use as a medicament; to a pharmaceutical composition comprising at least one compound of formula I and to a method for treating said conditions.

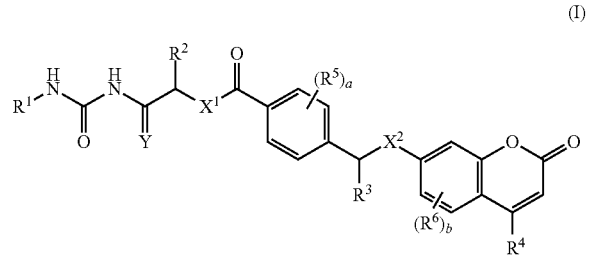

Figure 1:
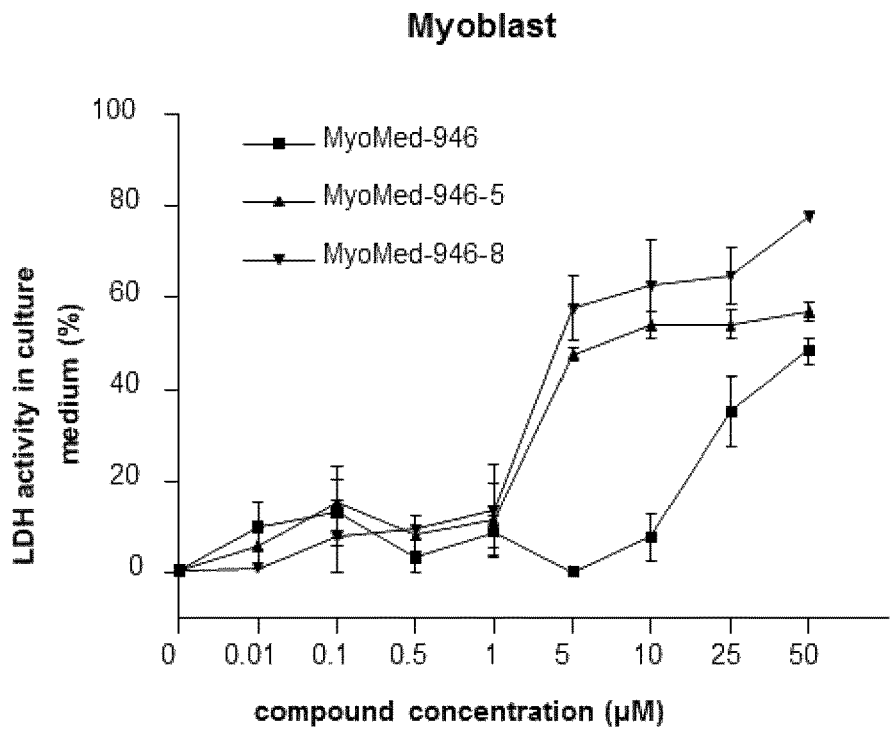

22 Claims, 36 Drawing Sheets
Specification includes a Sequence Listing.

MuRF1

Nox 2

Nitrotyrosine

COMPOUNDS SUITABLE FOR THE TREATMENT AND PROPHYLAXIS OF MUSCLE WASTING AND OTHER CONDITIONS

CROSS-REFERENCE TO RELATED APPLICATION

This patent application claims the benefit of priority of European Application No. 19192107.1, filed Aug. 16, 2019.

BACKGROUND OF THE INVENTION

The present invention relates to novel substituted 4-[2-oxo-chromen-7-yl)heteromethyl]benzoic acid compounds, in particular to the compounds of the general formula I as described herein. The compounds possess valuable therapeutic properties and are suitable for treating and for the prophylaxis of muscle wasting conditions as well as for treating or preventing myopathies, especially for such which are associated with an increased Muscle RING Finger 1 (MuRF1) expression.

Muscle wasting and muscle weakness is a debilitating complication observed under a variety of clinical conditions, including cardiac cachexia, myocardial infarction, hypertension, cancer, cancer treatment with certain drugs, diabetes, renal diseases and renal failure, genetic muscle atrophy and severe infections, but also under several physical conditions which are not linked to a specific disease, such as immobilization, long term mechanical ventilation, prolonged weightlessness or old age. Muscle wasting is characterized by the loss of muscle mass, which occurs in both limb and respiratory muscles. Muscle wasting typically leads to an exacerbation of the symptoms and prognosis and prolongs convalescence.

The underlying mechanism of muscle wasting is not yet fully understood. It is known that muscle wasting includes activation of so-called atrogins, which enhance the degradation of muscle proteins via the autophagosome and ubiquitin proteasome system (UPS).

Unfortunately, there are only few reliable strategies known that block the loss of muscle proteins initiated by above mentioned clinical conditions, e.g. exercise training. These known strategies generally aim to down-regulate or inactivate the expression of atrogins and/or to inhibit their ubiquitylation activity.

WO2015/010107 A1 for example describes the use of small molecules to reduce muscle weakness and/or muscle wasting and/or cachexia by inhibiting the inflammatory cytokine-induced (IL-6-induced) tyrosine phosphorylation of the Signal Transducer and Activator of Transcription 3 (Stat 3). The inhibition of Stat 3 phosphorylation prevents the increased expression of myostatin, which is known to block muscle-growth by up-regulating the expression of specific atrogins.

Another promising strategy to block the loss of muscle proteins is to inhibit the function of Muscle RING Finger 1 (MuRF1). MuRF1 is a muscle-specific ubiquitin E3 ligase, which is believed to provide a key step in the transfer of multi-ubiquitinated muscle proteins to the ubiquitin proteasome system for degradation. Its expression is intimately associated with muscle wasting in numerous clinical conditions, while its gene inactivation confers partial resistance to muscle wasting conditions. Numerous studies over the last 15 years have shown that many muscle related diseases, i.e. myopathies, such as for example critical illness myopathy, nemaline myopathy, chronic inflammatory myopathy, myopathy from diabetes or pulmonary hypertension, which results in muscular weakness, can be linked to an up-regulation of MuRF1 expression.

Hooijman et al., Am. J. Respir. Crit. Care. Med., 2015, 191(10), 1126-1138, describe a link between MuRF1 expression and diaphragm myofiber force loss and muscle protein degradation typically observed in critically ill patients receiving mechanical ventilation (critical illness myopathy). They observed that this myofiber force loss is attenuated in MuRF1-KO mice receiving mechanical ventilation, thereby revealing a connection between critical illness myopathy and MuRF1 expression.

Li and Granzier, Hum. Mol. Genet., 2015 Sep. 15, 24(18), 5219-5233, describe a mouse model for nemaline myopathy where muscles rich in glycolytic fibers upregulate proteolysis pathways including MuRF-1, and undergo hypotrophy, resulting in smaller cross-sectional areas (CSAs), thereby worsening their force deficit. Therefore, MuRF1 inhibition is predicted to protect myofiber CSA and myofiber force in nemaline myopathy, in particular for muscle types rich in glycolytic fibers such as M. quadriceps.

Adams et al., J. Mol. Biol., 2008, 384, 48-59, describe that the intraperitoneal injection of tumor necrosis factor alpha (TNF-α) in C57B16 mice reduced force development of the soleus muscle at 150 Hz by 25%. This TNF-α induced loss of muscle force was attenuated in MuRF-1 knockout animals. Thus, MuRF1 inhibition is predicted to be useful in chronic inflammatory states with elevated TNF-α levels.

De Man et al., Am. J. Respir. Crit. Care. Med., 2011 May 15, 183(10), 1411-1418, describe that the diaphragm fiber CSA is significantly smaller in rats with pulmonary hypertension (PH) compared with controls. In line with the rat data, studies on patients with PH revealed significantly reduced CSA and impaired contractility of diaphragm muscle fibers compared with control subjects. They further found that this reduction in diaphragm fiber CSA is associated with an increased expression of E3-ligases MAFbx and MuRF-1.

To date there exist only a limited amount of therapeutic approaches that are directed to the inhibition of MuRF1 function.

For example, Castillero et al., Metabolism, 2013, 62, 1495-1502, describe the adenoviral knock-down of atrogin-1 and MuRF1, which prevents dexamethasone-induced atrophy of cultured L6 myotubes.

Eddins et al., Cell Biochem. Biophys., 2011, 60, 113-118, describe the targeted inhibition of MuRF1 ubiquitylation by a muscle specific small molecule, which results in a significant reduction of muscle wasting in cellular atrophy models.

Although these therapeutic studies demonstrate that the inhibition of MuRF1 function by small molecules can prevent atrophy in myotubes, this approach has not yet been translated to an in vivo setting, such as in clinically-relevant animal models. Thus, there is still a virtually unmet need in the art to provide compounds and methods for the treatment and/or the prophylaxis of muscle wasting conditions.

BRIEF DESCRIPTION OF THE INVENTION

The object of the present invention is to provide further small molecules that are suitable for use in the treatment and/or the prophylaxis of muscle wasting conditions or of conditions which can be attenuated by improving muscle conditions.

This object and further objects are achieved by the compounds of the general formula I described below and the pharmaceutically acceptable salts thereof:

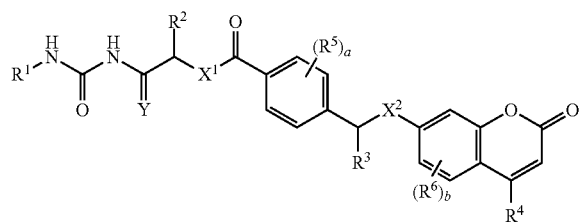

(I)

wherein
R¹ is hydrogen or a group —CH₂R¹ᵃ, where R¹ᵃ is selected from the group consisting of hydrogen, $C_1$-$C_3$-alkyl, phenyl, where phenyl is unsubstituted or may carry 1, 2 or 3 radicals independently selected from the group consisting of halogen, cyano, $C_1$-$C_3$-alkyl, $C_1$-$C_3$-haloalkyl and $C_1$-$C_3$-alkoxy; and a 5- to 10-membered heteroaromatic ring containing 1 to 4 heteroatoms or hetero-groups independently selected from the group consisting of N, NR$^c$, O and S as ring member(s), where the 5- to 10-membered heteroaromatic ring is unsubstituted or may carry 1, 2 or 3 radicals R⁷;

R² is hydrogen, methyl or fluorinated methyl;
R³ is hydrogen, methyl or fluorinated methyl;
R⁴ is hydrogen or $C_1$-$C_4$-alkyl;
each R⁵ is independently selected from the group consisting of halogen, cyano, $C_1$-$C_3$-alkyl, $C_1$-$C_3$-haloalkyl, $C_1$-$C_3$-alkoxy and $C_1$-$C_3$-haloalkoxy;
each R⁶ is independently selected from the group consisting of halogen, cyano, $C_1$-$C_3$-alkyl, $C_1$-$C_3$-haloalkyl, $C_1$-$C_3$-alkoxy and $C_1$-$C_3$-haloalkoxy;
each R⁷ is independently selected from the group consisting of halogen, cyano, $C_1$-$C_3$-alkyl, $C_1$-$C_3$-haloalkyl, $C_1$-$C_3$-alkoxy and $C_1$-$C_3$-haloalkoxy;
X¹ is NR$^a$ or O;
X² is NR$^b$, O or S;
Y represents an oxygen atom (so that C=Y is C=O) or two hydrogen atoms (so that C=Y is CH₂);
R$^a$, R$^b$, R$^c$ are each independently selected from the group consisting of hydrogen and $C_1$-$C_4$-alkyl;
a is 0, 1, 2, 3 or 4; and
b is 0, 1, 2 or 3.

The present invention therefore relates to the compounds of the general formula I and the pharmaceutically acceptable salts of the compounds of formula I.

Given the pharmacological properties of the compounds I, the present invention also relates to the compounds of the general formula I or the pharmaceutically acceptable salts thereof for use as a medicament.

It was found that the novel compounds are capable of attenuate muscle wasting and contractile dysfunction in cell tests as well as in clinically relevant animal models.

The present invention therefore relates to the compounds of the general formula I or the pharmaceutically acceptable salts of the compounds of formula I for use in the treatment or prophylaxis of muscle wasting conditions.

The present invention relates in particular to the compounds of the general formula I or the pharmaceutically acceptable salts of the compounds of formula I for use in the treatment or prophylaxis of skeletal or cardiac muscle atrophy resulting from one of the following diseases or conditions: congestive heart failure, chronic heart failure, cancer, cancer treatment with myotoxic substances, congenital myopathy, AIDS, chronic obstructive pulmonary disease (COPD), chronic renal diseases, renal failure, diabetes, severe burns, sarcopenia during aging, reduction in blood supply, temporary or long term immobilization, long term mechanical ventilation, denervation, prolonged weightlessness and malnutrition.

Furthermore, the compounds of the present invention are potent inhibitors of MuRF1 function by inhibiting the ubiquitin E3 ligase activity of MuRF1 and the binding of MuRF1 to target muscle proteins, such as titin. Thus, the present invention further relates to the compounds of the general formula I or the pharmaceutically acceptable salts of the compounds of formula I for use in the treatment or prophylaxis of conditions which are associated with an increased Muscle RING Finger 1 (MuRF1) expression, in particular of myopathies which are associated with an increased MuRF1 expression.

It was also found that the compounds of the general formula I have a beneficial effect in cardiac conditions associated with systolic or diastolic dysfunction which is not directly related to their effect on muscle conditions. The invention therefore also relates to the compound of the general formula I or a pharmaceutically acceptable salt thereof for use in the treatment or prophylaxis of cardiac conditions associated with systolic or diastolic dysfunction.

It was also found that the compounds of the general formula I have a beneficial effect in diabetes. The invention therefore also relates to the compound of the general formula I or a pharmaceutically acceptable salt thereof for use in the treatment or prophylaxis of diabetes, especially diabetes type II.

The invention further relates to a medicament, comprising at least one compound of the formula I, as described herein, or at least one pharmaceutically acceptable salt of the compound of the formula I.

The invention further relates to a pharmaceutical composition comprising a compound selected from compounds of the general formula I, as described herein, or at least one pharmaceutically acceptable salt thereof and at least one pharmaceutically acceptable carrier.

The invention further relates to the use of compounds selected from compounds of the general formula I, as defined herein, or pharmaceutically acceptable salts thereof for the manufacture of a medicament for the treatment or prophylaxis of muscle-wasting conditions; or for treatment or prophylaxis of the above-listed conditions or disorders.

The invention further relates to a method for treating or preventing one of the above-listed conditions or disorders, said method comprising the step of administering a compound selected from compounds of the general formula I, as defined herein, or a pharmaceutically acceptable salts thereof to a subject in need thereof.

DETAILED DESCRIPTION OF THE INVENTION

The terms "compound of the formula I" and "compounds I" are used as synonyms.

The term "pharmaceutically acceptable salts" refers to cationic or anionic salts compounds, wherein the counter ion is derived from pharmaceutically acceptable non-toxic bases or acids including inorganic or organic bases and inorganic or organic acids. It will be understood that, as used herein, references to the compounds of formula I are meant to also include the pharmaceutically acceptable salts.

If the compounds of formula I are basic, salts may be prepared from pharmaceutically acceptable non-toxic acids, including inorganic and organic acids. Such pharmaceutically acceptable acid addition salts include, but are not limited to, acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

If the compounds of formula I are acidic, salts may be prepared from pharmaceutically acceptable non-toxic bases, including inorganic and organic bases. Pharmaceutically acceptable base salts include nontoxic salts derived from bases, including metal cations, such as an alkali or alkaline earth metal cation, as well as amines. Examples of suitable metal cations include lithium, sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. Preferred pharmaceutically acceptable base salts are lithium, sodium, potassium, magnesium, calcium, zinc, aluminium and diethanolamine.

For a discussion of useful acid addition and base salts, see for example S. M. Berge et al., "Pharmaceutical Salts," 66 J. Pharm. ScL 1-19 (1977).

The term "$C_1$-$C_4$-alkyl" refers to methyl, ethyl, n-propyl, isopropyl, n-butyl, sec.-butyl, isobutyl or tert.-butyl. Preferably, $C_1$-$C_4$-alkyl is selected from methyl, ethyl, n-propyl, isopropyl, in particular from methyl and ethyl.

The term "$C_1$-$C_3$-alkyl" refers to methyl, ethyl, n-propyl or isopropyl. Preferably, $C_1$-$C_3$-alkyl is selected from methyl and ethyl, in particular from methyl.

The term "halogen" refers to fluorine, chlorine, bromine, and iodine. Preferably, halogen is fluorine and chlorine, in particular fluorine.

The term "fluorinated methyl" refers to fluoromethyl, difluoromethyl, trifluoromethyl, preferably to trifluoromethyl.

The term "fluorinated methoxy" refers to fluoromethoxy, difluoromethoxy, trifluoromethoxy, preferably to trifluoromethoxy.

The term "$C_1$-$C_3$-alkoxy" refers to methoxy, ethoxy, n-propoxy and isopropoxy. Preferably, $C_1$-$C_3$-alkoxy is selected from methoxy and ethoxy, in particular from methoxy.

The term "$C_1$-$C_3$-haloalkyl" refers to a $C_1$-$C_3$-alkyl radical as defined above, where at least one of the hydrogen atoms, for example 1, 2, 3, 4, 5 or 6 hydrogen atoms, of the $C_1$-$C_3$-alkyl radical has been replaced by a halogen atom, preferably by an chlorine or fluorine atom, in particular by a fluorine atom. Examples of $C_1$-$C_3$-haloalkyl include chloromethyl, dichloromethyl, trichloromethyl, 2-chloroethyl, 2,2-dichloroethyl, 2,2,2-trichloroethyl, fluoromethyl, difluoromethyl, trifluoromethyl, 2-fluoroethyl, 2,2-difluoroethyl, 2,2,2-trifluoroethyl, 1-fluoroethyl, 1,1-difluoroethyl, 1,1,2,2-tetrafluoroethyl, pentafluoroethyl etc. In particular, "$C_1$-$C_3$-haloalkyl" is selected from fluorinated methyl, as defined above, and also from trichloromethyl, 2,2,2-trichloroethyl, and 2,2,2-trifluoroethyl, especially from trifluoromethyl.

The term "$C_1$-$C_3$-haloalkoxy" refers to an $C_1$-$C_3$-alkoxy radical as defined above, where at least one of the hydrogen atoms, for example 1, 2, 3, 4, 5 or 6 hydrogen atoms, of the $C_1$-$C_3$-alkoxy radical has been replaced by a halogen atom, preferably by an chlorine or fluorine atom, in particular by a fluorine atom. Examples of $C_1$-$C_3$-haloalkoxy include chloromethoxy, dichloromethoxy, trichloromethoxy, 2-chloroethoxy, 2,2-dichloroethoxy, 2,2,2-trichloroethoxy, fluoromethoxy, difluoromethoxy, trifluoromethoxy, 2-fluoroethoxy, 2,2-difluoroethoxy, 2,2,2-trifluoroethoxy, 1-fluoroethoxy, 1,1-difluoroethoxy, 1,1,2,2-tetrafluoroethoxy, pentafluoroethoxy etc. In particular, "$C_1$-$C_3$-haloalkoxy" is selected from fluorinated methoxy, as defined above, and also from trichloromethoxy, 2,2,2-trichloroethoxy, and 2,2,2-trifluoroethoxy, especially from trifluoromethoxy.

The term "5- to 10-membered heteroaromatic ring" refers to a 5- to 6-membered monocyclic aromatic ring or a fused 8- to 10-membered bicyclic aromatic ring, where the monocylic or bicyclic aromatic ring contains 1 to 4 heteroatoms or hetero-groups independently selected from the group consisting of N, $NR^c$, O and S, wherein $R^c$ is selected from the group consisting of hydrogen and $C_1$-$C_4$-alkyl. Examples of such 5- to 6-membered monocyclic aromatic rings include thienyl, furyl, pyrrolyl, furazanyl, pyrazolyl, imidazolyl, oxazolyl, isoxazolyl, thiazolyl, isothiazolyl, 1,2,3-triazolyl, 1,2,4-triazolyl, oxadiazolyl, thiadiazolyl, pyridyl, pyrimidyl, pyridazinyl, pyrazinyl, 1,2,4-triazinyl, 1,3,6-triazinyl and the like. Examples of such 8- to 10-membered bicyclic aromatic rings include quinolinyl, isoquinolinyl, imidazopyridyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and the like.

In relation to their intended use, the variables $R^1$, $R^2$, $R^3$, $R^4$, $R^5$, $R^6$, $X^1$, $X^2$, Y, $R^a$, $R^b$, $R^c$, a and b in formula I in particular have the following meanings, where these represent, both considered on their own and in combination with at least one other or all, special embodiments of the compounds of the formula I.

$R^1$ is preferably hydrogen or a group —$CH_2R^{1a}$, where $R^{1a}$ is selected from the group consisting of hydrogen, methyl, phenyl and a 5- to 10-membered heteroaromatic ring containing 1 to 4 heteroatoms or hetero-groups independently selected from the group consisting of N, $NR^c$, O and S as ring member(s), where the 5- to 10-membered heteroaromatic ring is unsubstituted or may carry 1, 2 or 3 radicals $R^7$, wherein $R^c$ and $R^7$ have one of the above general meanings or, in particular, have one of the below preferred meanings.

More preferably, $R^1$ is selected from the group consisting of hydrogen and a group —$CH_2R^{1a}$, where $R^{1a}$ is selected from the group consisting of hydrogen, methyl and a 5- to 6-membered monocyclic heteroaromatic ring containing 1 to 3 heteroatoms, in particular 1 heteroatom, independently selected from the group consisting of N, O and S, as ring member(s), where the 5- to 6-membered monocyclic heteroaromatic ring is unsubstituted or carries 1 radical $R^7$, where $R^7$ is selected from the group consisting of halogen, $C_1$-$C_3$-alkyl and $C_1$-$C_2$-alkoxy.

In particular, $R^1$ is selected from the group consisting of hydrogen and a group —$CH_2R^{1a}$, where $R^{1a}$ is selected from the group consisting of hydrogen and an unsubstituted 5- to 6-membered monocyclic heteroaromatic ring containing 1 to 3 heteroatoms, in particular 1 heteroatom, independently selected from the group consisting of N, O and S, as ring member(s).

More particularly, $R^1$ is a group —$CH_2R^{1a}$, where $R^{1a}$ is an unsubstituted 5- to 6-membered monocyclic heteroaromatic ring containing 1 to 3 heteroatoms independently selected from the group consisting of N, O and S, as ring member(s). Specifically, $R^1$ is a group —$CH_2R^{1a}$, where $R^{1a}$ is an unsubstituted 5- to 6-membered monocyclic heteroaromatic ring containing 1 heteroatom selected from the group consisting of N, O and S as ring member. Very specifically, $R^1$ is a group —$CH_2R^{1a}$, where $R^{1a}$ is furyl, thienyl or pyridyl.

In an alternatively more preferred embodiment, $R^1$ is selected from hydrogen, methyl and the group $CH_2$—I' or $CH_2$—II'

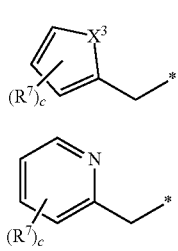

(CH$_2$-I')

(CH$_2$-II')

wherein * indicates the point of attachment to the urea nitrogen atom and wherein
X is $NR^c$, O or S;
c is 0, 1, 2 or 3; and
$R^7$ is as defined herein.

In particular, $R^1$ is selected from the group consisting of $CH_2$—I' and $CH_2$—II'

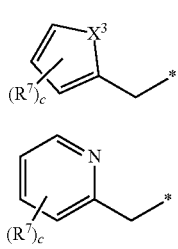

(CH$_2$-I')

(CH$_2$-II')

wherein * indicates the point of attachment to the urea nitrogen atom and wherein $R^7$, $X^3$ and c are as defined herein.

$R^2$ is preferably hydrogen or methyl. In particular $R^2$ is hydrogen.

$R^3$ is preferably hydrogen or methyl. In particular $R^3$ is hydrogen.

$R^4$ is preferably methyl or ethyl. In particular $R^4$ is methyl.

Preferably, each $R^5$ is independently selected from the group consisting of halogen, $C_1$-$C_3$-alkyl, $C_1$-$C_2$-haloalkyl and $C_1$-$C_2$-alkoxy fluorine. More preferably, each $R^5$ is independently selected from the group consisting of halogen, $C_1$-$C_3$-alkyl and $C_1$-$C_2$-alkoxy. Even more preferably, each $R^5$ is independently selected from the group consisting of fluorine, methyl and trifluoromethyl. In particular, each $R^5$ is independently selected from the group consisting of fluorine and methyl.

Preferably, each $R^6$ is independently selected from the group consisting of halogen, $C_1$-$C_3$-alkyl, $C_1$-$C_2$-haloalkyl and $C_1$-$C_2$-alkoxy fluorine. More preferably, each $R^6$ is independently selected from the group consisting of halogen, $C_1$-$C_3$-alkyl and $C_1$-$C_2$-alkoxy. Even more preferably, each $R^6$ is independently selected from fluorine, methyl and trifluoromethyl. In particular, each $R^6$ is independently selected from fluorine or methyl.

$X^1$ is $NR^a$ or O. Preferably, $X^1$ is NH or O.
Preferably, $X^2$ is O or S. In particular, $X^2$ is O.
In a preferred embodiment, Y is an oxygen atom. In another preferred embodiment, Y represents two hydrogen atoms.

Preferably, $R^a$, $R^b$, $R^c$ are each independently selected from the group consisting of hydrogen and $C_1$-$C_3$-alkyl. More preferably, $R^a$, $R^b$, $R^c$ are each independently selected from hydrogen and methyl. In particular, $R^a$, $R^b$, $R^c$ are hydrogen.

Preferably, a is 0, 1, 2 or 3. More preferably, a is 0, 1 or 2. In particular a is 0.

Preferably, b is 0, 1 or 2. More preferably, b is 0 or 1. In particular b is 0.

In the group of the formula $CH_2$—I' the variables $X^3$, c and $R^7$, if present, both considered on their own and in combination with at least one other or all, in particular have the following meanings:

Preferably, each $R^7$ is independently selected from the group consisting of halogen, $C_1$-$C_3$-alkyl, $C_1$-$C_2$-haloalkyl and $C_1$-$C_2$-alkoxy. More preferably, each $R^7$ is independently selected from the group consisting of halogen, $C_1$-$C_3$-alkyl and $C_1$-$C_2$-haloalkyl. Even more preferably, each $R^7$ is independently selected from fluorine, methyl and trifluoromethyl. In particular, each $R^7$ is independently selected from fluorine and methyl.

Preferably, $X^3$ is O or S. In particular, $X^3$ is O. In another particular embodiment, $X^3$ is S.

Preferably, c is 0, 1 or 2. More preferably, c is 0 or 1. In particular c is 0.

In the group of the formula $CH_2$—II' the variables c and $R^7$, if present, both considered on their own and in combination with at least one other or all, in particular have the following meanings:

Preferably, each $R^7$ is independently selected from the group consisting of halogen, $C_1$-$C_3$-alkyl, $C_1$-$C_2$-haloalkyl and $C_1$-$C_2$-alkoxy. More preferably, each $R^7$ is independently selected from the group consisting of halogen, $C_1$-$C_3$-alkyl and $C_1$-$C_2$-haloalkyl. Even more preferably, each $R^7$ is independently selected from fluorine, methyl and trifluoromethyl. In particular, each $R^7$ is independently selected from fluorine and methyl.

Preferably, c is 0, 1 or 2. More preferably, c is 0 or 1. In particular c is 0.

A preferred embodiment of the present invention relates to compounds of the general formula I, wherein,
$R^1$ is hydrogen or a group —$CH_2R^{1a}$, where $R^{1a}$ is hydrogen or an unsubstituted 5- to 6-membered monocyclic heteroaromatic ring containing 1 to 3 heteroatoms, in particular 1 heteroatom, independently selected from the group consisting of N, O and S, as ring member(s);
$R^2$ hydrogen or methyl;
$R^3$ is hydrogen or methyl;
$R^4$ is $C_1$-$C_2$-alkyl;
each $R^5$ is independently selected from the group consisting of halogen, $C_1$-$C_3$-alkyl, $C_1$-$C_2$-haloalkyl and $C_1$-$C_2$-alkoxy;
each $R^6$ is independently selected from the group consisting of halogen, $C_1$-$C_3$-alkyl, $C_1$-$C_2$-haloalkyl and $C_1$-$C_2$-alkoxy;
each $R^7$ is independently selected from the group consisting of halogen, $C_1$-$C_3$-alkyl, $C_1$-$C_2$-haloalkyl and $C_1$-$C_2$-alkoxy;

$X^1$ is $NR^a$ or O;
$X^2$ is O or S;
Y represents an oxygen atom or two hydrogen atoms;
$R^a$ is selected from the group consisting of hydrogen and $C_1$-$C_3$-alkyl;
a is 0, 1, 2 or 3; and
b is 0, 1 or 2;
and the pharmaceutically acceptable salts thereof.

A more preferred embodiment of the present invention relates to compounds of the general formula I, wherein,
$R^1$ is hydrogen or a group —$CH_2R^{1a}$, where $R^{1a}$ is hydrogen or an unsubstituted 5- to 6-membered monocyclic heteroaromatic ring containing 1 heteroatom selected from the group consisting of N, O and S as ring member;
$R^2$ is hydrogen or methyl;
$R^3$ is hydrogen;
$R^4$ is methyl;
$X^1$ is NH or O;
$X^2$ is O;
Y represents an oxygen atom or two hydrogen atoms;
a is 0; and
b is 0;
and the pharmaceutically acceptable salts thereof.

A particular embodiment of the present invention relates to compounds of the general formula I, wherein,
$R^1$ is a group —$CH_2R^{1a}$, where $R^{1a}$ is an unsubstituted 5- to 6-membered monocyclic heteroaromatic ring containing 1 heteroatom selected from the group consisting of N, O and S as ring member;
$R^2$ is hydrogen;
$R^3$ is hydrogen;
$R^4$ is methyl;
$X^1$ is NH or O;
$X^2$ is O;
Y represents an oxygen atom or two hydrogen atoms;
a is 0; and
b is 0;
and the pharmaceutically acceptable salts thereof.

Another preferred embodiment of the present invention relates to compounds of the general formula I, wherein,
$R^1$ is hydrogen, methyl or a group $CH_2$—I' or $CH_2$—II';
$R^2$ is selected from hydrogen and methyl;
$R^3$ is selected from hydrogen and methyl;
$R^4$ is $C_1$-$C_2$-alkyl;
each $R^5$ is independently selected from the group consisting of halogen, $C_1$-$C_3$-alkyl, $C_1$-$C_2$-haloalkyl and $C_1$-$C_2$-alkoxy;
each $R^6$ is independently selected from the group consisting of halogen, $C_1$-$C_3$-alkyl, $C_1$-$C_2$-haloalkyl and $C_1$-$C_2$-alkoxy;
each $R^7$ is independently selected from the group consisting of halogen, $C_1$-$C_3$-alkyl, $C_1$-$C_2$-haloalkyl and $C_1$-$C_2$-alkoxy;
$X^1$ is $NR^a$ or O;
$X^2$ is O or S;
$X^3$ is O or S;
Y represents an oxygen atom or two hydrogen atoms;
$R^a$ is selected from the group consisting of hydrogen and $C_1$-$C_3$-alkyl;
a is 0, 1, 2 or 3;
b is 0, 1 or 2; and
c is 0, 1 or 2;
and the pharmaceutically acceptable salts thereof.

Another more preferred embodiment of the present invention relates to compounds of the general formula I, wherein,
$R^1$ is hydrogen, methyl or a group $CH_2$—I' or $CH_2$—II';
$R^2$ is hydrogen or methyl;
$R^3$ is hydrogen;
$R^4$ is methyl;
each $R^5$ is independently selected from the group consisting of halogen, $C_1$-$C_3$-alkyl and $C_1$-$C_2$-alkoxy;
each $R^6$ is independently selected from the group consisting of halogen, $C_1$-$C_3$-alkyl and $C_1$-$C_2$-alkoxy;
each $R^7$ is independently selected from the group consisting of halogen, $C_1$-$C_3$-alkyl and $C_1$-$C_2$-alkoxy;
$X^1$ is NH or O;
$X^2$ is O;
$X^3$ is O or S;
Y represents an oxygen atom or two hydrogen atoms;
a is 0, 1 or 2;
b is 0 or 1; and
c is 0 or 1;
and the pharmaceutically acceptable salts thereof.

An even more preferred embodiment of the present invention relates to compounds of the general formula I, wherein,
$R^1$ is hydrogen, methyl or a group $CH_2$—I' or $CH_2$—II';
$R^2$ is hydrogen or methyl;
$R^3$ is hydrogen;
$R^4$ is methyl;
each $R^5$ is independently selected from the group consisting of halogen, $C_1$-$C_3$-alkyl and $C_1$-$C_2$-alkoxy;
each $R^6$ is independently selected from the group consisting of halogen, $C_1$-$C_3$-alkyl and $C_1$-$C_2$-alkoxy;
each $R^7$ is independently selected from the group consisting of halogen, $C_1$-$C_3$-alkyl and $C_1$-$C_2$-alkoxy;
$X^1$ is NH or O;
$X^2$ is O;
$X^3$ is O or S;
Y represents an oxygen atom or two hydrogen atoms;
a is 0;
b is 0; and
c is 0;
and the pharmaceutically acceptable salts thereof.

Another particular embodiment of the present invention relates to compounds of the general formula I, wherein,
$R^1$ is a group $CH_2$—I' or $CH_2$—II';
$R^2$ is hydrogen;
$R^3$ is hydrogen;
$R^4$ is methyl;
$X^1$ is NH or O;
$X^2$ is O;
$X^3$ is O or S;
Y represents an oxygen atom or two hydrogen atoms;
a is 0;
b is 0; and
c is 0;
and the pharmaceutically acceptable salts thereof.

Another preferred group of embodiments relates to compounds of the general formula I, wherein the group $CH_2$—I',
$X^3$ is O or S;
each $R^7$ is independently selected from the group consisting of halogen, $C_1$-$C_3$-alkyl, $C_1$-$C_2$-haloalkyl and $C_1$-$C_2$-alkoxy; and
c is 0, 1 or 2.

Another preferred group of embodiments relates to compounds of the general formula I, wherein the group $CH_2$—II',
each $R^7$ is independently selected from the group consisting of halogen, $C_1$-$C_3$-alkyl, $C_1$-$C_2$-haloalkyl and $C_1$-$C_2$-alkoxy; and
c is 0, 1 or 2.

An even more preferred group of embodiments relates to compounds of the general formula I, wherein the group CH₂—I',
$X^3$ is O or S;
each $R^7$ is independently selected from fluorine, methyl or trifluoromethyl; and
c is 0 or 1.

An even more preferred group of embodiments relates to compounds of the general formula I, wherein the group CH₂—II', each $R^7$ is independently selected from fluorine, methyl or trifluoromethyl; and c is 0 or 1.

A particularly preferred embodiment of the invention relates to a compound of formula I, which corresponds to the formula I-A,

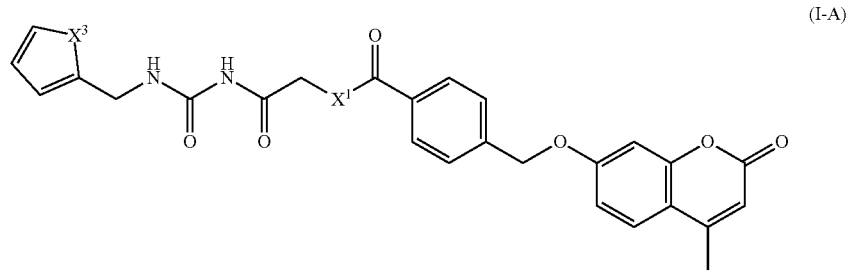

(I-A)

wherein
$X^1$ is NH or O; and
$X^3$ is O or S;
and the pharmaceutically acceptable salts thereof.

Another particularly preferred embodiment of the invention relates to a compound of formula I, which corresponds to the formula I-B,

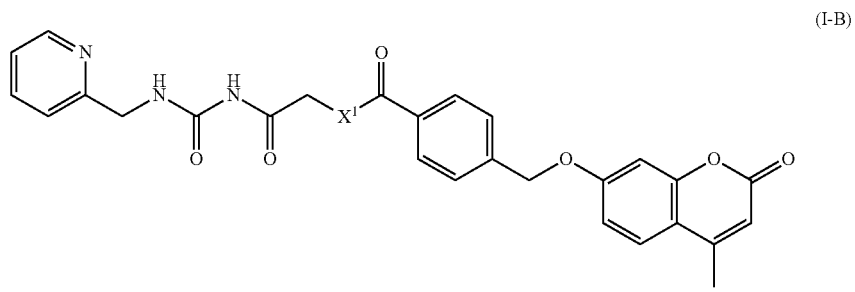

(I-B)

wherein
$X^1$ is NH or O;
and the pharmaceutically acceptable salts thereof.

Another particularly preferred embodiment of the invention relates to a compound of formula I, which corresponds to the formula I-C,

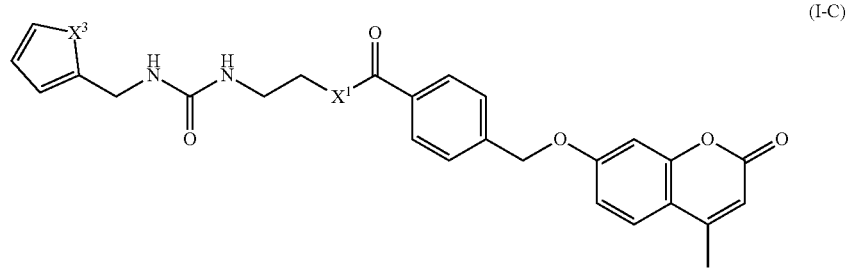

(I-C)

wherein
X¹ is NH or O; and
X³ is O or S;
and the pharmaceutically acceptable salts thereof.

Another particularly preferred embodiment of the invention relates to compounds of formula I, which corresponds to the formula I-D,

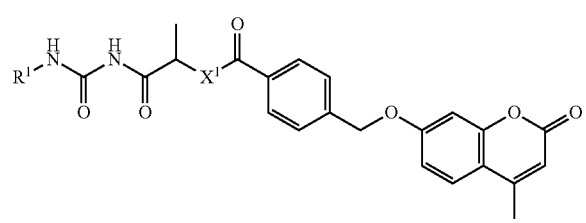

(I-D)

wherein
R¹ is selected from hydrogen or methyl; and
X¹ is NH or O;
and the pharmaceutically acceptable salts thereof.

An especially preferred compound of formula I is [2-(2-furylmethylcarbamoyl-amino)-2-oxo-ethyl] 4-[(4-methyl-2-oxo-chromen-7-yl)oxymethyl]benzoate (i.e. a compound I wherein R¹ is a group —CH$_2$R$^{1a}$, where R$^{1a}$ is furan-2-yl, R² is H, R³ is H, R⁴ is methyl, X¹ is O, X² is O, Y is O, a is 0 and b is 0) and its pharmaceutically acceptable salts. This compound is also termed MyoMed-946 in the following.

Another especially preferred compound of formula I is N-[2-(2-furylmethylcarbamoylamino)-2-oxo-ethyl]-4-[(4-methyl-2-oxo-chromen-7-yl)oxymethyl]benzamide (i.e. a compound I wherein R¹ is a group —CH$_2$R$^{1a}$, where R$^{1a}$ is furan-2-yl, R² is H, R³ is H, R⁴ is methyl, X¹ is NH, X² is O, Y is O, a is 0 and b is 0) and its pharmaceutically acceptable salts.

Another especially preferred compound of formula I is [2-oxo-2-(2-thienylmethylcarbamoylamino)ethyl] 4-[(4-methyl-2-oxo-chromen-7-yl)oxymethyl]-benzoate (i.e. a compound I wherein R¹ is a group —CH$_2$R$^{1a}$, where R$^{1a}$ is thien-2-yl, R² is H, R³ is H, R⁴ is methyl, X¹ is O, X² is O, Y is O, a is 0 and b is 0) and its pharmaceutically acceptable salts.

Another especially preferred compound of formula I is 4-[(4-methyl-2-oxo-chromen-7-yl)oxymethyl]-N-[2-oxo-2-(2-thienylmethylcarbamoylamino)ethyl]-benzamide (i.e. a compound I wherein R¹ is a group —CH$_2$R$^{1a}$, where R$^{1a}$ is thien-2-yl, R² is H, R³ is H, R⁴ is methyl, X¹ is NH, X² is O, Y is O, a is 0 and b is 0) and its pharmaceutically acceptable salts.

Another especially preferred compound of formula I is [2-oxo-2-(2-pyridylmethylcarbamoylamino)ethyl] 4-[(4-methyl-2-oxo-chromen-7-yl)oxy-methyl]benzoate (i.e. a compound I wherein R¹ is a group —CH$_2$R$^{1a}$, where R$^{1a}$ is pyridin-2-yl, R² is H, R³ is H, R⁴ is methyl, X¹ is O, X² is O, Y is O, a is 0 and b is 0) and its pharmaceutically acceptable salts. This compound is also termed MyoMed-203 in the following.

Another especially preferred compound of formula I is 4-[(4-methyl-2-oxo-chromen-7-yl)oxymethyl]-N-[2-(2-thienylmethylcarbamoylamino)ethyl]benzamide (i.e. a compound I wherein R¹ is a group —CH$_2$R$^{1a}$, where R$^{1a}$ is thien-2-yl, R² is H, R³ is H, R⁴ is methyl, X¹ is NH, X² is O, Y represents two hydrogen atoms (i.e. C=Y is CH$_2$), a is 0 and b is 0) and its pharmaceutically acceptable salts. This compound is also termed MyoMed-205 in the following.

Another especially preferred compound of formula I is (1-methyl-2-oxo-2-ureido-ethyl) 4-[(4-methyl-2-oxo-chromen-7-yl)oxymethyl]benzoate (i.e. a compound I wherein R¹ is H, R² is methyl, R³ is H, R⁴ is methyl, X¹ is O, X² is O, Y is O, a is 0 and b is 0) and its pharmaceutically acceptable salts. This compound is also termed MyoMed-946-5 in the following.

Another especially preferred compound of formula I is [1-methyl-2-(methylcarbamoyl-amino)-2-oxo-ethyl] 4-[(4-methyl-2-oxo-chromen-7-yl)oxymethyl]-benzoate (i.e. a compound I wherein R¹ is a group —CH$_2$R$^{1a}$, where R$^{1a}$ is H, R² is methyl, R³ is H, R⁴ is methyl, X¹ is O, X² is O, Y is O, a is 0 and b is 0) and its pharmaceutically acceptable salts. This compound is also termed MyoMed-946-8 in the following.

The compounds I according to the invention can be prepared by analogy to methods known from the literature. An important approach to the compounds according to the invention is offered by the reaction of a 4-bromoalkyl-substituted methylbenzoate compound II with a chromen-2-on compound III to the 2-oxochromen-substituted methylbenzoate compound IV, which is hydrolyzed to the intermediate benzoic acid compound V, as depicted in scheme 1.

Scheme 1

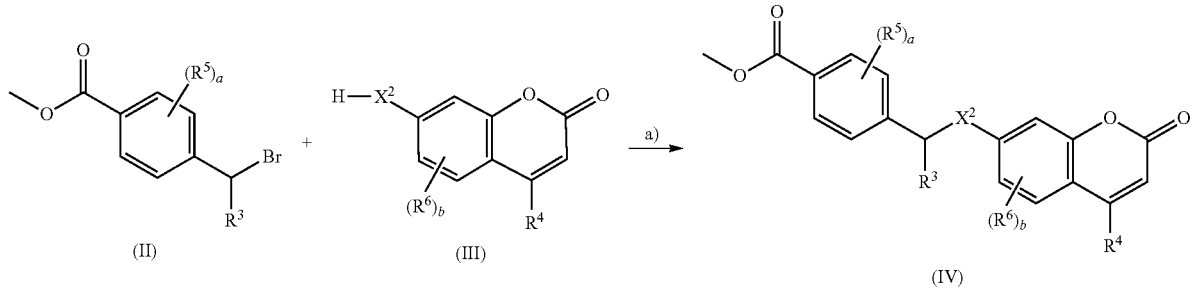

-continued

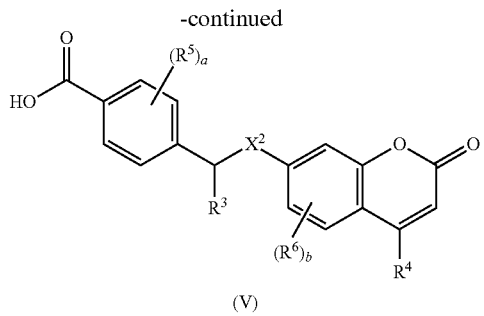

(V)

In scheme 1 the variables $R^3$, $R^4$, $R^5$, $R^6$, $X^2$, a and b have the aforementioned meanings.

In step a) of scheme 1, the bromide of the formula (II) reacts with the OH, SH or $HNR^b$ group (H—$X^2$-group) of compound III, under conditions suitable for nucleophilic substitution reactions. The skilled person is familiar with the reaction conditions which are required for this type of nucleophilic substitution reaction. Typically, this reaction is performed in the presence of a base. Suitable bases can be inorganic or organic. Examples for suitable inorganic bases are alkali metal carbonates, e.g. $Li_2CO_3$, $Na_2CO_3$, $K_2CO_3$ or $Cs_2CO_3$, alkali metal hydroxides, e.g. LiOH, NaOH or KOH, or phosphates, e.g. $Li_3PO_4$, $Na_3PO_4$, $K_3PO_4$ or $Cs_3PO_4$. Examples for suitable organic bases are for example tertiary amines, e.g. trimethylamine, triethylamine, tripropylamine, ethyldiisopropylamine (DIPEA) and the like, basic N-heterocycles, such as morpholine, pyridine, lutidine, DABCO, DBU or DBN, or alkoxylates, such as sodium or potassium methanolate, ethanolate, propanolate, isopropanolate, butanolate or tert-butanolate.

The thus obtained methyl ester compound of formula (IV) is saponified in step b) of scheme 1 in the presence of a strong base, such as alkali metal hydroxides, e.g. LiOH, NaOH or KOH, to yield the benzoic acid compound of formula (V).

The intermediate benzoic acid compound V is then further reacted with a urea compound VIa or VIb to yield the compounds I according to the present invention, as depicted in scheme 2.

In scheme 2, the variables $R^1$, $R^2$, $R^3$, $R^4$, $R^5$, $R^6$, $X^2$, Y, $R^a$, a and b have the aforementioned meanings.

In step c) of scheme 2, the benzoic acid intermediate of formula (V) is reacted either with a urea compound of formula (VIa) containing a chloride group or with a urea compound of formula (VIb) containing a $N(H)R^a$ group to from the corresponding ester or amide compounds of the formula I. The reaction of the benzoic acid intermediate of formula (V) with the urea compound of formula (VIa) containing a chloride group in step c) of scheme 2 is performed under conditions suitable for nucleophilic substitution reactions. The skilled person is familiar with the reaction conditions required for these types of reactions. Typically, this reaction is performed in the presence of a base, as defined above, to neutralize the acid formed during the reaction. If desired, compounds (VIa) can be further activated in situ by adding suitable bromide- or, in particular, iodide salts, to the nucleophilic substitution reaction. Suitable bromide- or iodide salts are, for example, alkali metal bromides or iodides and tetraalkylammonium bromides or iodides. Examples include sodium bromide, sodium iodide, potassium bromide, potassium iodide, tetrabutylammonium bromide and tetrabutylammonium iodide.

The reaction of the benzoic acid intermediate of formula (V) with the urea compound of formula (VIb) containing a $N(H)R^a$ group in step c) of scheme 2 is performed under conditions suitable for amide bond formation. The skilled person is familiar with the reaction conditions which are required for this type of reaction. Typically, the amide bond Scheme 2

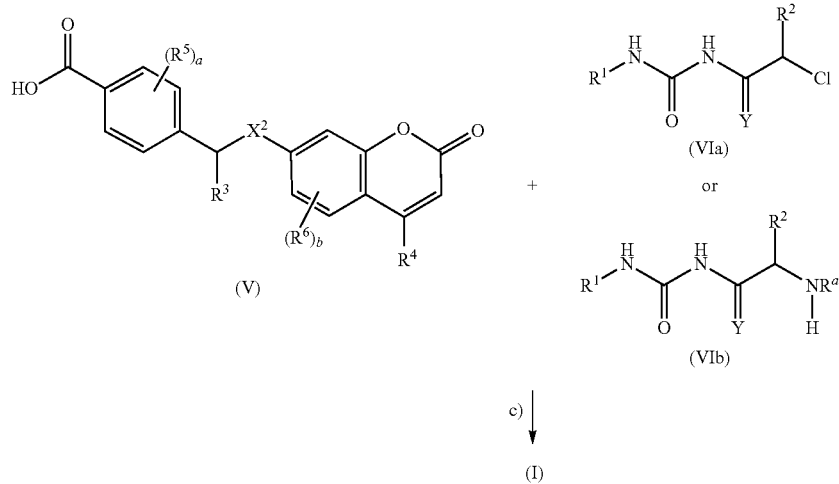

formation is carried out in the presence of a coupling reagent. Suitable coupling reagents (activators) are well known and are for instance selected from the group consisting of carbodiimides, such as EDCI (1-ethyl-3-(3-dimethylaminopropyl)carbodiimide; also abbreviated as EDC), DCC (dicyclohexylcarbodiimide) and DIC (diisopropylcarbodiimide), benzotriazole derivatives, such as HOAt (1-hydroxy-7-azabenzotriazole, HOBt (1-hydroxybenzotriazole), HATU (0-(7-azabenzotriazol-1-yl)-N,N,N',N'-tetramethyl-uronium hexafluorophosphate), HBTU ((O-benzotriazol-1-yl)-N,N,N',N'-tetramethyluronium hexafluorophosphate) and HCTU (1H-benzotriazolium-1-[bis(dimethylamino)methylene]-5-chloro tetrafluoroborate), phosphonium-derived activators, such as BOP ((benzotriazol-1-yloxy)-tris(dimethylamino)phosphonium hexafluorophosphate), Py-BOP ((benzotriazol-1-yloxy)-tripyrrolidinphosphonium hexafluorophosphate) and Py-BrOP (bromotripyrrolidin-phosphonium hexafluorophosphate), and others, such as COMU ((1-cyano-2-ethoxy-2-oxoethylidenaminooxy)dim-ethylamino-morpholino-carbenium-hexafluorophosphat).

The above activators can also be used in combination with each other. Generally, the activator is used in at least equimolar amounts, with respect to that reactant not used in excess. The benzotriazole and phosphonium coupling reagents are generally used in a basic medium. Alternatively, the carboxylic acid intermediate of formula (V) can be first converted into a so-called active ester, which is obtained in a formal sense by the reaction of the carboxylic acid with an active ester-forming alcohol, such as p-nitrophenol, N-hydroxybenzotriazole (HOBt), N-hydroxysuccinimide or OPfp (pentafluorophenol). The active ester is then reacted with the amine 3 either in the presence or the absence of a coupling reagent.

Compounds of the formula (II) and (III) can either be purchased or can be synthesized using processes that are well known to the skilled person.

Compounds of the formula (VIa) and (VIb) can either be purchased or synthesized, e.g. following the procedure as depicted in scheme 3.

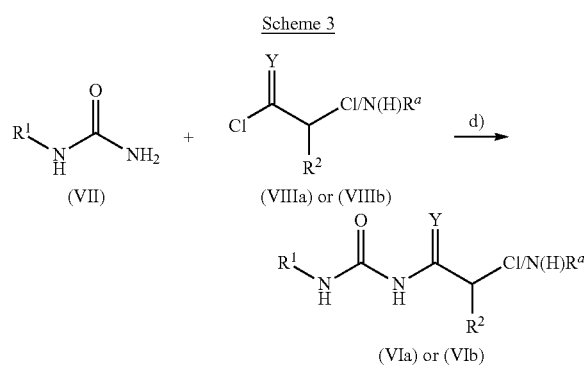

In scheme 3 the variables $R^1$, $R^2$ and $R^a$ have the aforementioned meanings. In step d) of scheme 3, in case where Y represents an oxygen atom, the urea compound (VII) is reacted with the acid chloride (VIIIa) or (VIIIb), under nucleophilic acylation conditions. Reaction conditions suitable for acylation reactions are well known to the skilled person. In case where Y represents two hydrogen atoms, is performed under conditions suitable for nucleophilic substitution reactions. The skilled person is familiar with the reaction conditions required for these types of reactions. If desired, compounds (VIIIa) can be further activated in situ as described above. Typically, step d) is performed in the presence of a base, such as tertiary amines, as defined above, to quench the hydrochloride or other acids, which are formed during the reaction.

In some particular cases it may be necessary to use appropriate protecting groups in order to avoid side reactions with other reactive groups, which may be present in compounds (VII), (VIIIa) or (VIIIb) and may compete in or disturb the reaction. In these cases, additional deprotecting steps may be necessary to remove these protecting groups after amide bond formation. Suitable protecting groups and the methods for protecting and deprotecting different substituents using such suitable protecting groups are well known to those skilled in the art; examples of which may be found in T. Greene and P. Wuts, Protective Groups in Organic Synthesis (3$^{rd}$ ed.), John Wiley & Sons, NY (1999).

Furthermore, compounds (VIc) can be prepared from compounds (VIa) e.g. following the procedure as depicted in scheme 4.

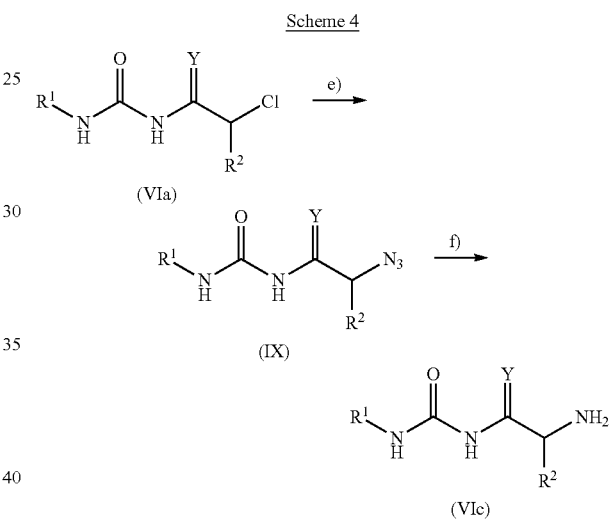

In scheme 4 the variables $R^1$, $R^2$ and Y have the aforementioned meanings. In step e) of scheme 4 the urea compound (VIa) is transferred to the azide compound (IX) in the presence of an azide source, such as a phosphoryl azide, hydrazoic acid or sodium azide, azide, or via Staudinger reaction with PPh$_3$ or other phosphorus reagents, as described by Zwierzak, A. in Phosphorus, Sulfur, and Silicon and the Related Elements (1993), 75:1-4, 51-54. Typically, step e) is performed in the presence of a base, such as tertiary amines, as defined above, to quench the hydrochloride, which is formed during the reaction.

In step f) of scheme 4, the azide group of compounds (IX) is reduced with hydrogen in the presence of a hydrogenation catalyst or reacted with a hydride to give the amine compounds (VIc). Reaction conditions suitable for this type of reactions are well known to the skilled person.

If not indicated otherwise, the above-described reactions are typically performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures between room temperature and the boiling temperature of the solvent employed, depending on the reactivity of the used compounds.

The reaction mixtures are worked up in a conventional way, e.g. by mixing with water, separating the phases and, where appropriate, purifying the crude products by chromatography. If the intermediates and final products are obtained as solids, the purification can also take place by recrystallization or digestion.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

As already stated above, it was found that the compounds of the general formula I are capable of attenuate muscle wasting and contractile dysfunction in cell tests as well as in clinically relevant animal models.

Thus, the invention relates to the compounds of the general formula I, as defined above, for use in the treatment or prophylaxis of muscle wasting conditions.

The terms "treating" and "treatment", as used herein in connection with muscle wasting conditions and myopathies, refer to the treatment of the symptoms, i.e. muscle wasting or muscle weakening, associated with a condition and/or a disease.

The term "prophylaxis", as used herein in connection with muscle wasting conditions and myopathies, refers to a prophylactic treatment, i.e. a treatment for preventing or reducing the risk of muscle wasting or muscle weakening, associated with a condition and/or a disease.

The term "muscle wasting", as used herein, has to be understood as referring to a decrease in size (reduced cross sectional area) and numbers of muscle fibers, visible as a decrease in the mass of the muscle, which is also referred to as muscle atrophy in scientific and medical literature.

The term "myopathy", as used herein, refers to a disease of muscle, in which the muscle fibers do not function properly. This results in muscular weakness. The term "myopathy", as used herein, refers in particular to myopathies, which are associated with an increased Muscle RING Finger 1 (MuRF1) expression. It is however assumed that the effect of the present compounds is not limited to that pathway.

Muscle wasting is assumed to be caused by a change in the balance between muscle protein synthesis and muscle protein degradation. In particular, it is assumed that during atrophy muscle protein degradation pathways are activated, such as the ubiquitination of muscle proteins.

Muscle wasting is typically observed in patients suffering from cachexia, for instance cachexia caused by cardiac diseases, i.e. cardiac cachexia. Furthermore, muscle wasting in particular affects skeletal muscles, leading to a degradation of skeletal muscles, i.e. skeletal muscle atrophy. Muscle wasting can however also affect cardiac muscles.

Therefore, a preferred embodiment of the present invention relates to the compounds of the general formula I, as defined above, for use in the treatment or prophylaxis of cardiac cachexia, skeletal muscle atrophy or cardiac muscle atrophy.

Cardiac cachexia, cardiac and skeletal muscle atrophy are for example observed in patients suffering from myocardial infarction, which typically leads to an exacerbation of their symptoms and prognosis and which can significantly prolong their convalescence.

Thus, a particular embodiment of the present invention relates to the compounds of the general formula I, as defined above, for use in the treatment or prophylaxis of cardiac cachexia, skeletal muscle atrophy or cardiac muscle atrophy, where the cardiac cachexia and cardiac or skeletal muscle atrophy are caused by myocardial infarction.

There are a vast number of disease related conditions known, but also numerous physical conditions that are not linked to a disease, which cause cardiac or skeletal muscle atrophy and/or cachexia.

Disease related conditions, which can cause cardiac or skeletal muscle atrophy and/or cachexia, are for example congestive heart failure, chronic heart failure, myocardial infarction, cancer, congenital myopathy, AIDS, chronic obstructive pulmonary disease (COPD), multiple sclerosis, familial amyloid polyneuropathy, reduction in blood supply, hormonal deficiency, chronic renal disease, renal failure, diabetes, infectious disease, chronic pancreatitis and autoimmune disorders.

Physical conditions, which can cause skeletal muscle atrophy and/or cachexia, and which are not linked to a disease, are for example severe burns, denervation, temporary or long term immobilization, long term mechanical ventilation, sarcopenia during aging, prolonged weightlessness, malnutrition and drug addiction.

Certain chemotherapeutic agents used in cancer treatment show cardio- and myotoxicity. For instance, the use of doxorubicin, which is an efficient chemotherapeutic drug used in various cancer treatments, is associated with early and chronic cardiotoxicity and myotoxicity (K. M. Cho et al., Oncotarget, 2017, 8(45), 79441-79452; D. S. Hydock et al., Characterization of the Effect of In Vivo Doxorubicin Treatment on Skeletal Muscle Function in the Rat, International Journal of Cancer Research and Treatment, 2011, 2028, 2023-2028; T. A. Nissinen et al., Sci. Rep., 2016, 6, 32695; M. S. Willis et al., Circulation: Heart Failure, 2019, 12(3), 1-12). In rodents, a single injection of doxorubicin is capable of reducing heart and skeletal muscle mass, followed by a marked impairment of function.

A preferred embodiment of the present invention relates to the compounds of the general formula I, as defined above, for use in the treatment or prophylaxis of skeletal or cardiac muscle atrophy resulting from one of the following diseases or conditions: congestive heart failure, chronic heart failure, cancer, cancer treatment with myotoxic substances, congenital myopathy, AIDS, chronic obstructive pulmonary disease (COPD), chronic renal disease, renal failure, diabetes, severe burns, sarcopenia during aging, reduction in blood supply, temporary or long term immobilization, long term mechanical ventilation, denervation, prolonged weightlessness and malnutrition.

The present invention also relates to the treatment or prophylaxis of diabetes, especially of diabetes type II. Without wishing to be bound by theory, it is assumed that the positive effect on diabetes is based on MuRF1 inhibition which enhances insulin sensitivity of muscles. S. Hirner et al. showed in J. Mol. Biol., 2008, 379, 666-677 that MuRF1 and insulin can be understood as functionally connected in an antagonist fashion in the sense that MuRF1 depletes glycogen stores and inhibits glycolysis, whereas insulin upregulates glycolysis and glycogen stores. Consequently, inhibition of MuRF1 can lead to a lower requirement of insulin and constitute a strategy for treating diabetes.

The present invention in particular relates to:

The compounds of the general formula I, as defined above, for use in the treatment or prophylaxis of skeletal or cardiac muscle atrophy resulting from congestive heart failure.

The compounds of the general formula I, as defined above, for use in the treatment or prophylaxis of skeletal or cardiac muscle atrophy resulting from chronic heart failure.

The compounds of the general formula I, as defined above, for use in the treatment or prophylaxis of skeletal or cardiac muscle atrophy resulting from cancer.

The compounds of the general formula I, as defined above, for use in the treatment or prophylaxis of skeletal or cardiac muscle atrophy resulting from cancer treatment with myotoxic and/or cardiotoxic substances, such as doxorubicin.

The compounds of the general formula I, as defined above, for use in the treatment or prophylaxis of skeletal or cardiac muscle atrophy resulting from congenital myopathy.

The compounds of the general formula I, as defined above, for use in the treatment or prophylaxis of skeletal or cardiac muscle atrophy resulting from AIDS.

The compounds of the general formula I, as defined above, for use in the treatment or prophylaxis of skeletal or cardiac muscle atrophy resulting from chronic obstructive pulmonary disease (COPD).

The compounds of the general formula I, as defined above, for use in the treatment or prophylaxis of skeletal or cardiac muscle atrophy resulting from chronic renal disease.

The compounds of the general formula I, as defined above, for use in the treatment or prophylaxis of skeletal or cardiac muscle atrophy resulting from renal failure.

The compounds of the general formula I, as defined above, for use in the treatment or prophylaxis of skeletal or cardiac muscle atrophy resulting from diabetes.

The compounds of the general formula I, as defined above, for use in the treatment or prophylaxis of skeletal or cardiac muscle atrophy resulting from severe burns.

The compounds of the general formula I, as defined above, for use in the treatment or prophylaxis of skeletal or cardiac muscle atrophy resulting from sarcopenia during aging.

The compounds of the general formula I, as defined above, for use in the treatment or prophylaxis of skeletal or cardiac muscle atrophy resulting from reduction in blood supply.

The compounds of the general formula I, as defined above, for use in the treatment or prophylaxis of skeletal or cardiac muscle atrophy resulting from temporary or long term immobilization.

The compounds of the general formula I, as defined above, for use in the treatment or prophylaxis of skeletal or cardiac muscle atrophy resulting from long term mechanical ventilation.

The compounds of the general formula I, as defined above, for use in the treatment or prophylaxis of skeletal or cardiac muscle atrophy resulting from denervation.

The compounds of the general formula I, as defined above, for use in the treatment or prophylaxis of skeletal or cardiac muscle atrophy resulting from prolonged weightlessness.

The compounds of the general formula I, as defined above, for use in the treatment or prophylaxis of skeletal or cardiac muscle atrophy resulting from malnutrition.

The compounds of the general formula I, as defined above, for use in the treatment or prophylaxis of diabetes.

The present invention in particular further relates to:

The compounds of the general formula I, as defined above, for use in the treatment or prophylaxis of cardiac cachexia.

The compounds of the general formula I, as defined above, for use in the treatment or prophylaxis of tumor cachexia.

The compounds of the general formula I, as defined above, for use in the treatment of myocardial infarction.

The compounds of the general formula I, as defined above, for use in the treatment of chronic heart failure.

The compounds of the general formula I, as defined above, for use in the recovery from mechanical ventilation.

The present invention specifically relates to:

The compounds of the general formula I, as defined above, for use in the treatment or prophylaxis of skeletal or cardiac muscle atrophy resulting from or associated with heart failure with reduced ejection fraction (HF-rEF).

The compounds of the general formula I, as defined above, for use in the treatment or prophylaxis of skeletal or cardiac muscle atrophy resulting from or associated with heart failure with preserved ejection fraction (HF-pEF).

The compounds of the general formula I, as defined above, for use in the treatment or prophylaxis of skeletal or cardiac muscle atrophy resulting from or associated with hypertension.

The compounds of the general formula I, as defined above, for use in the treatment or prophylaxis of skeletal or cardiac muscle atrophy resulting from or associated with tumor cachexia.

The compounds of the general formula I, as defined above, for use in the treatment or prophylaxis of muscle atrophy and/or cardiac toxicity induced by Doxorubicin.

The compounds of the general formula I, as defined above, for use in the treatment or prophylaxis of sarcopenia and/or cardiomyopathy due to aging.

The compounds of the general formula I, as defined above, for use in the treatment or prophylaxis of muscle atrophy due to chronic renal disease.

The compounds of the general formula I, as defined above, for use in the treatment or prophylaxis of diaphragm weakness due to mechanical ventilation or congestive heart failure.

The compounds of the general formula I, as defined above, for use in the treatment or prophylaxis of congenital myopathy, in particular congenetic muscle atrophy.

The compounds of the general formula I, as defined above, for use in the treatment or prophylaxis of diabetes-induced muscle atrophy.

The compounds of the general formula I, as defined above, for use in the treatment or prophylaxis of diabetes, in particular of diabetes type II.

Due to their capability to downregulate the function of MuRF1 by inhibiting the ubiquitin E3 ligase activity of MuRF1 as well as by inhibiting the binding of MuRF1 to target muscle proteins, such as titin, the compounds of the formula I and the pharmaceutically acceptable salts thereof, are also suitable for use in the treatment or prophylaxis of conditions associated with an increased Muscle RING Finger 1 (MuRF1) expression; and in particular of myopathies which are associated with misbalanced muscle protein synthesis and muscle protein degradation leading to muscle wasting and myopathy, typically associated with an increased Muscle RING Finger 1 (MuRF1) expression.

Thus, the invention further relates to the compounds of formula I, as defined above, for use in the treatment or prophylaxis of conditions which are associated with an increased Muscle RING Finger 1 (MuRF1) expression.

In particular, the invention further relates to the compounds of formula I, as defined above, for use in the treatment or prophylaxis of myopathies, which are associated with an increased Muscle RING Finger 1 (MuRF1) expression.

Myopathies, which are associated with an increased MuRF1 expression are for example selected from critical illness myopathy, nemaline myopathy, inflammatory myopathy, myopathy from diabetes, myopathy from pulmonary hypertension, myopathies that develop during chronic heart failure, in particular the subtypes heart failure with reduced ejection fraction (HFrEF) and heart failure with preserved ejection fraction (HFpEF), myopathy from kidney failure and myopathy from tumor cachexia.

The link between an increased MuRF1 expression and myopathy from pulmonary hypertension is for example described in de Man et al., Am. J. Respir. Crit. Care Med., 2011 May 15, 183(10), 1411-1418.

The link between an increased MuRF1 expression and chronic heart failure and/or kidney failure myopathy promoted by angiotension II, is for example described in du Bois et al., Circ. Res., 2015 Aug. 14, 117(5), 424-436.

Likewise, Bowen et al., Eur. J. Heart. Fail., 2015 Mar. 17(3), 263-272, describe the connection between an increased MuRF1 expression and myopathy developed during diastolic heart failure (HFpEF).

Upregulation of MuRF1 has been reported in chronic kidney failure patients, and this to correlate closely with muscle atrophy (J. Aniort et al., J. Cachexia Sarcopenia Muscle, 2019, 10(2), 323-337; S. H. Lecker et al., J. Am. Soc. Nephrol., 2011, 22(5), 821-824). Compounds that downregulate MuRF1 are therefore predicted to protect skeletal muscles during chronic kidney failure. The concept of kidney injury and muscle atrophy has also been further validated in an animal model using acute gentamycin induced kidney damage (J. Aniort et al., Int. J. Biochem. Cell Biol., 2016, 79, 505-516).

MuRF1 is upregulated during ageing in skeletal muscles (O. Rom et al., Free Radic. Biol. Med. 2016, 98, 218-230). This is associated with mitochondrial dysfunction, supposed to contribute to sarcopenia (loss of myofibrils) and cardiomypathy (H. W. Liu et al., Biogerontology. 2020, 21(3), 367-380). Rescue from mitochondrial dysfunction rescues in a mouse model from cardiomyopathy (Y. A. Chiao et al., eLife, 2020, 9, 55513). Accordingly, compounds that improve mitochondrial functions and downregulate MuRF1 are predicted to protect from age-associated sarcopenia and cardiomyopathy.

Stress on the diaphragm by mechanical ventilation (H. W. van Hees et al., Am. J. Physiol. Lung Cell Mol. Physiol., 2008, 294(6), L1260-8) or congestive heart failure P. E. Hooijman et al., Am. J. Respir. Crit. Care Med., 2015, 191(10), 1126-1138) activates the ubiquitin and proteasome system, including MuRF1 (van Hees, Loc. cit; Hoojiman, Loc. cit.). That this is not merely a correlative finding is underpinned by the finding that inhibition of the proteasome system by bortezomid (van Hees, Loc. cit), or removal of MuRF1 by using a knock-out model (Hoojiman, Loc. cit.) protects from diaphragm weakness (Hoojiman, Loc. cit.). Therefore, the compounds described here are predicted to protect the diaphragm contractile force in congestive heart failure and in critical illness (van Hees, Loc. cit; Hoojiman, Loc. cit.).

Genetic muscular atrophies are associated with a marked loss of muscle tissues and loss of muscle strength. The upregulation of MuRF1 has mechanistically been implicated in this (J. Shin et al., Int. J. Biochem. Cell Biol., 2013, 45(10), 2266-2279). As a specific example for this nemaline myopathy may be mentioned, where the upregulation of MuRF1 on the fiber level in glycolytically active muscle fibers closely correlates with those fibers and tissues that become most atrophic (F. Li et al., Hum. Mol. Genet., 2015, 24(18), 5219-5233).

Many types of metabolic stress states including diabetes have been shown to activate MuRF1 expression (S. H. Lecker et al., FASEB J. 2004, 18(1), 39-51). In an animal model for diabetes (i.e. streptotozin-induced diabetes in mice), this has been shown to activate the Foxo-MuRF1 signaling axis, and this in turn closely correlates with muscle wasting (B. T. O'Neill et al., Diabetes, 2019, 68(3), 556-570).

Severe obesity is accompanied by changes in circulating factors (e.g. insulin and amino acids) that influence skeletal protein synthesis and degradation (C. S. Katsanos et al., Obesity, 2011, 19, 469-475). Insulin resistance accelerates muscle protein degradation by activation of the Ubiquitin-Proteasome pathway (X. Wang, Endocrinology, 147(9), 4160-4168). Former studies revealed that up to 30% of weight loss may be due to reduction of muscle mass using different modalities of dieting in obesity (D. L. Ballor et al., Int. J. Obes. Relat. Metab. Disord., 1994, 18, 35-40).

Therefore, a preferred embodiment of the present invention relates to compounds of formula I, as defined above, for use in the treatment or prophylaxis of critical illness myopathy, nemaline myopathy, inflammatory myopathy, myopathy from diabetes, myopathy from pulmonary hypertension, myopathy from chronic heart failure (in particular the subtypes HFrEF and HFpEF), myopathy from kidney failure, myopathy from tumor cachexia, diaphragm weakness due to stress on the diaphragm by mechanical ventilation or by congestive heart failure, congenital myopathy, in particular congenetic muscle atrophy; age-associated sarcopenia and cardiomyopathy.

The present invention in particular relates to:

The compounds of the general formula I, as defined above, for use in the treatment or prophylaxis of critical illness myopathy.

The compounds of the general formula I, as defined above, for use in the treatment or prophylaxis of nemaline myopathy.

The compounds of the general formula I, as defined above, for use in the treatment or prophylaxis of inflammatory myopathy.

The compounds of the general formula I, as defined above, for use in the treatment or prophylaxis of myopathy from diabetes.

The compounds of the general formula I, as defined above, for use in the treatment or prophylaxis of myopathy from pulmonary hypertension.

The compounds of the general formula I, as defined above, for use in the treatment or prophylaxis of myopathy from chronic heart failure, in particular the subtypes HFrEF and HFpEF.

The compounds of the general formula I, as defined above, for use in the treatment or prophylaxis of myopathy from kidney failure.

The compounds of the general formula I, as defined above, for use in the treatment or prophylaxis of myopathy from tumor cachexia.

The compounds of the general formula I, as defined above, for use in the treatment or prophylaxis of diaphragm weakness due to stress on the diaphragm by mechanical ventilation or by congestive heart failure.

The compounds of the general formula I, as defined above, for use in the treatment or prophylaxis of congenital myopathy, in particular congenetic muscle atrophy.

The compounds of the general formula I, as defined above, for use in the treatment or prophylaxis of age-associated sarcopenia.

The compounds of the general formula I, as defined above, for use in the treatment or prophylaxis of age-associated cardiomyopathy.

The compounds of the general formula I, as defined above, for use in the treatment or prophylaxis of diabetes.

It has moreover been found that, independently from their action on muscle conditions, the compounds I and their salts have a beneficial effect in cardiac conditions associated with systolic or diastolic dysfunction. The present invention therefore also relates to the compounds I and their salts for use in the treatment or prophylaxis of cardiac conditions associated with systolic or diastolic dysfunction.

The present invention further relates to a pharmaceutical composition (i.e. medicaments) comprising at least one compound selected from compounds of the general formula I, as defined above, or at least one pharmaceutically acceptable salt thereof and at least one pharmaceutically acceptable carrier.

These pharmaceutically acceptable carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above conditions or diseases.

In the pharmaceutical compositions, the at least one compound of the present invention may be formulated alone or together with further active compounds, in suitable dosage unit formulations containing conventional carriers, which generally are non-toxic and/or pharmaceutically acceptable. The carriers can be solid, semisolid or liquid materials which serve as vehicles, carriers or medium for the active compound. Suitable carriers are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutically acceptable carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols.

Parenteral administration is effected by using aqueous suspensions, isotonic salt solutions or sterile and injectable solutions which comprise pharmacologically suitable dispersants and/or wetting agents, for example propylene glycol or polyethylene glycol.

The active ingredient may also be formulated as microcapsules or liposomes/centrosomes, if suitable with one or more carriers or additives.

In addition to the compounds of the general formula I, and the pharmaceutically acceptable salts thereof, the compositions of the invention may comprise further active ingredients which may be beneficial for the treatment of the impairments or diseases indicated above.

The present invention thus further relates to pharmaceutical compositions in which a plurality of active ingredients are present together, where at least one thereof is a compound of the invention.

When producing the pharmaceutical compositions, the compounds according to the invention are optionally mixed or diluted with one or more pharmaceutically acceptable carriers.

The present invention further relates to the use of compounds selected from compounds of the general formula I, as defined above, or pharmaceutically acceptable salts thereof for the manufacture of a medicament for the treatment or prophylaxis of the conditions defined above, such as muscle-wasting conditions, as defined above, or conditions, in particular myopathies, which are associated with an increased Muscle RING Finger 1 (MuRF1) expression, as defined above, or cardiac conditions associated with systolic or diastolic dysfunction, or diabetes.

Regarding the manufacture of said medicaments, reference is made to the statements given in connection with the above described pharmaceutical compositions.

The present invention also relates to a method for treating or preventing the conditions defined above, such as a muscle wasting condition or condition, in particular myopathies, which are associated with an increased Muscle RING Finger 1 (MuRF1) expression, as defined above, or cardiac conditions associated with systolic or diastolic dysfunction, or diabetes, said method comprising the step of administering a therapeutically effective amount of a compound selected from compounds of the general formula I or a pharmaceutically acceptable salts thereof to a subject in need thereof.

Likewise the present invention relates to a method for protecting or enhancing the diaphragm contractility during stress states, such as long term mechanical ventilation, surgery, chronic heart failure or primary muscular diseases, said method comprising the step of administering a therapeutically effective amount of a compound selected from compounds of the general formula I or a pharmaceutically acceptable salts thereof to a subject in need thereof.

The present invention in particular relates to:
A method for treating or preventing skeletal or cardiac muscle atrophy and/or diaphragm weakness resulting from congestive heart failure;
A method for treating or preventing skeletal or cardiac muscle atrophy resulting from chronic heart failure;
A method for treating or preventing skeletal or cardiac muscle atrophy resulting from cancer;
A method for treating or preventing skeletal or cardiac muscle atrophy resulting from cancer treatment with myotoxic and/or cardiotoxic substances, such as doxorubicin;
A method for treating or preventing skeletal or cardiac muscle atrophy resulting from congenital myopathy;
A method for treating or preventing skeletal or cardiac muscle atrophy resulting from AIDS;
A method for treating or preventing skeletal or cardiac muscle atrophy resulting from chronic obstructive pulmonary disease (COPD);
A method for treating or preventing skeletal or cardiac muscle atrophy resulting from chronic renal disease;
A method for treating or preventing skeletal or cardiac muscle atrophy resulting from renal failure;
A method for treating or preventing skeletal or cardiac muscle atrophy resulting from diabetes;
A method for treating or preventing skeletal or cardiac muscle atrophy resulting from severe burns;
A method for treating or preventing skeletal or cardiac muscle atrophy resulting from sarcopenia during aging;
A method for treating or preventing skeletal or cardiac muscle atrophy resulting from reduction in blood supply;
A method for treating or preventing skeletal or cardiac muscle atrophy resulting from temporary or long term immobilization;
A method for treating or preventing skeletal or cardiac muscle atrophy and/or diaphragm weakness resulting from long term mechanical ventilation;
A method for treating or preventing skeletal or cardiac muscle atrophy resulting from denervation.
A method for treating or preventing skeletal or cardiac muscle atrophy resulting from prolonged weightlessness;
A method for treating or preventing skeletal or cardiac muscle atrophy resulting from malnutrition;
A method for treating or preventing diabetes;
A method for treating or preventing cardiac conditions associated with systolic or diastolic dysfunction;
said methods comprising the step of administering a therapeutically effective amount of a compound selected from compounds of the general formula I or a pharmaceutically acceptable salts thereof to a subject in need thereof.

The present invention in particular further relates to:
A method for treating or preventing critical illness myopathy, including protection of the diaphragm contractility and function during intensive care;
A method for treating or preventing nemaline myopathy;
A method for treating or preventing inflammatory myopathy;
A method for treating or preventing myopathy from diabetes;
A method for treating or preventing myopathy from pulmonary hypertension;
A method for treating or preventing myopathy from chronic heart failure, in particular the subtypes HFrEF and HFpEF;
A method for treating or preventing myopathy from kidney failure;
A method for treating or preventing myopathy from tumor cachexia;
said methods comprising the step of administering a therapeutically effective amount of a compound selected from compounds of the general formula I or a pharmaceutically acceptable salts thereof to a subject in need thereof.

The present invention specifically relates to:
A method for treating or preventing skeletal or cardiac muscle atrophy resulting from or associated with heart failure with reduced ejection fraction (HF-rEF).
A method for treating or preventing skeletal or cardiac muscle atrophy resulting from or associated with heart failure with preserved ejection fraction (HF-pEF).
A method for treating or preventing skeletal or cardiac muscle atrophy resulting from or associated with hypertension.
A method for treating or preventing skeletal or cardiac muscle atrophy resulting from or associated with tumor cachexia.
A method for treating or preventing muscle atrophy and/or cardiac toxicity induced by Doxorubicin.
A method for treating or preventing sarcopenia and/or cardiomyopathy due to aging.

A method for treating or preventing muscle atrophy due to chronic renal disease.

A method for treating or preventing diaphragm weakness due to mechanical ventilation or congestive heart failure.

A method for treating or preventing congenital myopathy, in particular congenetic muscle atrophy.

A method for treating or preventing diabetes-induced muscle atrophy.

A method for treating or preventing diabetes.

A method for treating or preventing cardiac conditions associated with systolic or diastolic dysfunction.

The term "subject in need thereof", as used herein, refers to a subject, which suffers from one or more of the aforementioned conditions or diseases or refers to a subject, which is likely to develop one or more of the aforementioned conditions or diseases. Preferably, the term "subject in need thereof", refers to a mammal, in particular a human being, productive animal or domestic animal. In particular, the term "subject in need thereof", refers to a human being.

The terms "effective amount" and "therapeutically effective amount", as used herein, mean the amount of the subject compound that will elicit the biological or medical response of a tissue, system, animal or human that is being sought by the researcher, veterinarian, medical doctor or other clinician. It is recognized that one skilled in the art may affect the muscle wasting conditions and/or myopathies by treating a patient presently afflicted with these disorders or by prophylactically treating a patient afflicted with these disorders with an effective amount of the compound of the present invention.

The terms "treatment" and "treating", as used herein in connection with the methods as described above, refer to all processes, wherein there may be a slowing, interrupting, arresting, controlling, or stopping of the progression of the muscle wasting conditions and/or myopathies, as described herein, but does not necessarily indicate a total elimination of all symptoms of these conditions or disorders, as well as the prophylactic therapy of the mentioned conditions, particularly in a patient who is predisposed to such conditions or disorders.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By "pharmaceutically acceptable" it is meant the carrier, diluent or excipient must be compatible with the other ingredients of the formulation and not deleterious to the recipient thereof.

The terms "administration of a compound" and/or "administering a compound" should be understood to mean providing a compound of the invention or a prodrug of a compound of the invention to the individual in need of treatment.

In the treatment and/or prophylaxis of the above described muscle wasting conditions and myopathies, which are associated with an increased MuRF1 expression, an appropriate dosage level will generally be about 2 to 500 mg per day per kg body weight of the subject in need thereof, which can be administered in single or multiple doses. Preferably, the dosage level will be about 5 to about 250 mg/kg per day.

For oral administration, the compositions are preferably provided in the form of tablets containing 10 to 5000 milligrams of the active ingredient, particularly 50.0, 100.0, 200.0, 500.0, 1000.0, 2000.0, 3000.0, 4000.0 and 5000.0 milligrams of the active ingredient for the symptomatic adjustment of the dosage to the subject in need thereof.

This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the treatment and/or prophylaxis of the aforementioned diseases and conditions in combination with other agents.

The compounds of the present invention may be used in combination with one or more other drugs in the treatment and/or prophylaxis of the aforementioned diseases and conditions for which compounds of formula I or the other drugs may have utility, where the combination of the drugs together are safer or more effective than either drug alone. Such other drug(s) may be administered, by a route and in an amount commonly used therefore, contemporaneously or sequentially with a compound of formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. The above combinations include combinations of a compound of the present invention not only with one other active compound, but also with two or more other active compounds.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The following examples and figures are intended for further illustration of the present invention.

Abbreviations:
- ALPHA Amplified Luminescent Proximity Homogeneous Assay;
- DSF Differential Scanning Fluorimetry;
- GST Glutathion-S-transferase;
- UBE1 Recombinant Human His6-Ubiquitin Activating Enzyme;
- DMSO Dimethylsulfoxide;
- CDI 1,1'-Carbonyldiimidazol;
- DMEM Dulbecco's Modified Eagle's Medium;
- Sham saline-treated;
- DEX dexamethasone;
- PBS phosphate buffered saline;
- MCT monocrotaline;
- TA tibialis anterior;
- TL tibia length;
- EDL extensor digitorum longus;
- CSA cross-sectional area;
- LAD ligation of the left anterior dexterior coronary artery;
- MI Myocardial infarction;
- WB western blot;
- BW body weight;
- CHF chronic heart failure;
- LV left ventricle;
- LVEDD left ventricular end-diastolic diameter;
- LVEF left ventricular ejection fraction;
- LVESD left ventricular end-systolic diameter;
- LVFS left ventricular fractional shortening;
- MRPS-5 mitochondrial ribosomal protein 5;
- Nox 2 NADPH oxidase 2;
- CS Citrate synthase;
- SDH Succinate dehydrogenase;
- TOM-20 Translocase of outer mitochondrial membrane 20;
- GAPDH Glyceraldehyde 3-phosphate dehydrogenase;
- AU arbitrary unit;
- HPRT hypoxanthin-phosphoribosyl-transferase;
- FRET Fluorescence Resonance Energy Transfer;
- MAFbx Muscle atrophy F-box;
- CARP Cardiac adriamycin-responsive protein;
- GAPDH Glyceraldehyde 3-phosphate dehydrogenase;
- eIF2B-delta Translation initiation factor eIF-2B subunit delta;
- AS3MT Arsenite methyltransferase;
- ATPAF1 ATP synthase mitochondrial F1 complex assembly factor 1;
- GHDC GH3 domain-containing protein;
- BAX Apoptosis regulator BAX.

FIGURES

FIG. 1: Cytotoxicity test results based on the release of lactate dehydrogenase (LDH) activity in cultured myoblasts in the presence of increasing concentrations of the compounds MyoMed-946, MyoMed-946-5, MyoMed-946-8.

Figure 2:
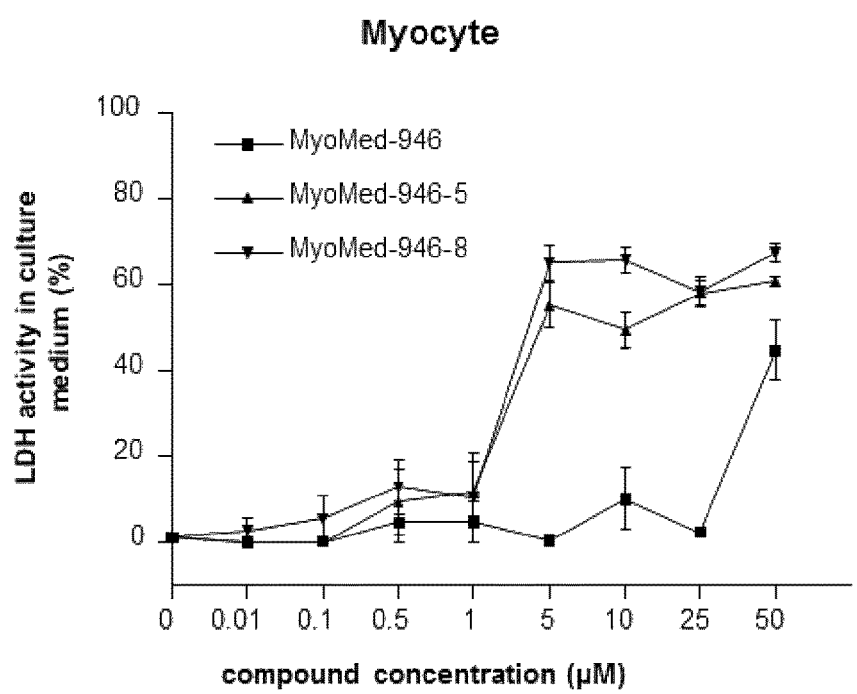

FIG. 2: Cytotoxicity test results based on the release of lactate dehydrogenase (LDH) activity in cultured myocytes in the presence of increasing concentrations of the compounds MyoMed-946, MyoMed-946-5, MyoMed-946-8.

FIGS. 3 to 7: Physical characteristics of sham (n=20) and mice treated with monocrotaline fed either normal chow (MCT; n=27) or the MyoMed-946 compound (MCT+MyoMed-946; n=27). The data confirm that MCT treatment induced cardiac cachexia independent of the chow administrated, as demonstrated by an impaired weight gain (FIG. 3), increased pulmonary congestion (FIG. 4) and increased heart weight over body weight (BW) (FIG. 5), and that right ventricular (RV) hypertrophy (FIG. 6), the latter visualized by representative H&E stained medial cross sections of the heart (FIG. 7), is attenuated. *P<0.01 vs. Sham.

FIGS. 8 to 12: Skeletal muscle wet-weights (normalized to tibia length; TL) for the extensor digitorum longus (EDL) (FIG. 8), soleus (FIG. 9), tibialis anterior (TA) (FIG. 10) for MCT-treated mice in the absence or in the presence of the MuRF1 inhibitor MyoMed-946. In addition the fiber cross sectional area (CSA) for the TA muscle is also presented (FIG. 11), the latter visualized by representative H&E stain (FIG. 12). *P<0.05 vs. sham; § P<0.01 vs. sham and MCT+MyoMed-946.

Figure 13:
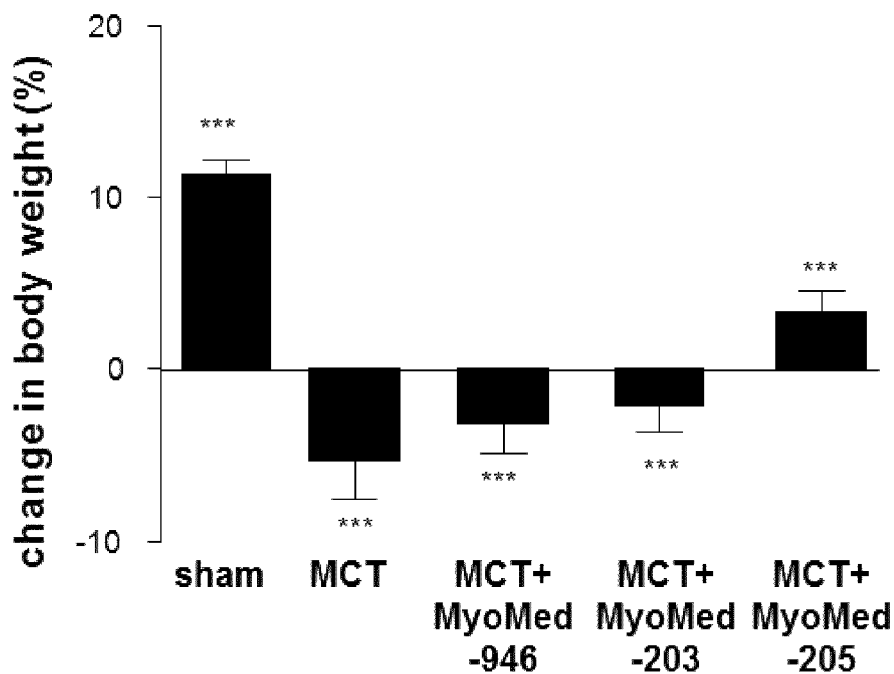
Figure 14:
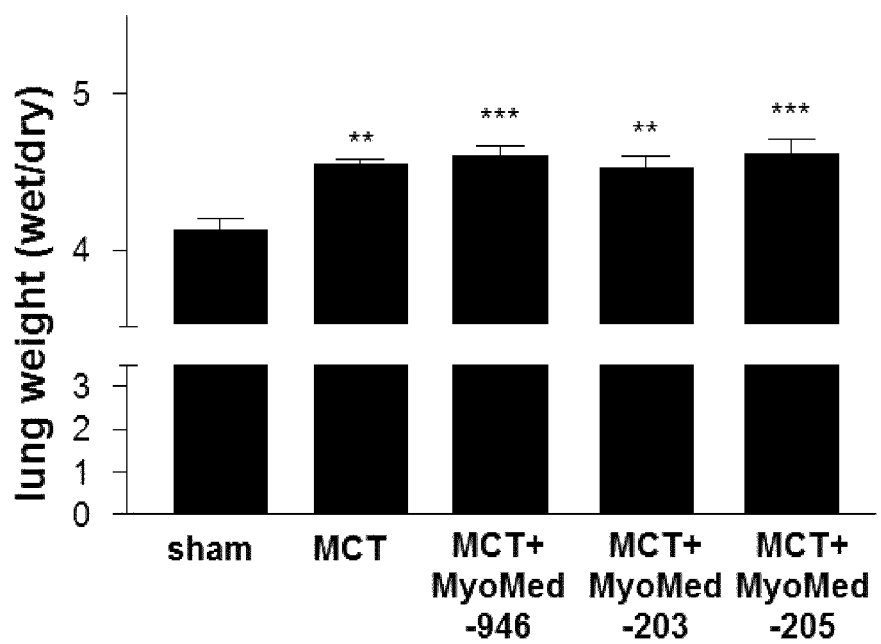
Figure 15:
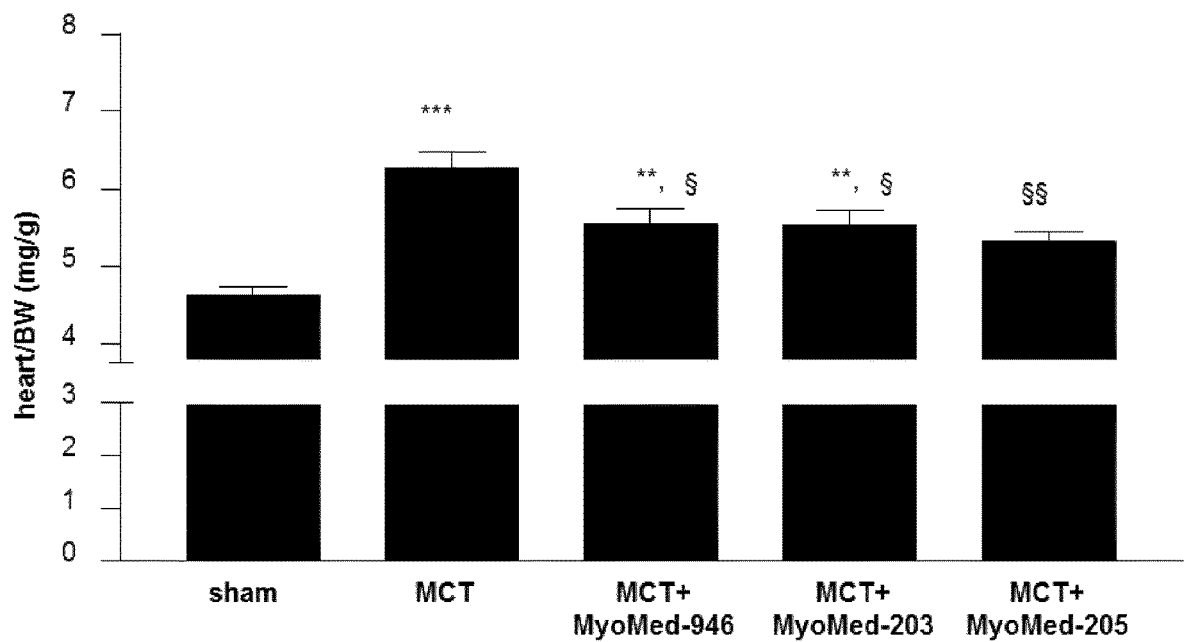
Figure 16:
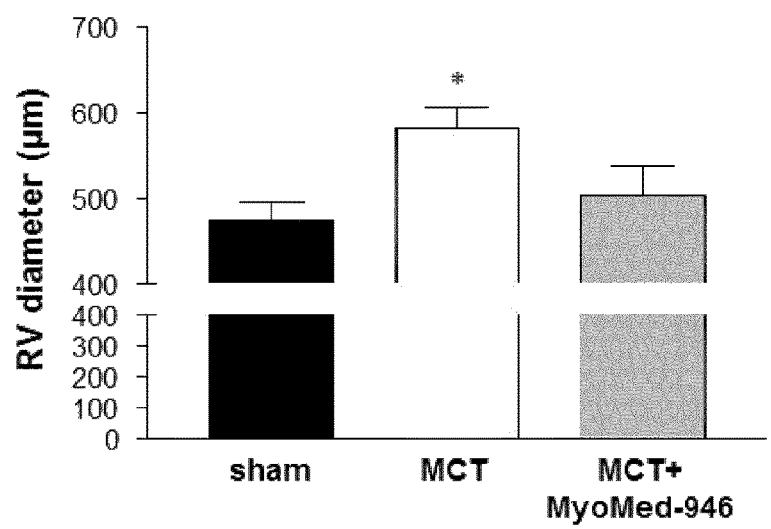
Figure 17:
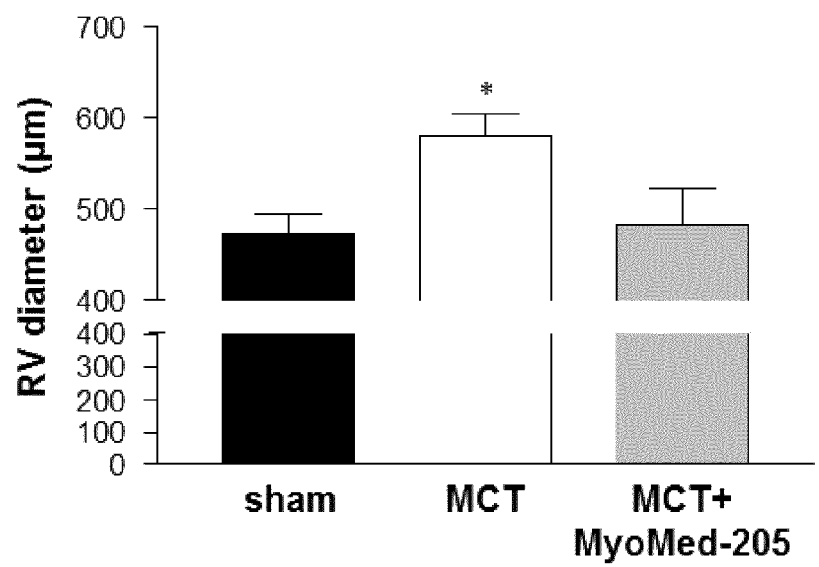
Figure 18:
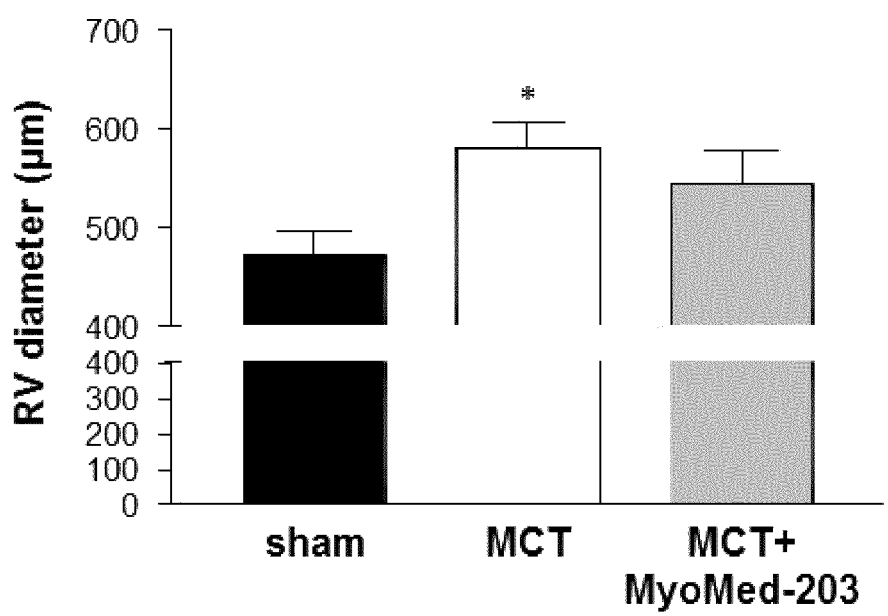

FIGS. 13 to 18: Physical characteristics of sham (n=10) and mice treated with monocrotaline fed either normal chow (MCT; n=10) or the MuRF1 inhibitors MyoMed-946 (MCT+MyoMed-946; n=10), MyoMed-203 (MCT+MyoMed-203; n=10) and MyoMed-205 (MCT+MyoMed-205; n=10). Data are presented as mean±standard error of the mean. FIG. 13: *p<0.001 vs. begin; FIG. 14: *p<0.001 vs. sham p<0.01 vs. sham; FIG. 15: *p<0.001, **p<001 vs. sham, §§ p<0.01, § p<0.05 vs. MCT; FIGS. 16 to 18: *P<0.01 vs. Sham. The data confirm that MCT treatment induced cardiac cachexia independent of the chow administrated, as demonstrated by an impaired weight gain (FIG. 13), increased pulmonary congestion (FIG. 14) and increased heart weight over body weight (BW) (FIG. 15), and that right ventricular (RV) hypertrophy is attenuated by the MuRF1 inhibitors MyoMed-946, MyoMed-203 and MyoMed-205 (FIGS. 16 to 18).

Figure 19:
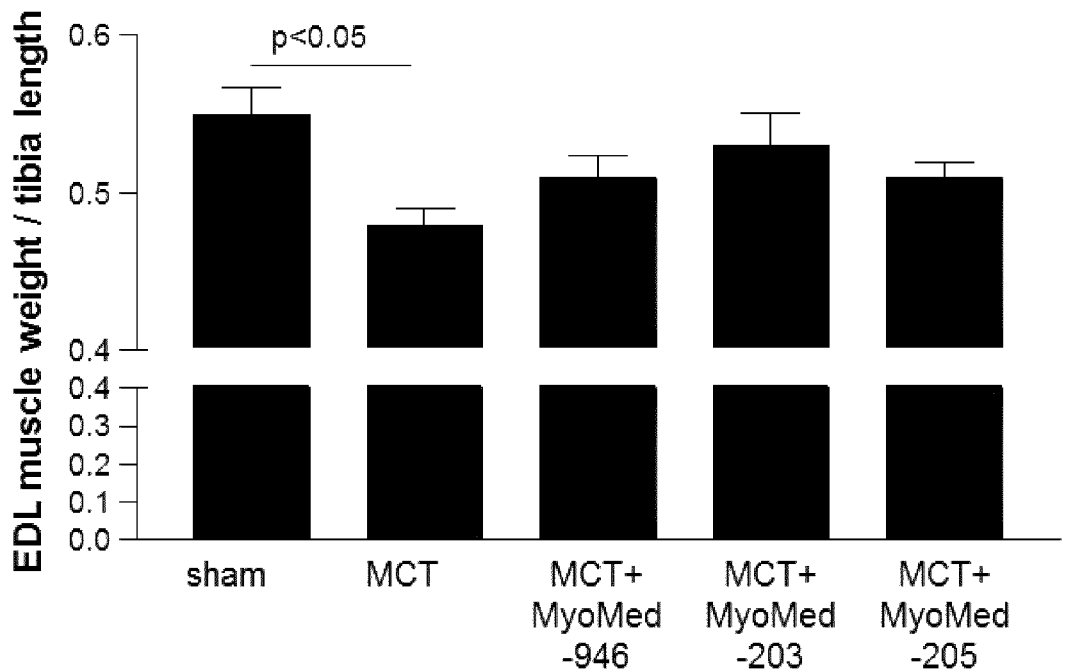
Figure 20:
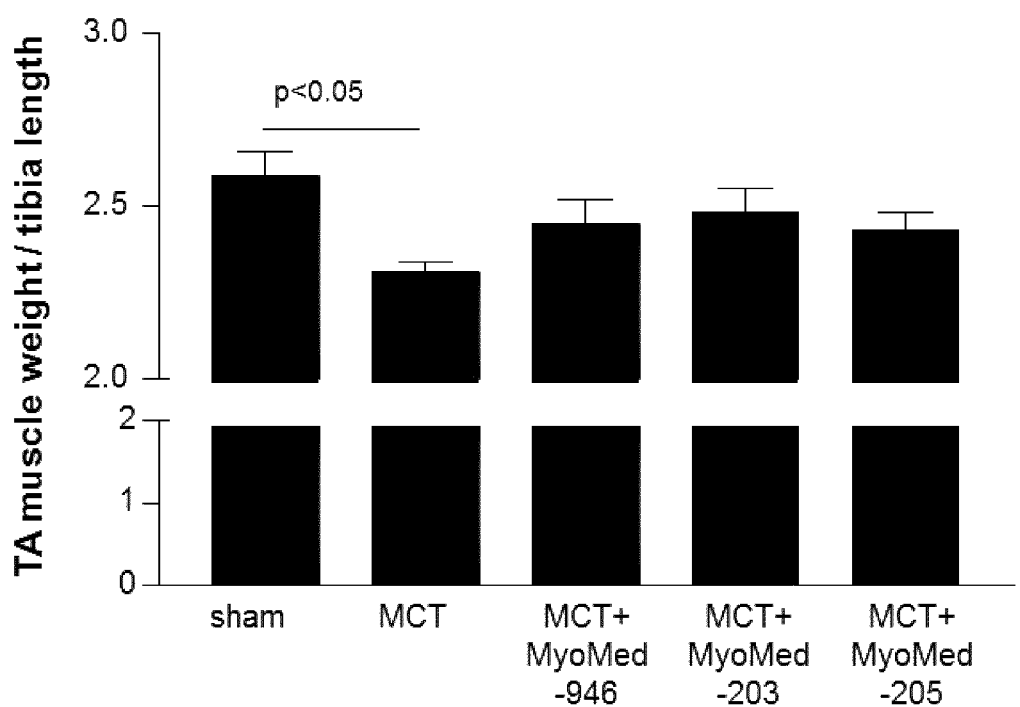

FIGS. 19 and 20: Skeletal muscle wet-weights (normalized to tibia length; TL) for the extensor digitorum longus (EDL) (FIG. 19) and tibialis anterior (TA) (FIG. 20) for MCT-treated mice in the absence (Sham) or in the presence of the MuRF1 inhibitors MyoMed-946, MyoMed-203 and MyoMed-205.

Figure 21:
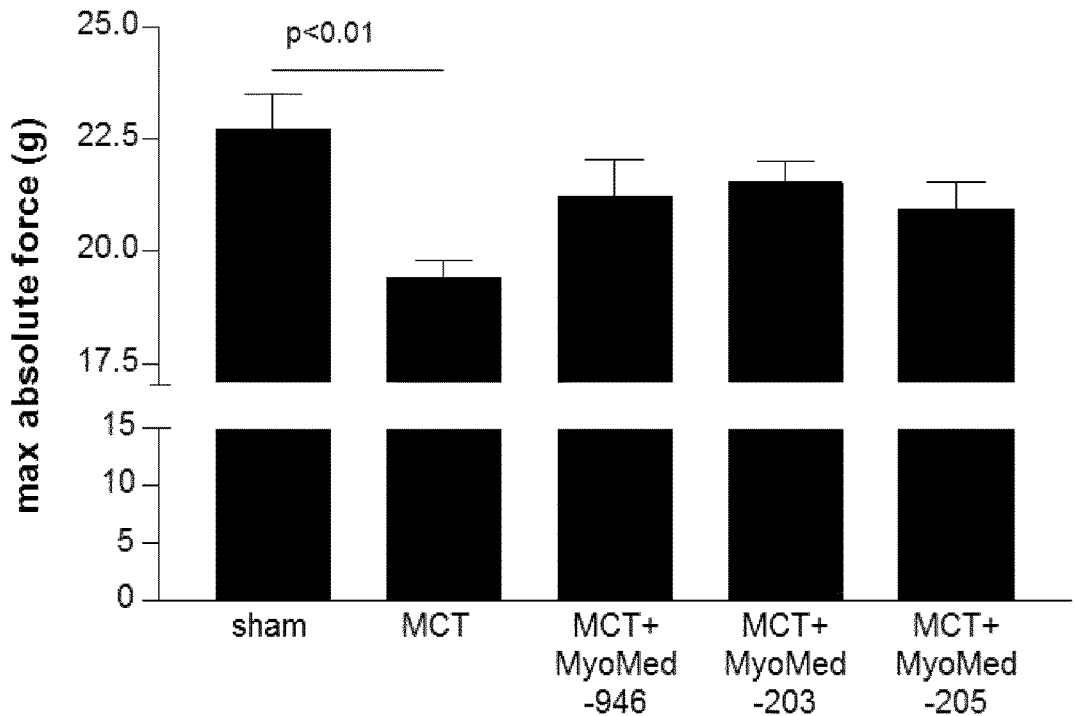

FIG. 21: Diaphragm maximum force for MCT-treated mice in the absence (Sham) or in the presence of the MuRF1 inhibitors MyoMed-946, MyoMed-203 and MyoMed-205.

Figure 22:
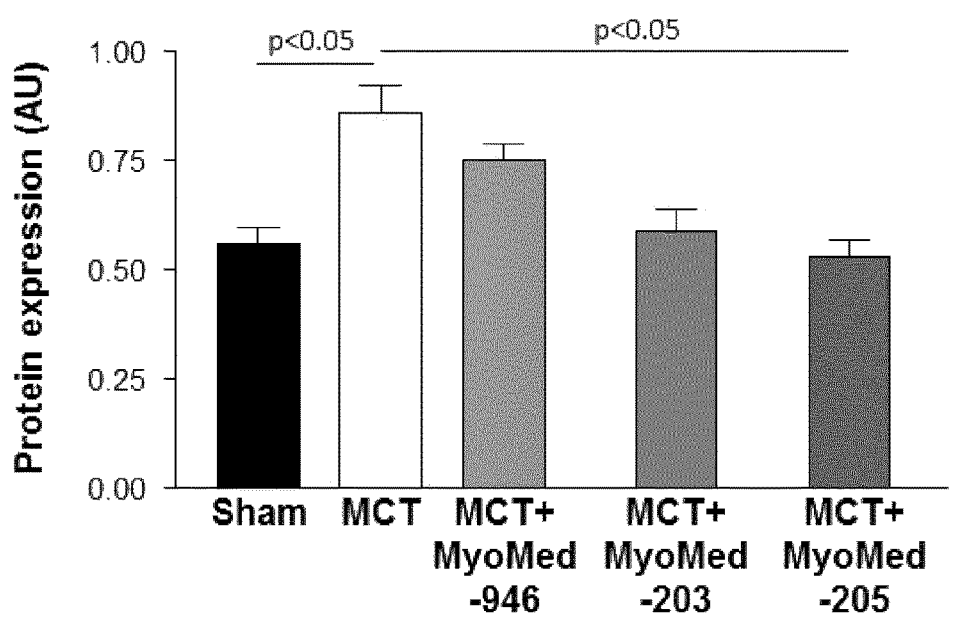
Figure 23:
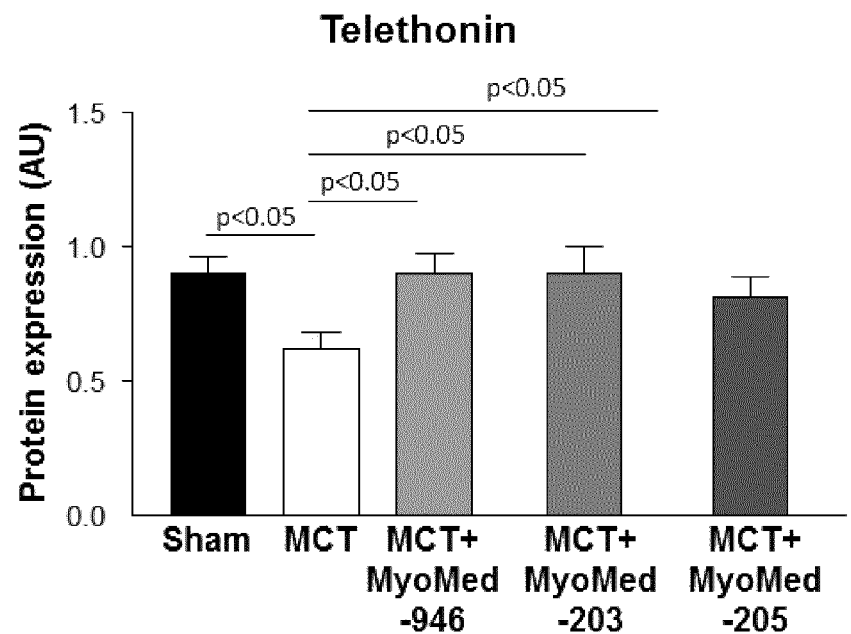
Figure 24:
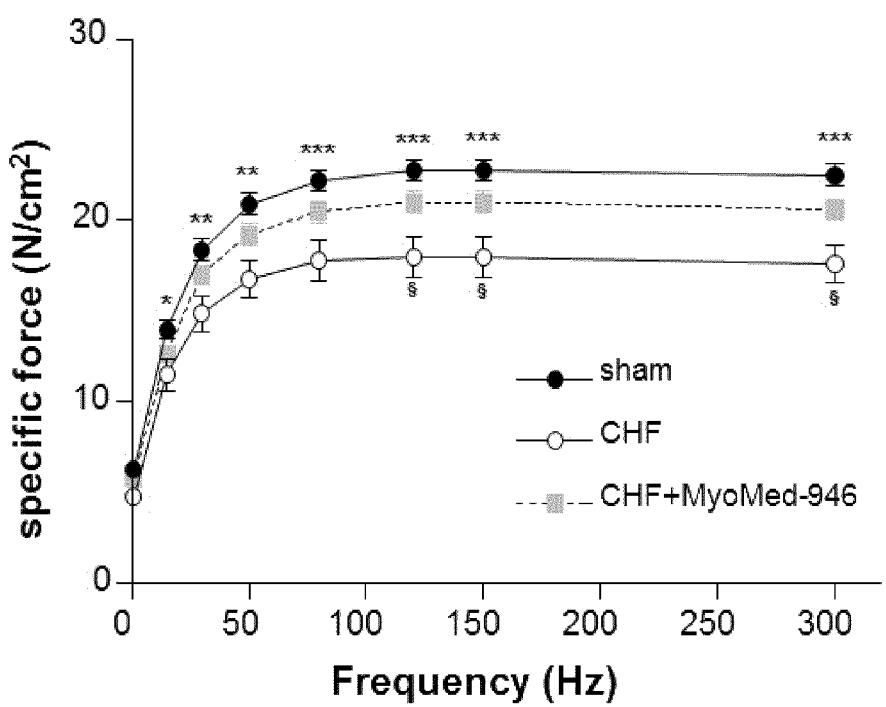
Figure 25:
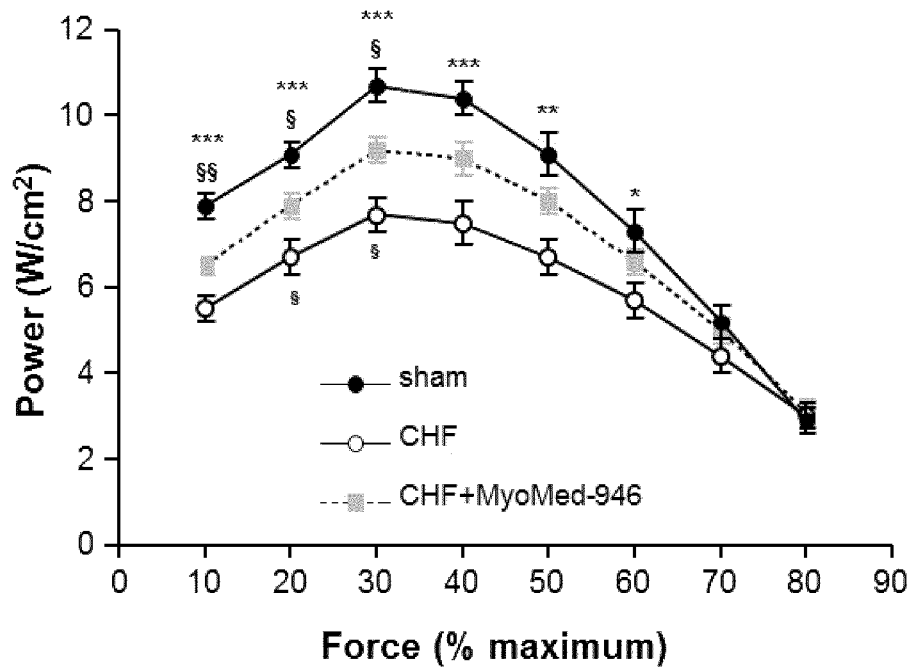
Figure 26:
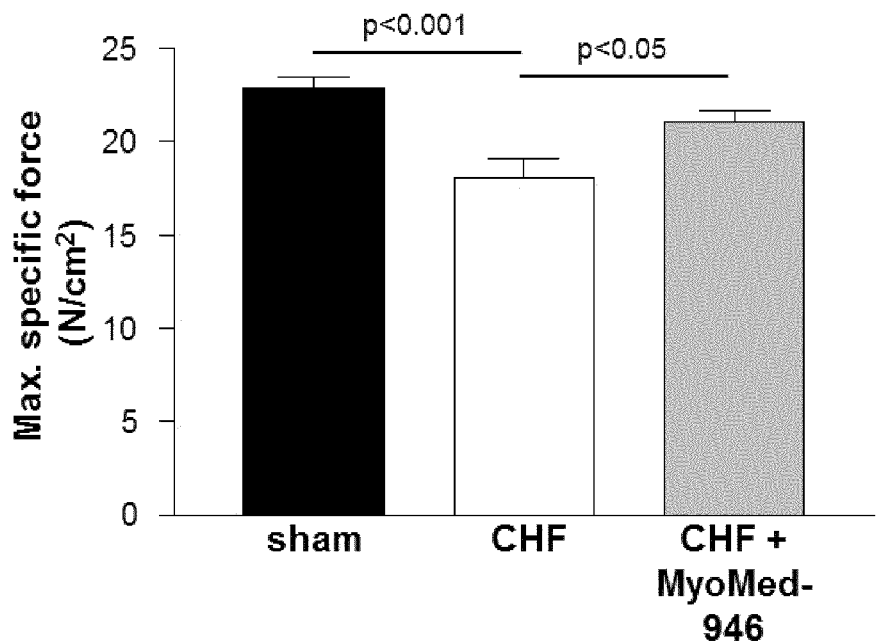

FIGS. 22 and 23: Expression of MuRF1 (FIG. 22) and telethonin (FIG. 23) in the tibialis anterior muscle tissue of MTC-treated mice, in the absence (Sham) or in the presence of the MuRF1 inhibitors MyoMed-946, MyoMed-203 and MyoMed-205.

FIGS. 24 to 27: Diaphragm function, assessed during isometric contractions (FIG. 24) and also isotonic contractions (FIG. 25) of diaphragm myofiber bundles from mice suffering from chronic heart failure (CHF) with reduced ejection fraction (HFrEF) following myocardial infarction (MI), whereby diaphragm maximum force (FIG. 26) and diaphragm peak power (FIG. 27) were determined. Data are presented as mean±standard error of the mean. *P<0.05, P<0.01, *P<0.001 vs. CHF, § P<0.05, and §§ P<0.01 vs. CHF+MyoMed-946.

Figure 28:
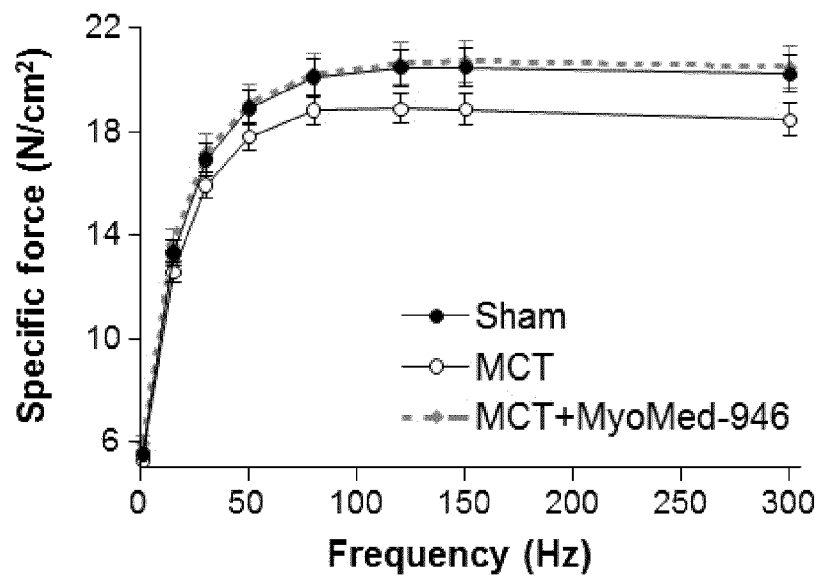
Figure 29:
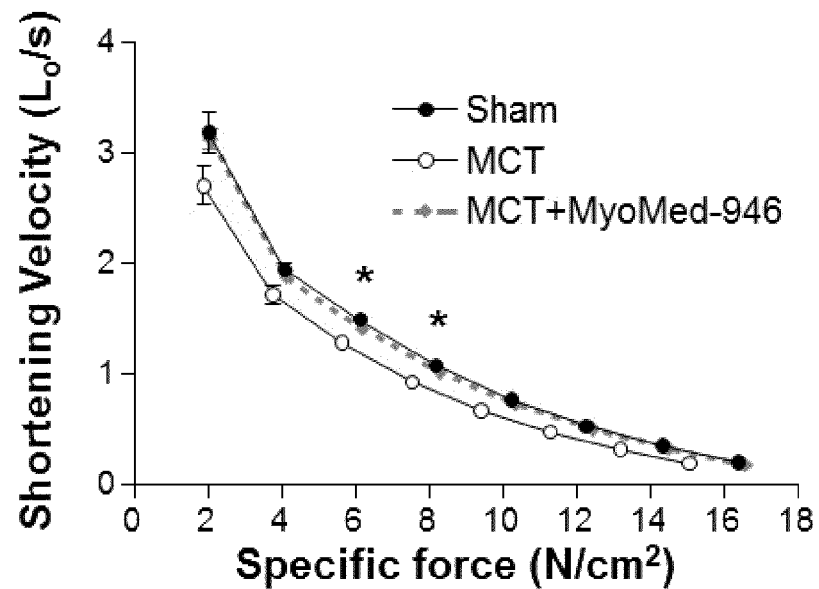
Figure 30:
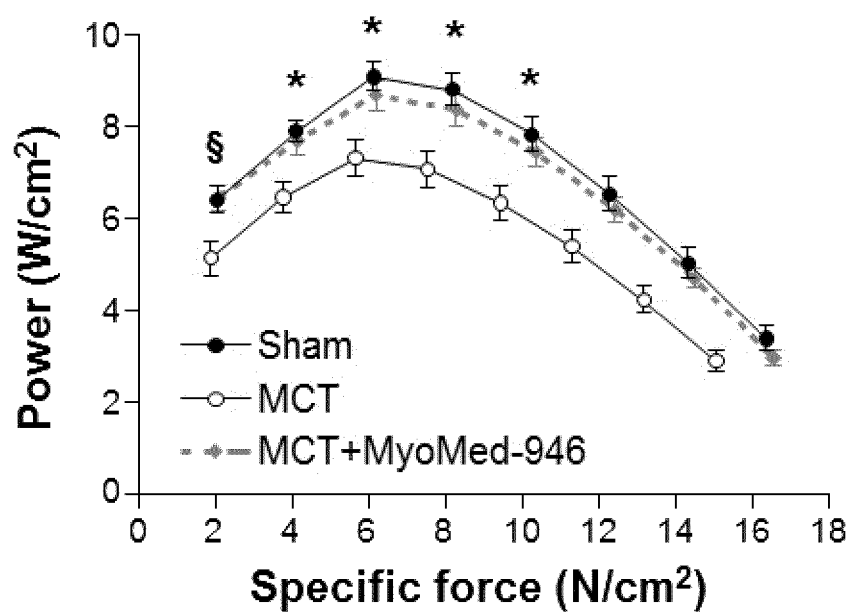

FIGS. 28 to 30: In vitro skeletal muscle contractile function, assessed during isometric contractions (FIG. 28) and also isotonic contractions, whereby shortening velocity (FIG. 29) and power (FIG. 30) were determined. MCT treated mice demonstrates impairments in shortening velocity and power by around 20% compared to shams. These impairments are essentially prevented in MCT mice fed the MyoMed-946 compound. *P<0.05 vs sham; § P<0.01 vs. sham and MCT+MyoMed-946.

Figure 31:
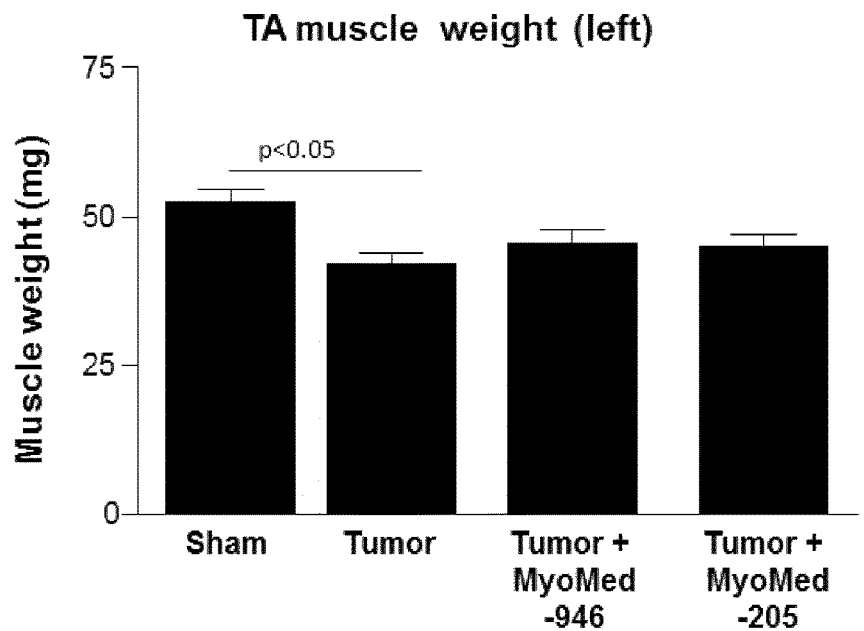

FIG. 31: Muscle wet-weights of the tibialis anterior (TA) in B16F10 cell inoculated mice receiving regular chow (tumor) and B16F10 cell inoculated mice fed with the compounds MyoMed-946 (tumor+MyoMed-946) and MyoMed-205 (tumor+MyoMed-205).

Figure 32:
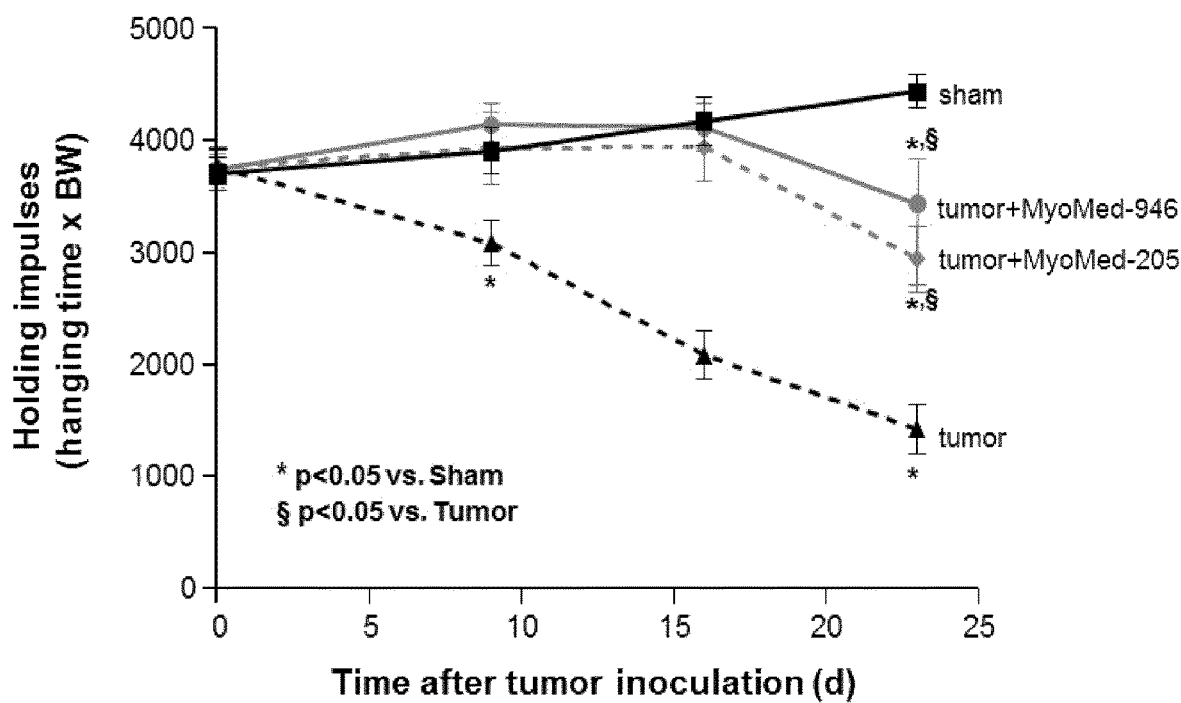

FIG. 32: Wire-hang test of B16F10 cell inoculated mice (melanoma tumor cell model), 9 d, 16 d and 23 d after inoculation. Tumor growth leads to a significant reduction in muscle function (tumor group) compared to mice of the control group (sham). This reduction of muscle function is attenuated in mice fed with the compounds MyoMed-946 (tumor+MyoMed-946) and MyoMed-205 (tumor+MyoMed-205).

Figure 33:
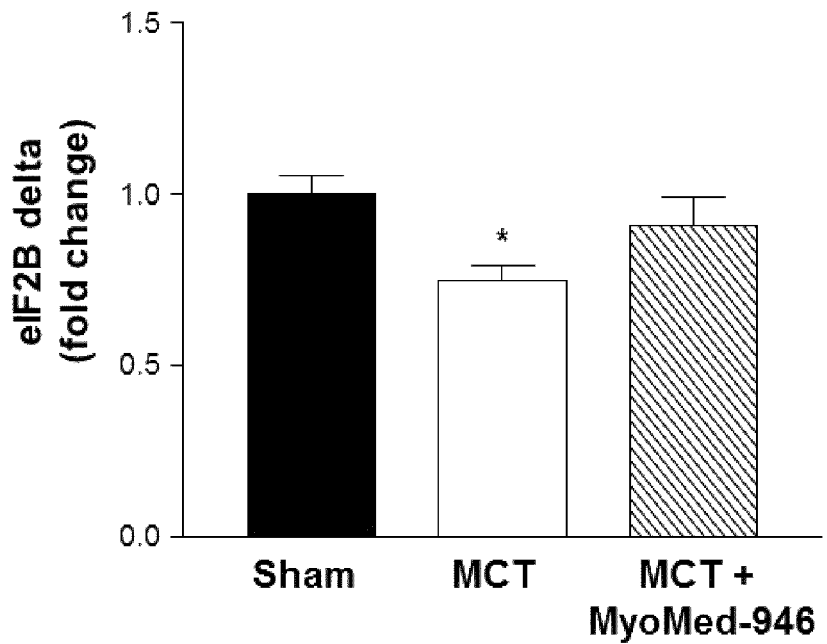
Figure 34:
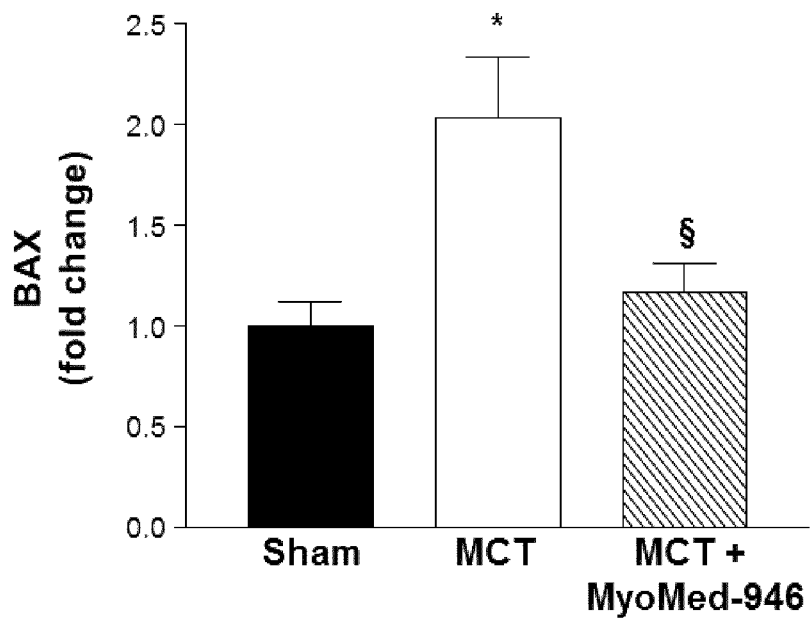
Figure 35:
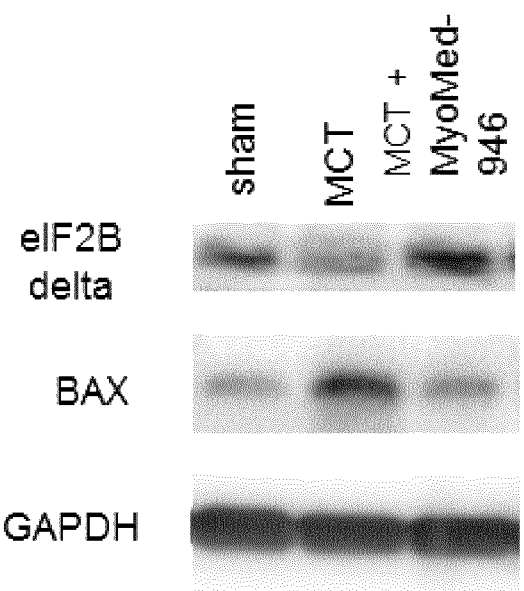

FIG. 33 to 35: Expression levels of eIF2B subunit-delta (FIG. 33) and BAX (FIG. 34) for sham, MCT, and MCT+MyoMed-946 mice, determined by western blot analysis, with representative blots (FIG. 35). *P<0.05 vs sham; § P<0.01 vs. MCT.

Figure 36:
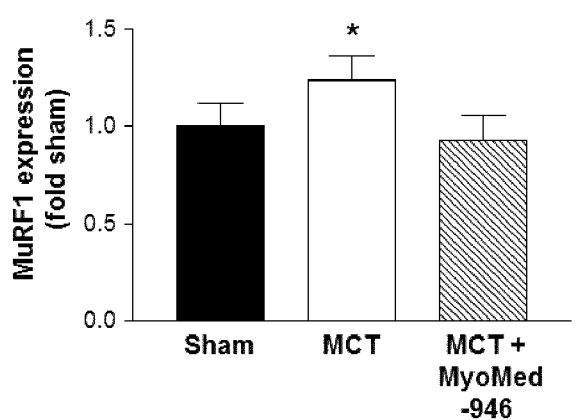
Figure 36:
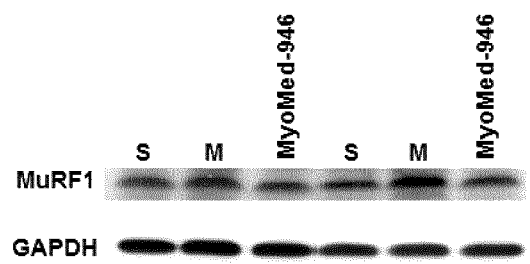
Figure 37:
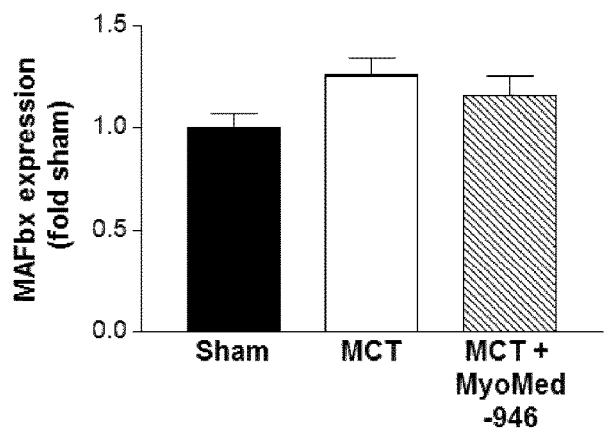
Figure 37:
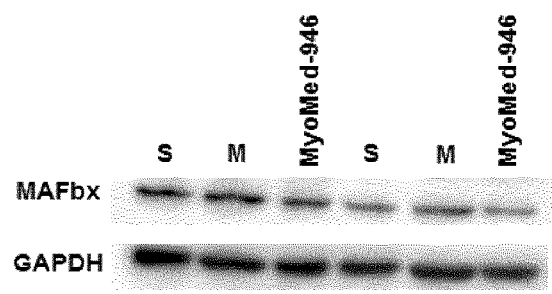
Figure 38:
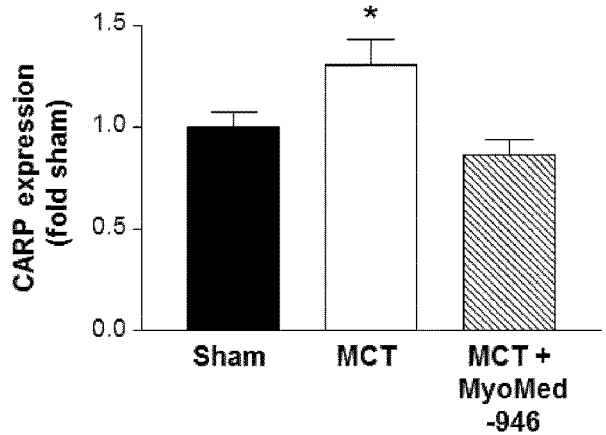
Figure 38:
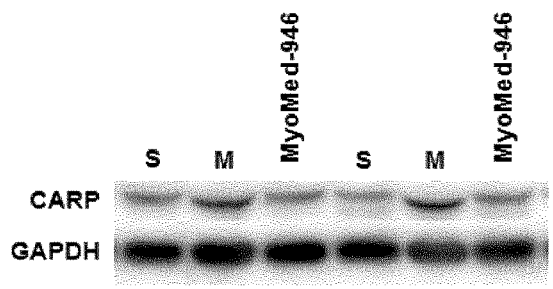

FIG. 36 to 38: Protein expression levels and representative western blots for MuRF1 (FIG. 36), MAFBx (FIG. 37), and CARP (FIG. 38) for sham, MCT, and MCT+MyoMed-946 mice. The MCT treatment leads to an increase in MuRF1 and CARP expression, but this is attenuated in mice fed the MyoMed-946 compound. No changes are detected in levels of MAFBx. *P<0.05 vs. sham and MCT+MyoMed-946.

Figure 39:
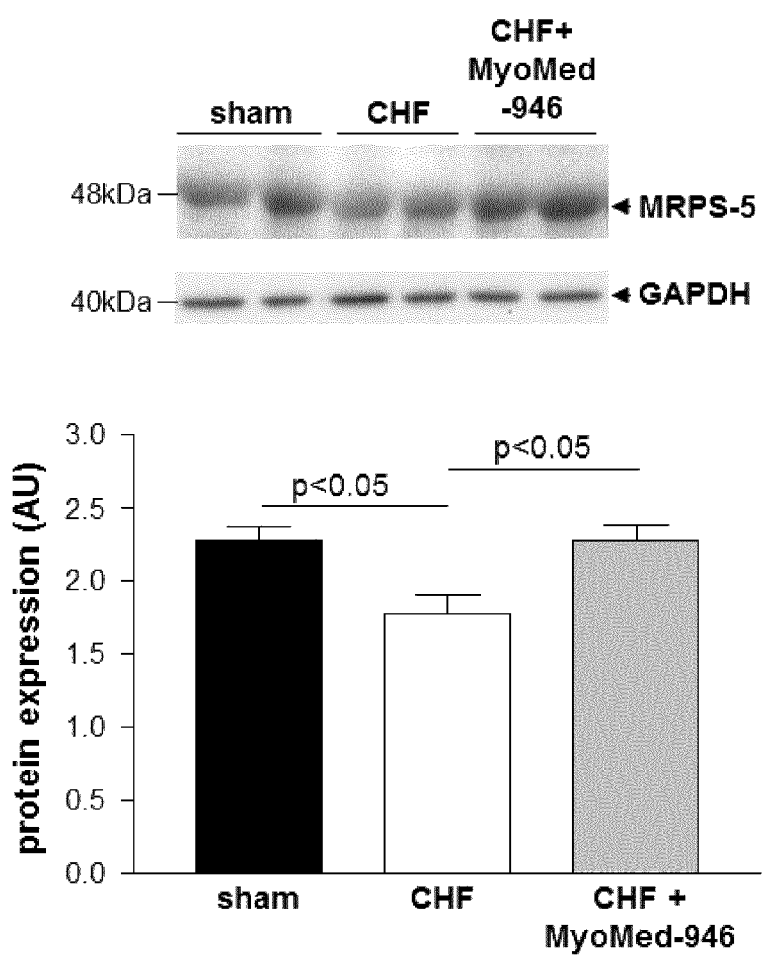

FIG. 39: Protein expression level and representative western blot for MRPS-5 in the diaphragm tissue of sham, CHF, and CHF+MyoMed-946 mice. Data are presented as mean±standard error of the mean.

Figure 40:
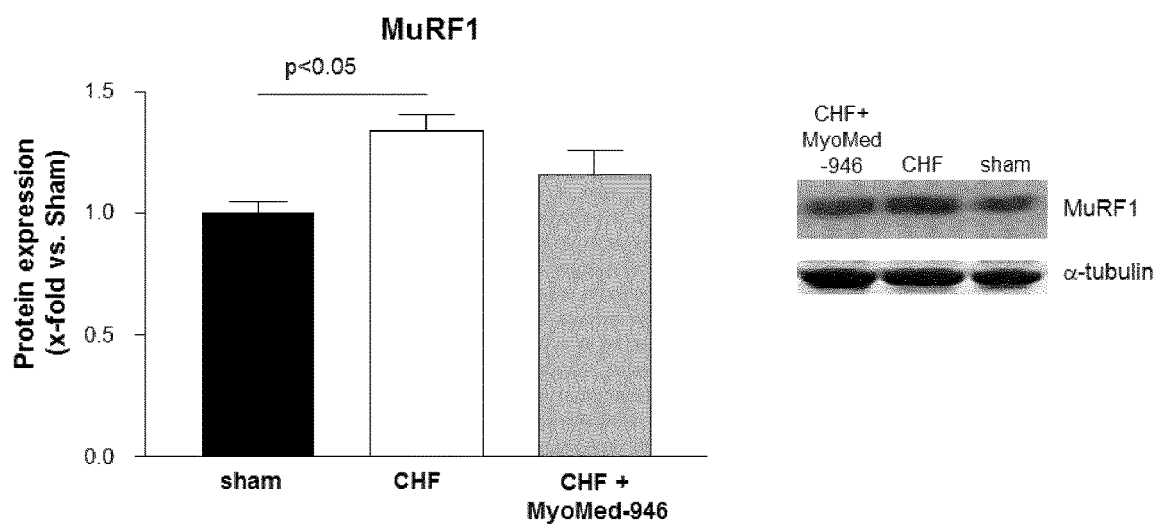
Figure 41:
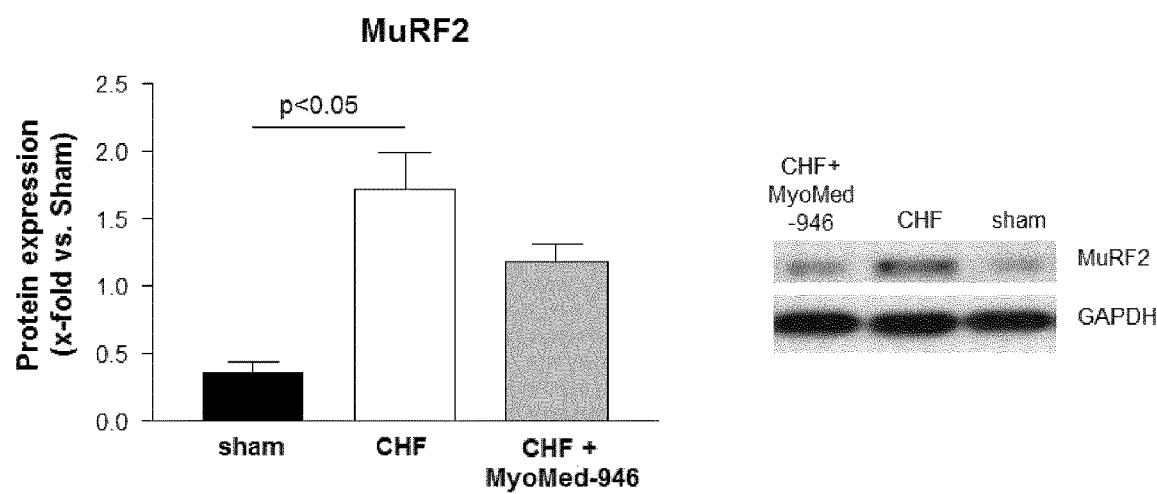
Figure 42:
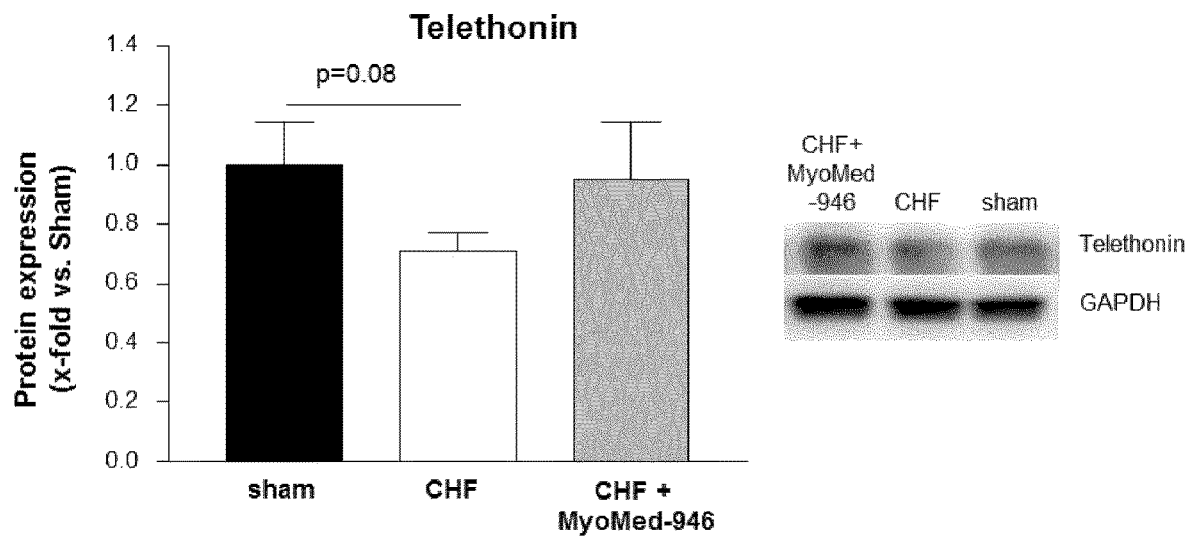

FIGS. 40 to 42: Protein expression levels and representative western blots for MuRF1 (FIG. 40), MuRF2 (FIG. 41), and Telethonin (FIG. 42) in the diaphragm tissue of sham, CHF, and CHF+MyoMed-946 mice. CHF leads to an increase in MuRF1 and MuRF2 expression and to a decrease in telethonin expression, but these effects are attenuated in mice fed with the MyoMed-946 compound. Data are presented as mean standard error of the mean.

FIGS. 43 to 46: Protein expression levels of MuRF1 determined via western blot (WB) analysis (FIG. 43), Nox 2 (FIG. 44) and LC3 I/II (FIG. 46) as well as the level of the reactive oxygen species marker nitrotyrosine (FIG. 45) in muscle tissue of B16F10 cell inoculated mice fed with regular show (tumor) or fed with the compounds MyoMed-946 (tumor+MyoMed-946) or MyoMed-205 (tumor+MyoMed-205). Tumor growth leads to a significant increase of the protein expression level of MuRF1 and Nox 2 as well as of the nitrotyrosine level and to a significant decrease in the expression levels of LC3 I/II in the tumor group compared to mice of the control group (sham). These changes are attenuated in mice fed with the compounds MyoMed-946 (tumor+MyoMed-946) or MyoMed-205 (tumor+MyoMed-205). Data are presented as mean±standard error of the mean.

Figure 47:
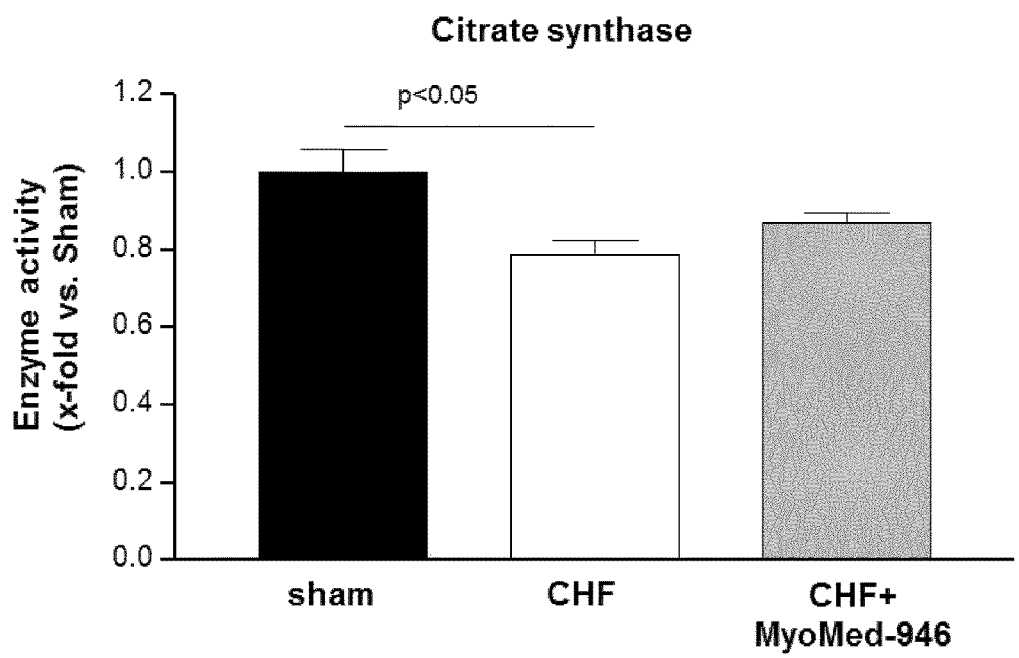
Figure 48:
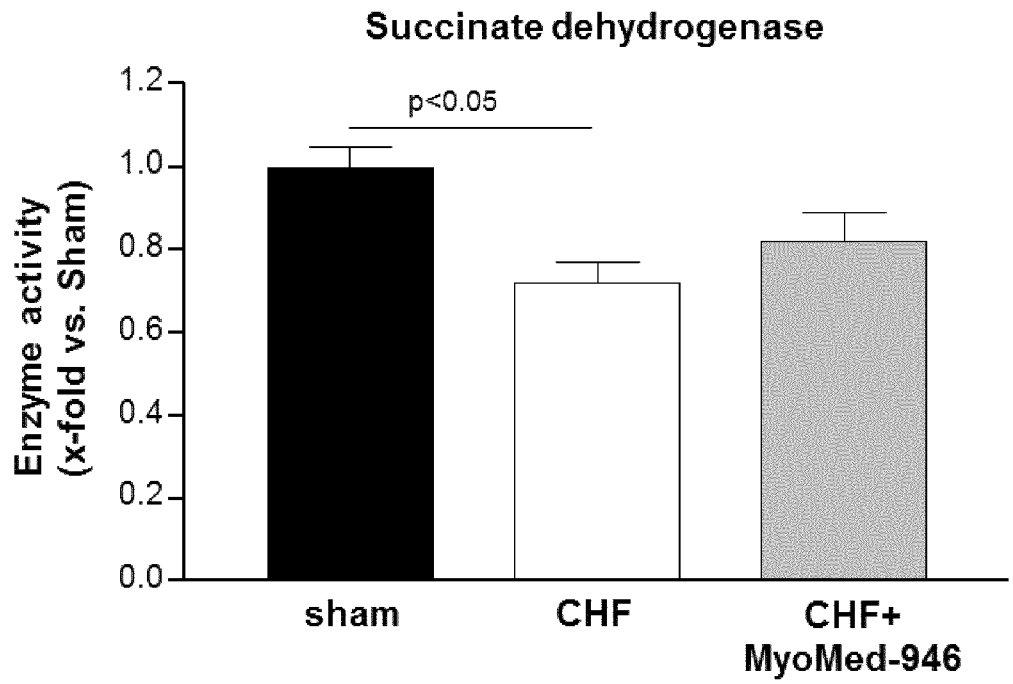
Figure 49:
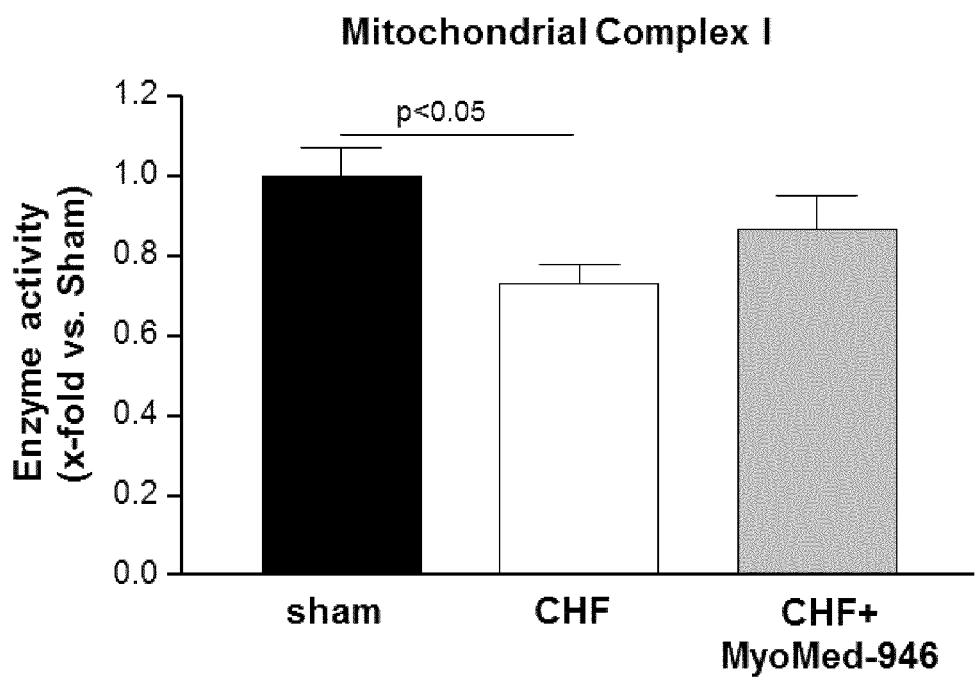

FIGS. 47 to 49: Enzyme activities of citrate synthase (FIG. 47), succinate dehydrogenase (FIG. 48) and mitochondrial complex I (FIG. 49) in diaphragm tissue samples from sham, chronic heart failure (CHF), and CHF+MyoMed-946 mice. The data reveal a significant down-regulation of citrate synthase, succinate dehydrogenase and mitochondrial complex I activity in CHF when compared with sham, but this is attenuated in mice fed with the compound MyoMed-946. Data are presented as mean standard error of the mean.

Figure 50:
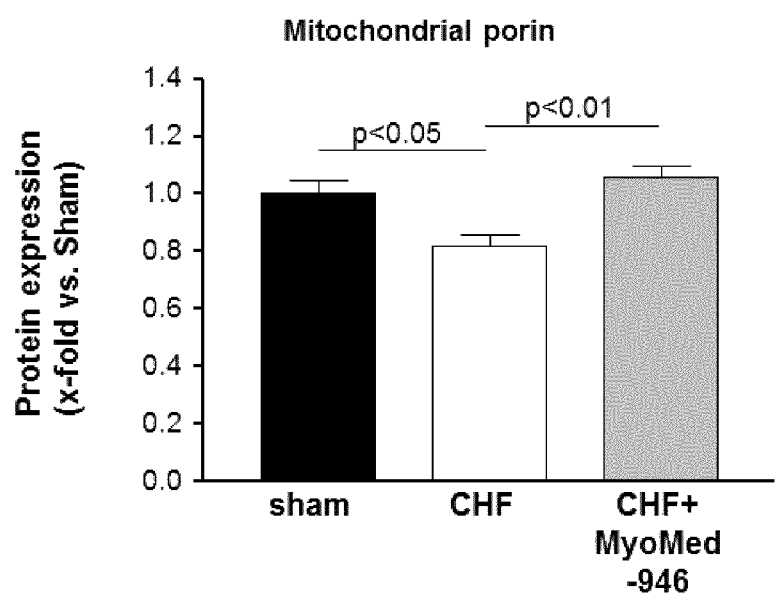
Figure 51:
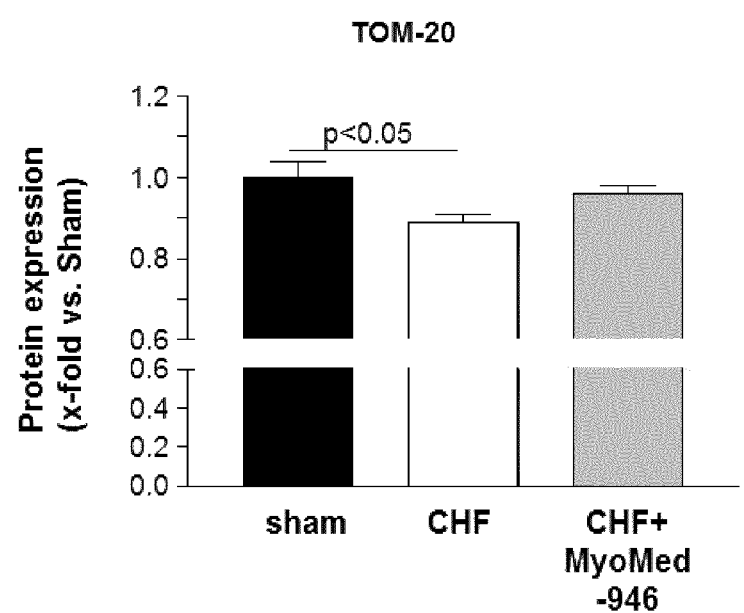

FIGS. 50 and 51: Protein expression levels of mitochondrial porin of the outer mitochondrial membrane (FIG. 50) and TOM-20 (FIG. 51) in diaphragm tissue samples from sham, chronic heart failure (CHF), and CHF+MyoMed-946 mice. The data reveal a significant down-regulation of porin and TOM-20 expression in CHF when compared with sham, but this is attenuated in mice fed the compound MyoMed-946. Data are presented as mean±standard error of the mean.

Figure 52:
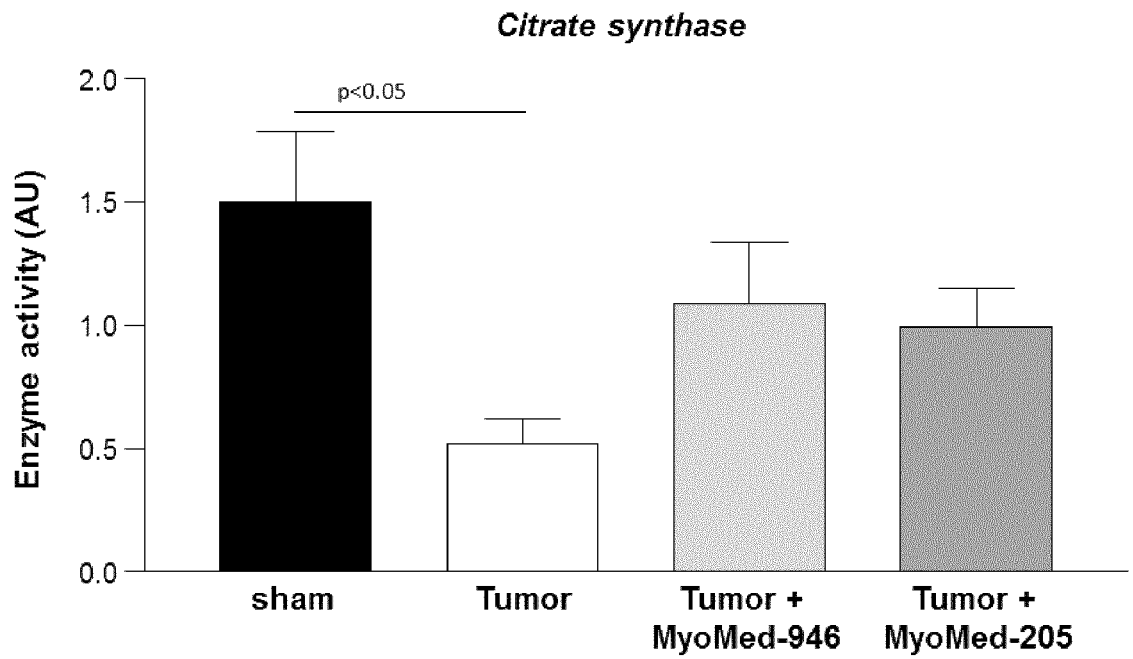
Figure 53:
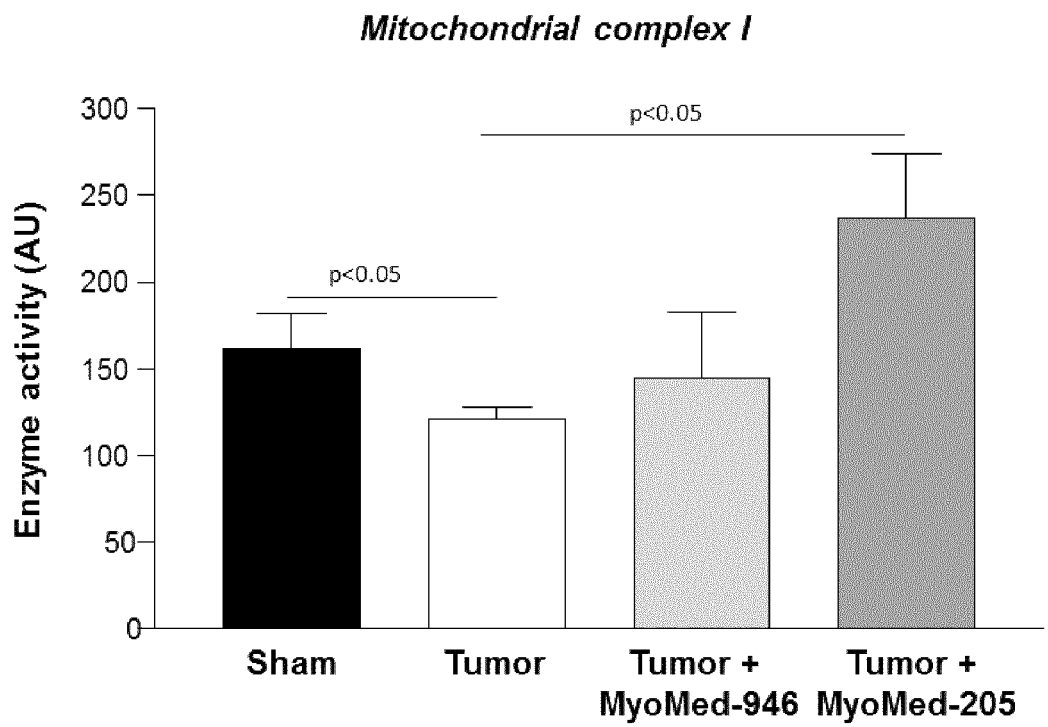

FIGS. 52 and 53: Enzyme activities of citrate synthase (FIG. 52) and mitochondrial complex I (FIG. 53) in muscle tissue samples from sham, B16F10 cell inoculated mice fed with regular show (tumor) and B16F10 cell inoculated mice fed with the compounds MyoMed-946 (tumor+MyoMed-946) or MyoMed-205 (tumor+MyoMed-205). The data reveal a significant down-regulation of citrate synthase and mitochondrial complex I activity in the tumor group when compared with sham, but this is attenuated in mice fed with the compounds MyoMed-946 or MyoMed-205. Data are presented as mean standard error of the mean.

Figure 54:
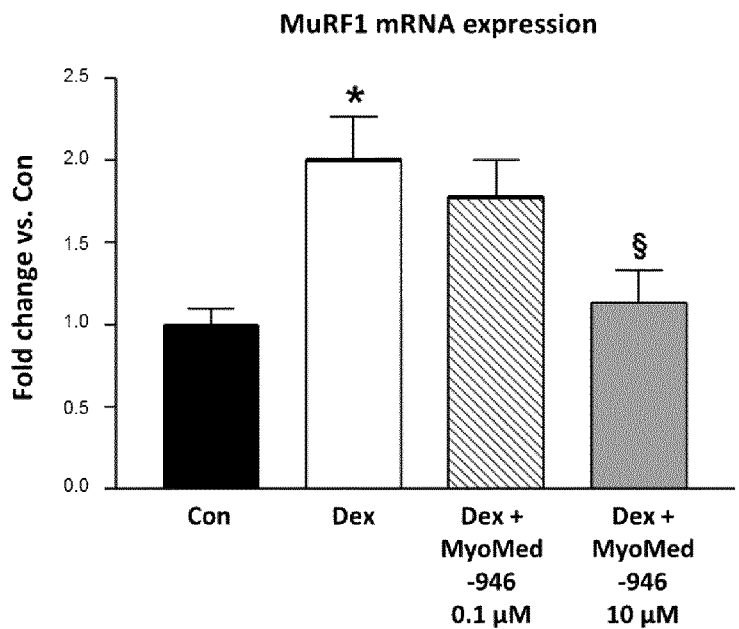

FIG. 54: Expression of MuRF1 at the mRNA level in myotubes, following 24 h incubation with dexamethasone (DEX; 10 μmol/L). Displayed is the fold change of untreated cells (DEX), and cells which have been pre-treated for 2 h with the MyoMed-946 compound at 0.1 μmol/L and 10 μmol/L. The pre-treated cells show reduced MuRF1 mRNA levels. *P<0.05 vs. CON. § P<0.05 vs. DEX.

Figure 55:
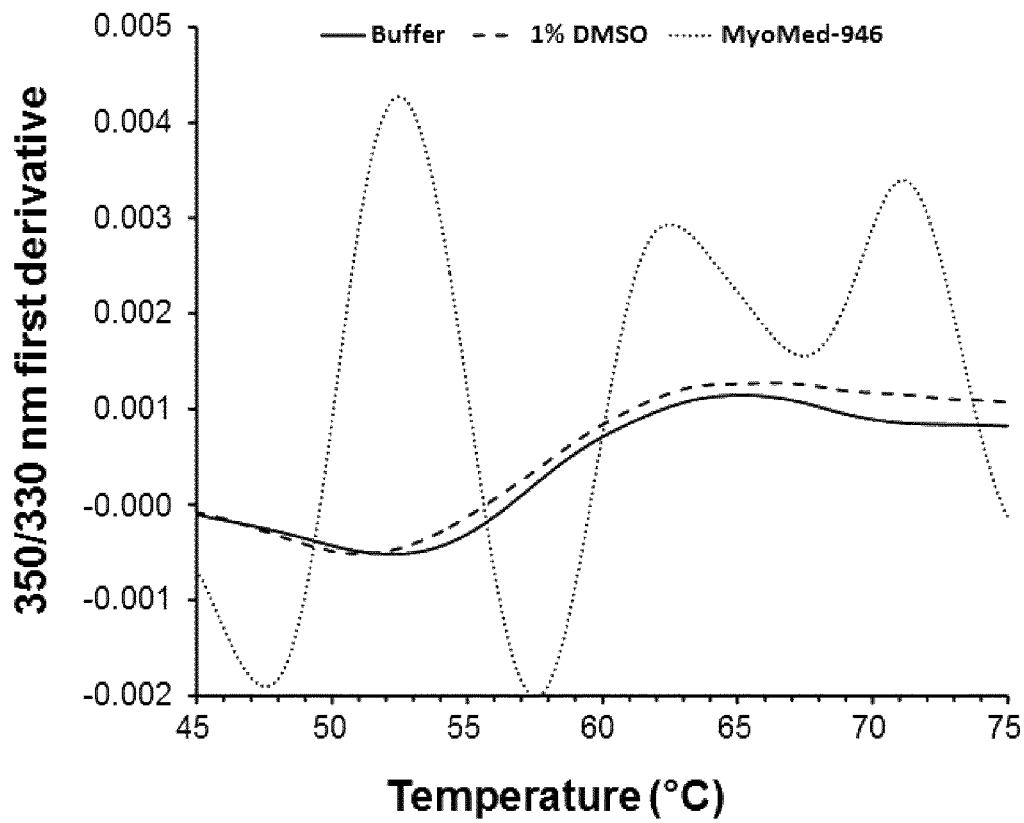

FIG. 55: Differential scanning fluorimetry (DSF) melting curves, plotted as the ratio of the fluorescence signal at 350 nm to the fluorescence signal at 330 nm against a thermal gradient, for MuRF1 central fragment in PBS-buffer (solid line), MuRF1 central fragment in PBS-buffer plus 1% DMSO (dashed line) and for MuRF1 central fragment in PBS-buffer plus 1% of a 10 mM stock of compound MyoMed-946 in DMSO (final concentration of MyoMed-946: 100 μM) (dotted line).

Figure 56:
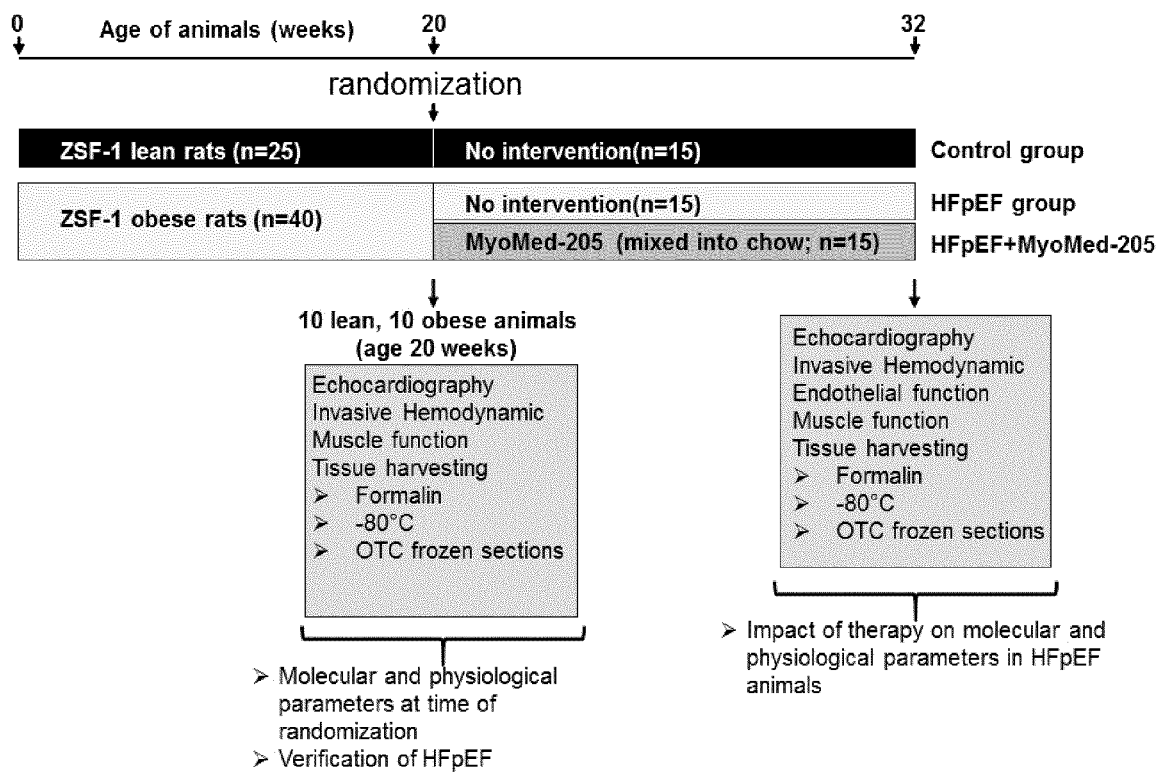

FIG. 56: Schematic drawing of the study design for a HFpEF rat model experiment.

Figure 57:
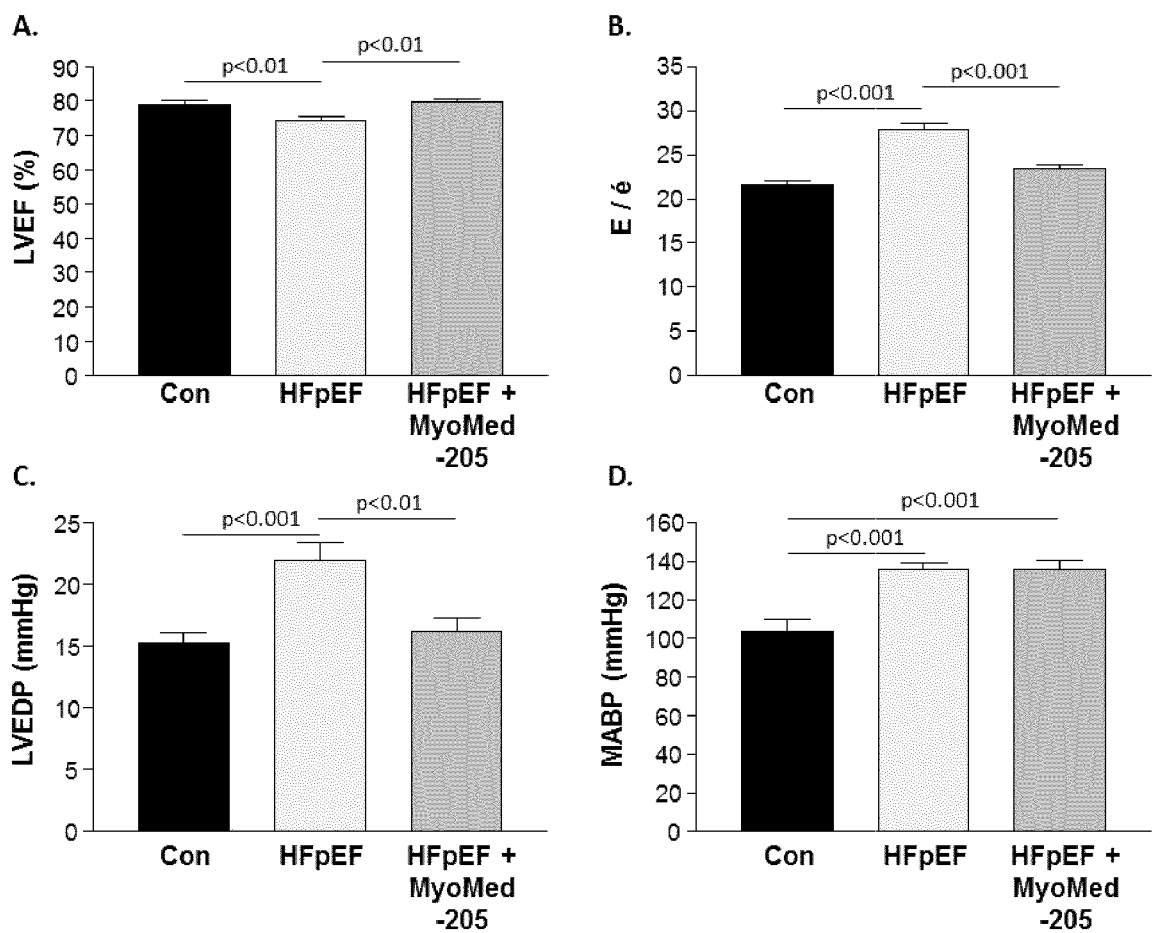

FIG. 57: Results of myocardial function echocardiography and invasive hemodynamic measurements in HFpEF rat model experiment.

Figure 58:
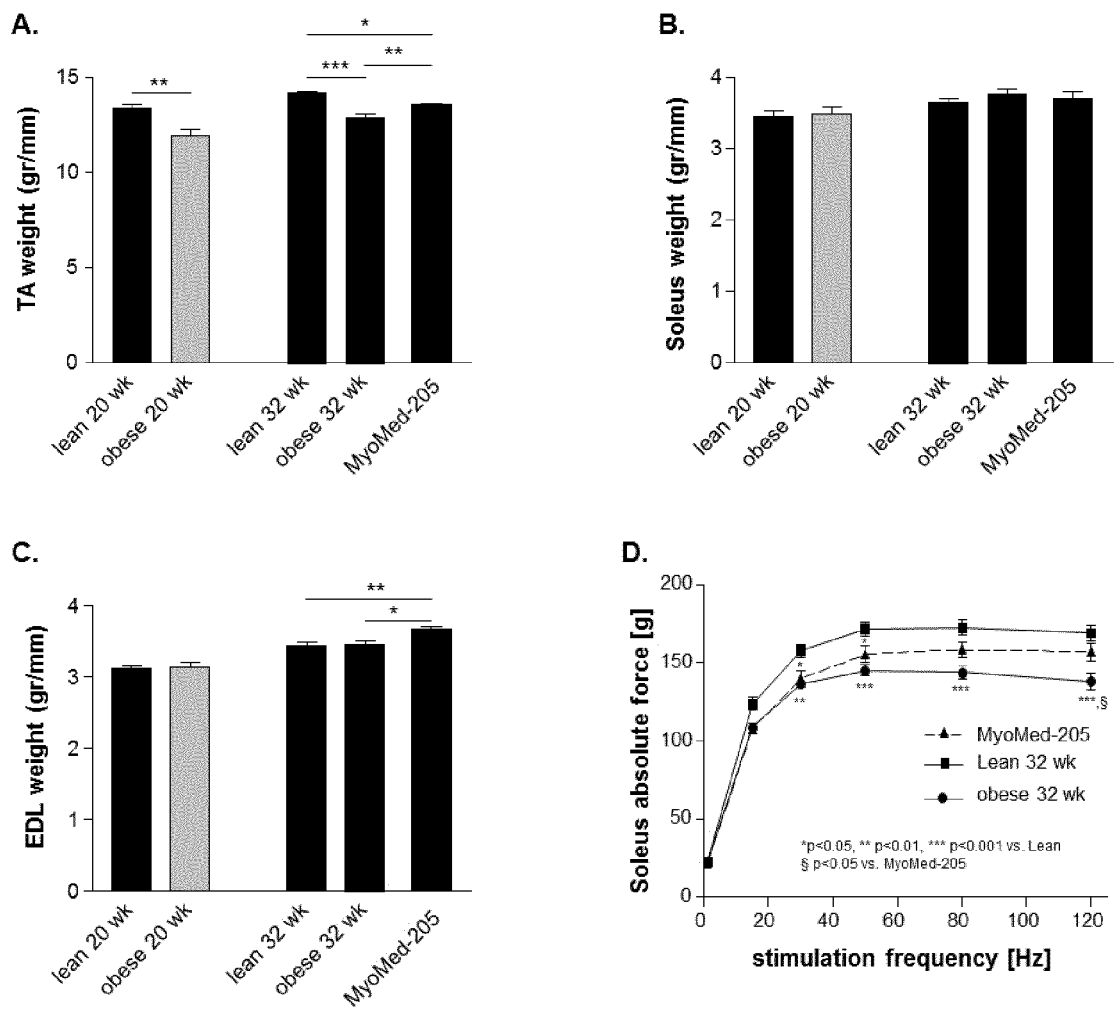

FIG. 58: Results of skeletal muscle mass and function measurements in HFpEF rat model experiment.

Figure 59:
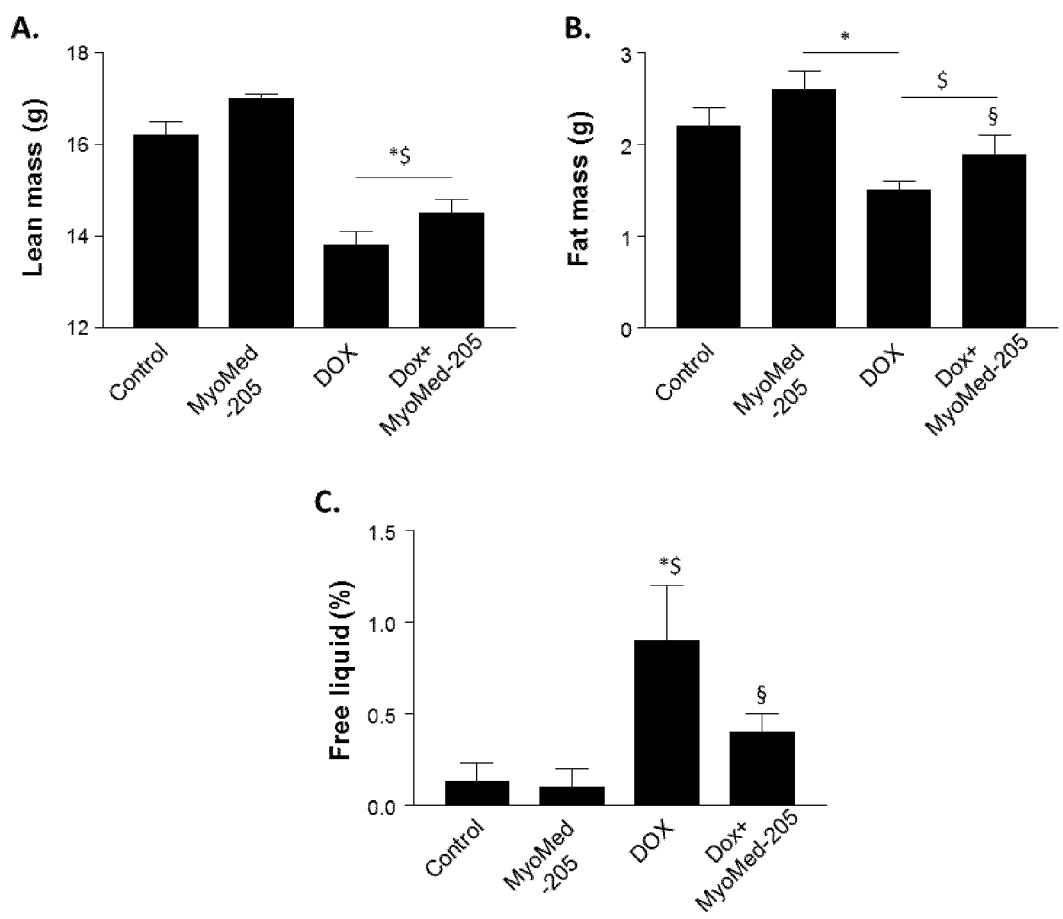

FIG. 59: Cachexia and body stress results in Doxorubicin-induced muscle atrophy and cardiac toxicity mouse model.

Figure 60:
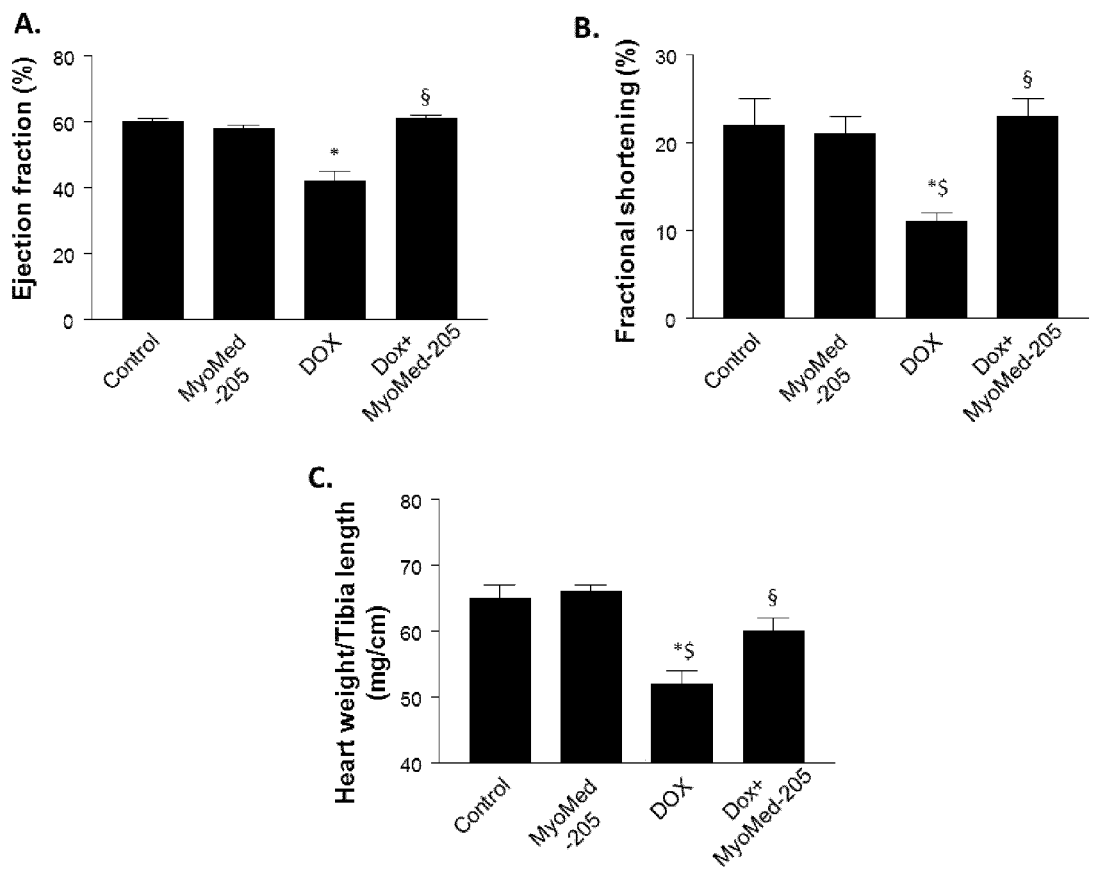

FIG. 60: Echocardiography results in Doxorubicin-induced muscle atrophy and cardiac toxicity mouse model.

Figure 61:
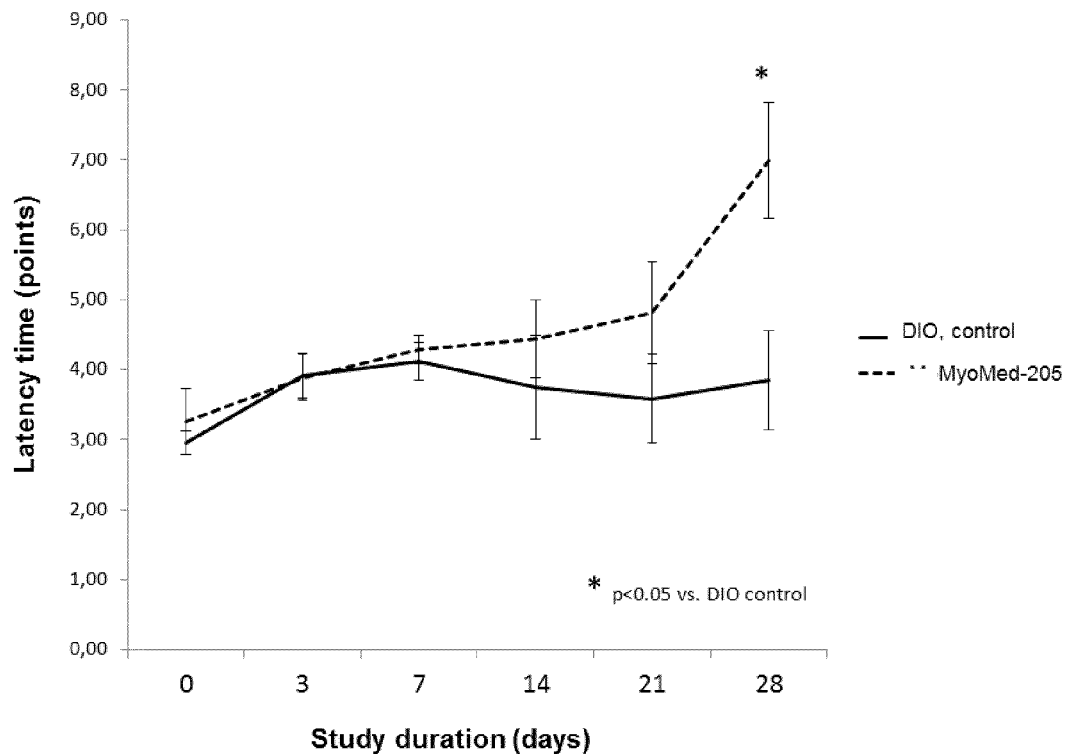

FIG. 61: Wire hang test in obese mice with type 2 diabetes during diet-induced weight loss. Treatment with MyoMed-205 attenuated the loss of muscle function.

Figure 62:
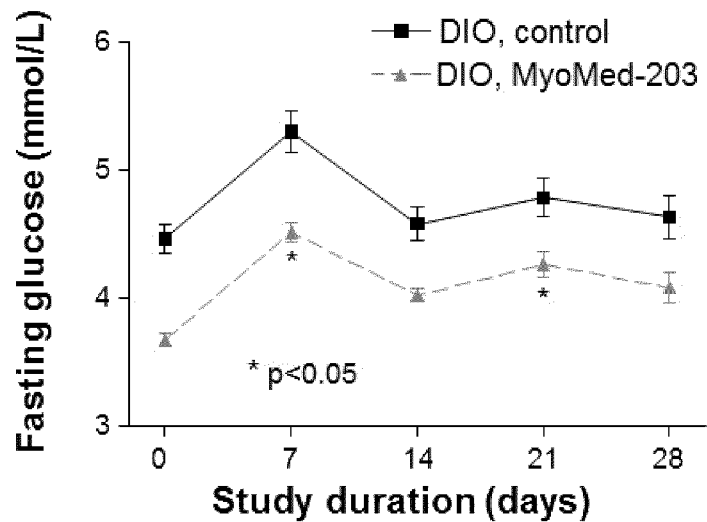

FIG. 62: Blood glucose levels after 6 h fasting in MyoMed-203-treated DIO mice as compared to DIO control mice.

Figure 63:
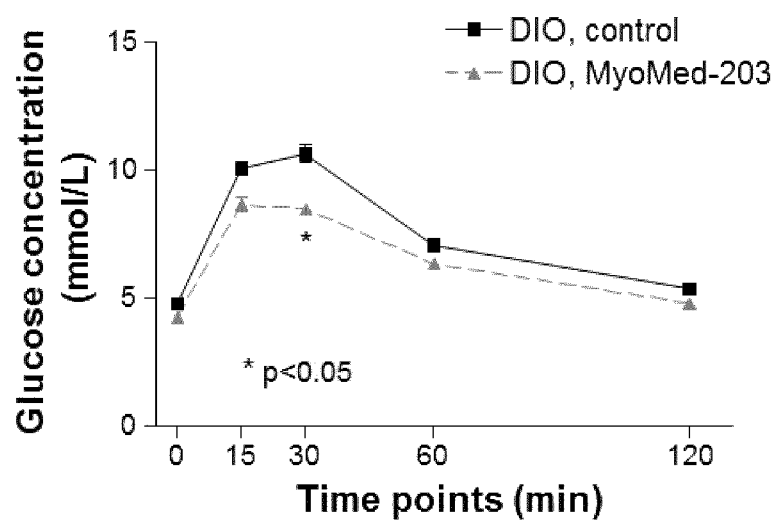
Figure 64:
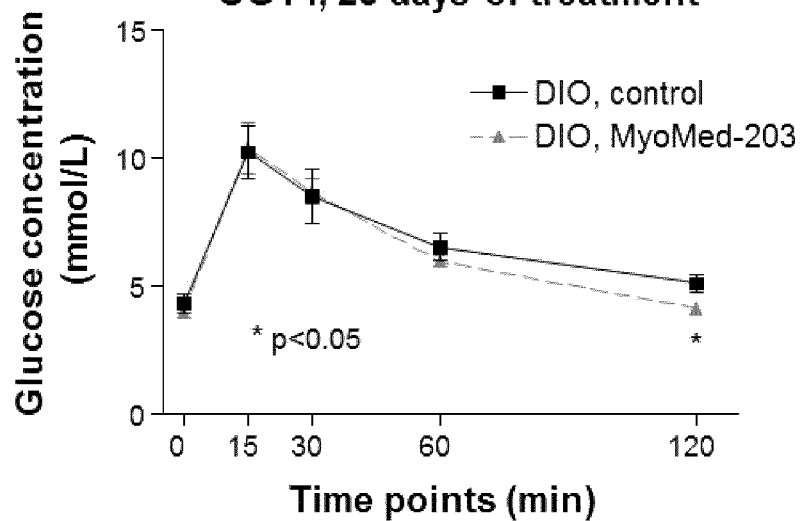

FIGS. 63 and 64: Oral glucose tolerance test results at test days 14 and 28 of MyoMed-203-treated DIO mice as compared to DIO control mice.

Figure 65:
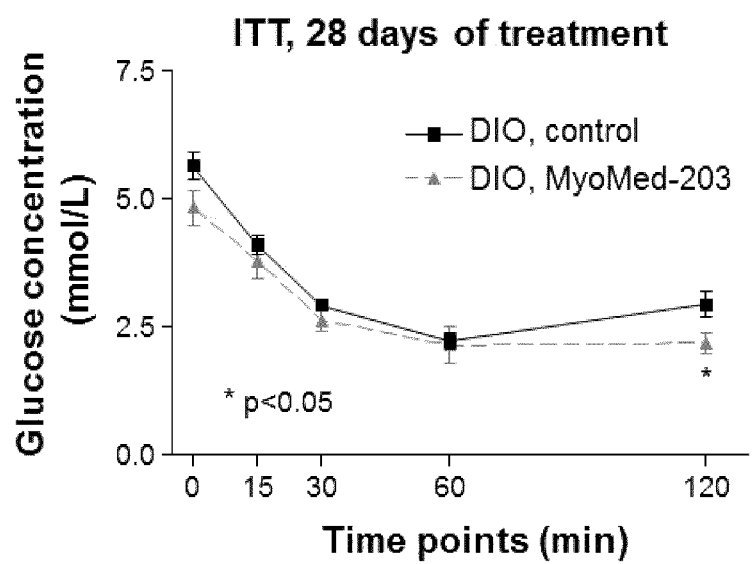

FIG. 65: Insulin tolerance test results of MyoMed-203-treated DIO mice as compared to DIO control mice.

I. SYNTHESIS OF COMPOUNDS I

1. Analytics

The compounds were characterized via $^1$H NMR and eventually $^{13}$C NMR in d6-dimethylsulfoxid (DMSO-d6), if not stated otherwise, on a 400 MHz NMR instrument (Bruker AVANCE III).

The magnetic nuclear resonance spectral properties (NMR) refer to the chemical shifts (δ) expressed in parts per million (ppm). The relative area of the shifts in the 1H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

The compounds were further characterized by HPLC-MS and/or UPLC-MS in a fast gradient on $C_{18}$-material (electrospray-ionisation (ESI) mode). If not stated otherwise, the ESI MS-data are recorded in positive mode. The MS-data refer to the protonated compounds (M+H)$^+$ given as mass over charge-ratio (m/z), where z is 1.

HPLC-MS Specifications:

HPLC-MS Instrument: Agilent 1100 Series LC/MSD system with DAD\ELSD and Agilent LC\MSD VL (G1956A), SL (G1956B) mass-spectrometer or Agilent 1200 Series LC/MSD system with DAD\ELSD and Agilent LC\MSD SL (G6130A), SL (G6140A) mass-spectrometer. All the LC/MS data were obtained using positive/negative mode switching.

Acquisition method: Column: Zorbax SB-C18 1.8 μm 4.6×15 mm Rapid Resolution cartridge (PN 821975-932). Mobile phase: A: acetonitrile plus 0.1% formic acid; B: water with 0.1% formic acid. Flow rate: 3 ml/min; Injection volume: 1 μl.

Solvent Gradient:
100% B from 0 to 0.01 minutes;
100% to 0% B from 0.01 to 1.5 minutes, linear gradient;
0% B from 1.5 to 1.8 minutes;
0% to 100% B from 1.8 to 1.81 minutes.
Ionization mode: atmospheric pressure chemical ionization (APCI);
Scan range: m/z 80-1000.

UPLC-MS Specifications:

UPLC-MS instrument: Agilent Infinity 1290 with a Single Quadrupole, Electrospray Ionisation mass-spectrometer;

Acquisition method: Column: Acquity UPLC BEH C18; 1.7 μm; 2.1×50 mm; T=40° C. Mobile phase: A: Water plus 0.1% trifluoroacetic acid; B: MeCN plus 0.1% trifluoroacetic acid. Flow rate: 1 ml/min; inject volume 3 μl; runtime 3 min.

Solvent Gradients (3 Minute Gradient):
5 to 100% B from 0 to 2.3 minutes, linear gradient;
100% B from 2.3 to 2.5 minutes;
100 to 5% B from 2.5 to 2.6 minutes, linear gradient;
100% B from 2.6 to 3.0 minutes.

If not stated otherwise, the ESI MS-data are recorded in positive mode. The MS-data refer to the protonated compounds (M+H)$^+$ given as mass over charge-ratio (m/z), where z is 1.

2. Synthesis 2.1 Preparative HPLC-Purification

Preparative HPLC-purification was performed using HPLC (H$_2$O-MeOH or H$_2$O—CH$_3$CN; Agilent 1260 Infinity systems equipped with DAD and mass-detectors using a Waters SunFire C18 OBD Prep Column (100 Å, 5 μm, 19 mm×100 mm with SunFire C18 Prep Guard Cartridge, 100 Å, 10 μm, 19 mm×10 mm). The raw compounds were dissolved in 0.7 mL DMSO. Flow: 30 mL/min. Purity of the obtained fractions was checked via analytical LCMS. Spectra were recorded for each fraction as it was obtained straight after chromatography in the solution form. The solvent was evaporated in the flow of N$_2$ at 80° C. The individual fractions were combined on the basis of post-chromatography LCMS analysis. Solid fractions were dissolved in 0.5 mL MeOH/CH$_3$CN and transferred into pre-weighted marked vials. Obtained solutions were again evaporated in the flow of N$_2$ at 80° C. After drying, products were finally characterized by LC-MS and $^1$H-NMR.

2.2 Intermediates 2.2.1 4-[(4-Methyl-2-oxo-chromen-7-yl)oxymethyl]acetic acid

A mixture of 80.6 g (0.458 mol) 7-hydroxy-4-methylcoumarin, 110.1 g of methyl 4-(bromomethyl)benzoate (0.480 mol), and anhydrous K$_2$CO$_3$ 95 g (0.686 mol) in anhydrous acetone (800 mL) was heated to reflux for 3 hrs. The mixture was then cooled, filtered, and the filtrate was concentrated under vacuum. The residue was dissolved in DMSO (450 mL) and aqueous solution of potassium hydroxide (200 mL, 20% KOH) was added. The resulting mixture was stirred at ambient temperature for 72 h. After completion of hydrolysis 1 L of water was added and the solution was acidified with 10% hydrochloric acid to pH=1-2. The formed precipitate was filtered and dried under vacuum to give a pure product. Yield of 4-[(4-methyl-2-oxo-chromen-7-yl)oxymethyl]acetic acid was 75% (106 g).

HPLC-MS (positive mode): m/z 311 (M+H)$^+$; Retention time: 1.11 min.

$^1$H NMR (400 MHz, DMSO-d6, ppm): δ=13.01 (br s, 1H), 8.0-7.97 (m, 2H), 7.71 (d, J=7.0 Hz, 1H), 7.60-7.58 (m, 2H), 7.09-7.05 (m, 2H), 6.23 (s, 1H), 5.34 (s, 2H), 2.40 (s, 3H).

2.2.2 2-Amino-N-(2-furylmethylcarbamoyl)acetamide

A mixture of 1.46 g (6.74 mmol) 2-chloro-N-(2-furylmethyl-carbamoyl)acetamide and sodium azide 90 mg (NaN$_3$, 2 eq.) in 15 mL of ethanol was stirred at 70° C. overnight. After cooling to room temperature the solids were removed and obtained filtrate was concentrated in vacuo (⅓ of volume). The residue was portioned between EtOAc and water. Organic layer was washed with brine, dried over Na$_2$SO$_4$ and evaporated in vacuo. The residue was dissolved in MeOH, and Pd/C was added therein. The mixture was degassed, and was allowed to stir at RT under hydrogen atmosphere overnight. The catalyst was removed, and the filtrate was evaporated and dried in vacuo to afford crude amine, which was used in the next step without further purification. (X═O 0.8 g 60%; X═O 0.7 g 62% (from 2 steps)).

2.2.3 2-Amino-N-(2-thienylmethylcarbamoyl)acetamide

2-Amino-N-(2-thienylmethylcarbamoyl)acetamide was prepared analogous to example 2.2.2, except that 1.26 g (5.41 mmol) 2-chloro-N-(2-thienylmethylcarbamoyl)-acetamide was used as the starting material instead of 2-chloro-N-(2-furylmethyl-carbamoyl)acetamide. The thus obtained crude 2-amino-N-(2-thienylmethyl-carbamoyl)acetamide was used in the next step without further purification. Yield: 0.7 g 62% (from 2 steps).

2.3 Compounds I

Example 1

Synthesis of [2-(2-furylmethylcarbamoylamino)-2-oxo-ethyl] 4-[(4-methyl-2-oxo-chromen-7-yl)oxymethyl]benzoate (MyoMed-946)

A mixture of 310 mg (1.0 mmol) 4-[(4-methyl-2-oxo-chromen-7-yl)oxymethyl]-acetic acid, 228 mg (1.05 mmol) of 2-chloro-N-(2-furylmethylcarbamoyl)acetamide, 75 mg (0.5 mmol) of NaI, and DIPEA 155 mg (1.2 mmol) was dissolved in 6 mL of DMSO. The resulting slurry was stirred for 72 h at room temperature to completion of reaction; conversion was controlled by LC-MS. Then the reaction mixture was poured into 50 mL of water, the resulting precipitate was filtered and washed with additional portion of water, isopropyl alcohol, and hexane subsequently. The solid product was dried under vacuum. Yield of [2-(2-furylmethylcarbamoylamino)-2-oxo-ethyl] 4-[(4-methyl-2-oxo-chromen-7-yl)oxy-methyl]benzoate (MyoMed-946) was 61% (289 mg).

[2-(2-Furylmethylcarbamoylamino)-2-oxo-ethyl] 4-[(4-methyl-2-oxo-chromen-7-yl)oxymethyl]benzoate (MyoMed-946) showed no trace of decay over several months storage at room temperature (confirmed via NMR and LC-MS).

HPLC-MS (Positive mode): m/z 491/492 (M+H)$^+$; Retention time: 1.436 min.

$^1$H NMR (400 MHz, DMSO-d6, ppm): δ=10.50 (br.s, 1H, NH), 7.85 (br.s, 1H, NH), 7.55 (d, J=8.0 Hz, 2H, CH+CH), 7.22 (d, J=8.4 Hz, 1H, CH), 7.15 (d, J=8.0 Hz, 2H, CH+CH), 7.09 (s, 1H, CH), 6.60 (m, 2H, CH+CH), 5.90 (m, 1H, CH), 5.78 (d, J=1.4 Hz, 1H, CH), 5.74 (s, 1H, CH), 4.87 (s, 2H, OCH$_2$), 4.44 (s, 2H, OCH$_2$), 3.88 (d, J=5.2 Hz, 2H, NCH$_2$), 1.91 (s, 3H, CH$_3$).

Further Analytical Characterization of MyoMed-946

The purity and identity of the compound was further assessed using 1D and 2D NMR and UPLC-MS as follows:

For NMR analysis, 2 mg of MyoMed-946 was dissolved in in 1 ml d$_6$-dimethylsulfoxid with trace amounts of CCl$_4$. $^1$H- and $^{13}$C-spectra were recorded as well as COSY and HSQC 2D-NMR spectra for $^1$H-NMR peak assignment.

$^1$H NMR (500 MHz, DMSO-d6+CCl$_4$): δ=10.68 (s, 1H), 8.34 (s, 1H), 8.05 (d, J=7.37 Hz, 2H), 7.53-7.45 (m, 4H), 7.14-6.91 (m, 2H), 6.40 (s, 1H), 6.30-6.16 (m, 2H), 5.37 (s, 2H), 4.94 (s, 2H), 4.44-4.23 (m, 2H), 2.41 (s, 3H).

$^{13}$C NMR (126 MHz, DMSO-d6+CCl4): δ=169.0, 165.1, 161.0, 160.0, 154.6, 153.3, 152.5, 151.8, 142.3 (2C), 129.6 (2C), 128.5, 127.6 (2C), 126.6, 113.5, 112.6, 111.4, 110.4, 107.0, 101.8, 69.1, 62.7, 36.0, 18.1.

For the UPLC-MS analysis, a small amount of MyoMed-946 was dissolved in acetonitrile (MeCN) and 3 μl of this solution was injected onto a C18 UPLC column (Acquity UPLC BEH C18; 1.7 μm; 2.1×50 mm). The UPLC-MS system and analytical method used was as described above.

UPLC-MS (positive mode): m/z=491.1 (M+H)$^+$; Retention time: 1.7 min.

Example 2

Synthesis of (1-methyl-2-oxo-2-ureido-ethyl) 4-[(4-methyl-2-oxo-chromen-7-yl)oxymethyl]benzoate (MyoMed-946-5)

Synthesis was performed analogous to Example 1 except that N-carbamoyl-2-chloro-propanamide was used instead of 2-chloro-N-(2-furylmethyl-carbamoyl)acetamide.

HPLC-MS (Positive mode): m/z 439 (M+H)$^+$; Retention time 1.388 min.

$^1$H NMR (400 MHz, DMSO-d6, ppm): δ=10.63 (br.s, 1H), 8.05-7.98 (m, 3H), 7.72-7.68 (m, 1H), 7.68-7.59 (m, 2H), 7.05-7.01 (m, 2H), 6.23 (s, 1H), 5.35 (s, 2H), 5.22-5.14 (m, 1H), 2.70 (d, 3H), 2.39 (s, 3H), 1.50 (d, 3H).

Example 3

Synthesis of [1-methyl-2-(methylcarbamoylamino)-2-oxo-ethyl] 4-[(4-methyl-2-oxo-chromen-7-yl) oxymethyl]benzoate (MyoMed-946-8)

Synthesis was performed analogous to Example 1 except that 2-chloro-N-(methylcarbamoyl)propanamide was used instead of 2-chloro-N-(2-furylmethyl-carbamoyl)acetamide.

HPLC-MS (Positive mode): m/z 425 (M+H)$^+$; Retention time 1.327 min.

$^1$H NMR (400 MHz, DMSO-d6, ppm): δ=10.51 (br.s, 1H), 8.06-7.97 (m, 2H), 7.73-7.67 (m, 1H), 7.67-7.59 (m, 2H), 7.54 (br, s, 1H), 7.33 (br, s, 1H), 7.09-7.02 (m, 2H), 6.22 (s, 1H), 5.35 (s, 2H), 5.22-5.14 (m, 1H), 2.39 (s, 3H), 1.51 (d, 3H).

Example 4

Synthesis of N-[2-(2-furylmethylcarbamoylamino)-2-oxo-ethyl]-4-[(4-methyl-2-oxo-chromen-7-yl) oxymethyl]benzamide To a cooled solution of 2-amino-N-(2-furylmethylcarbamoyl)acetamide obtained in example 2.2.2 (0.6 mmol), 558 mg (1.8 mmol) 4-[(4-methyl-2-oxo-chromen-7-yl) oxymethyl]-acetic acid, 1-hydroxy-7-azabenzotriazole 109 mg (HOAt, 0.8 mmol) in 2 mL of DMF, EDC 124 mg (0.8 mmol) was added dropwise, and the mixture was allowed to stir at room temperature for overnight. The formed precipitate was collected, washed with methanol, then water, again with methanol and dried to afford 110 mg of the title compound in. Yield: 37%.

$^1$H NMR (400 MHz, DMSO-D$_6$, ppm): δ=10.53 (s, 1H), 8.82 (t, J=5.7 Hz, 1H), 8.51 (br.s, 1H), 7.89 (d, J=8.0 Hz, 2H), 7.70 (d, J=8.6 Hz, 2H), 7.56 (m, 3H), 7.06 (m, 2H), 6.37 (s, 1H), 6.24 (d, J=2.5 Hz, 1H), 6.21 (s, 1H), 3.50 (s, 2H), 4.35 (d, J=5.7 Hz, 2H), 3.99 (d, J=5.0 Hz, 2H), 2.38 (s, 3H).

Example 5

Synthesis of [2-oxo-2-(2-thienylmethylcarbamoylamino)ethyl] 4-[(4-methyl-2-oxo-chromen-7-yl) oxymethyl]benzoate A mixture of 310 mg (1.0 mmol) 4-[(4-methyl-2-oxo-chromen-7-yl)oxymethyl]-acetic acid, 250 mg (1.05 mmol) of 2-chloro-N-(2-thienylmethylcarbamoyl)acetamide, 75 mg (0.5 mmol) of NaI and 155 mg (1.2 mmol) DIPEA was dissolved in 6 mL of DMSO. The resulting slurry was stirred for 72 h at room temperature to completion of reaction; conversion was controlled by LC-MS spectra. Then the reaction mixture was poured into 50 mL of water, the formed precipitate was filtered and washed with additional portion of water, isopropyl alcohol and hexane subsequently. The product was dried under vacuum condition. Yield 61% (310 mg) of [2-oxo-2-(2-thienylmethylcarbamoyl-amino)ethyl] 4-[(4-methyl-2-oxo-chromen-7-yl)oxymethyl]benzoate.

HPLC-MS (Positive mode): m/z 507/508 (M+H)$^+$; Retention time 1.399 min.

$^1$H NMR (400 MHz, DMSO-d6, ppm): δ=10.67 (br s, 1H), 8.47 (br s, 1H), 8.03 (d, J=8.0, 2H), 7.71 (d, J=8.0, 1H), 7.64 (d, J=8.0, 2H), 7.39 (d, J=4.0, 1H), 7.08-6.95 (m, 4H), 6.22 (s, 1H), 5.35 (s, 2H), 4.92 (s, 2H), 4.52 (d, J=4.6, 2H), 2.39 (s, 3H).

Example 6

4-[(4-methyl-2-oxo-chromen-7-yl)oxymethyl]-N-[2-oxo-2-(2-thienylmethyl-carbamoylamino)ethyl]benzamide The title compound was prepared analogous to Example 3. 90 mg of the title compound was obtained. Yield: 30%.

¹H NMR (400 MHz, DMSO-D₆, ppm): δ=10.52 (s, 1H), 8.82 (t, J=5.7 Hz, 1H), 8.63 (br.s, 1H), 7.89 (d, J=8.0 Hz, 2H), 7.68 (d, J=8.7 Hz, 1H), 7.55 (d, J=8.0 Hz, 2H), 7.39 (d, J=4.2 Hz, 1H), 7.07 (m, 2H), 6.98 (s, 1H), 6.95 (m, 1H), 6.21 (s, 1H), 5.31 (s, 2H), 4.23 (d, J=5.2 Hz, 2H), 4.00 (d, J=5.7 Hz, 2H), 2.39 (s, 3H).

Example 7

Synthesis of [2-oxo-2-(2-pyridylmethylcarbamoylamino)ethyl] 4-[(4-methyl-2-oxo-chromen-7-yl)oxymethyl]benzoate (MyoMed-203)

Preparation of 2-chloro-N-(2-pyridylmethylcarbamoyl)acetamide

To a stirring solution of 2-pyridylmethanamine (7.84 g, 72.5 mmol) in anhydrous dichloromethane (100 mL) cooled to −10° C., chloroacetyl isocyanate (8.66 g, 72.5 mmol) was added and the reaction mixture was stirred for 2 h at r.t. The precipitated solid was collected by filtration, washed with dichloromethane (2×30 mL), and dried to obtain 12.0 g (52.7 mmol, yield: 73%) of 2-chloro-N-(2-pyridylmethylcarbamoyl)acetamide.

¹H NMR (500 MHz, Chloroform-d): δ=9.45 (s, 1H), 9.05 (s, 1H), 8.59 (s, 1H), 7.67 (t, J=7.1 Hz, 1H), 7.28 (d, J=8.0 Hz, 1H), 7.24-7.18 (m, 1H), 4.65 (d, J=5.2 Hz, 2H), 4.13 (s, 2H).

HPLC-MS (Negative mode) m/z 226 (M−H)⁺; Retention time 0.565 min.

Preparation of 4-[(4-methyl-2-oxo-chromen-7-yl)oxymethyl]benzoic acid

To a solution of 7-hydroxy-4-methyl-chromen-2-one (80.6 g, 458 mmol) in acetone (1000 mL) K₂CO₃ (94.9 g, 687 mmol) and methyl 4-(bromomethyl)benzoate (110 g, 480 mmol) were added and the reaction mixture was refluxed for 3 h. Then, it was cooled to r.t. and filtered. The filtrate was evaporated under reduced pressure and the residue was mixed with water (1000 mL). The insoluble solid was collected by filtration, washed with water, 2-propanol, and hexane, dried, and dissolved in DMSO (500 mL). 20% aqueous KOH (150 mL) was added to the obtained solution of methyl 4-[(4-methyl-2-oxo-chromen-7-yl)oxymethyl]benzoate and the mixture was left to stir overnight at r.t. After the reaction was completed, it was poured into water (3000 mL) and acidified until pH 1-2 with 10% hydrochloric acid. After 30 min of stirring, the precipitated solid was collected by filtration, washed with water, 2-propanol, and hexane, and dried to obtain 106 g (342 mmol, yield: 75%) of 4-[(4-methyl-2-oxo-chromen-7-yl)oxymethyl]benzoic acid.

Methyl 4-[(4-methyl-2-oxo-chromen-7-yl)oxymethyl]benzoate

¹H NMR (500 MHz, DMSO-d₆): δ=7.98 (d, J=8.1 Hz, 2H), 7.68 (d, J=8.5 Hz, 1H), 7.60 (d, J=8.1 Hz, 2H), 7.12-6.96 (m, 2H), 6.20 (s, 1H), 5.32 (s, 2H), 3.85 (s, 3H), 2.38 (s, 3H).

4-[(4-methyl-2-oxo-chromen-7-yl)oxymethyl]benzoic acid

¹H NMR (400 MHz, DMSO-d₆): δ=12.99 (br s, 1H), 7.96 (d, J=7.2 Hz, 2H), 7.67 (d, J=8.4 Hz, 1H), 7.57 (d, J=7.2 Hz, 2H), 7.11-6.99 (m, 2H), 6.20 (s, 1H), 5.31 (s, 2H), 2.37 (s, 3H).

HPLC-MS (Positive mode) m/z 311 (M+H)⁺; Retention time 1.242 min.

Preparation of [2-oxo-2-(2-pyridylmethylcarbamoylamino)ethyl] 4-[(4-methyl-2-oxo-chromen-7-yl)oxymethyl]benzoate A mixture of 4-[(4-methyl-2-oxo-chromen-7-yl)oxymethyl]benzoic acid (9.28 g, 29.9 mmol), 2-chloro-N-(2-pyridylmethylcarbamoyl)acetamide (7.49 g, 32.9 mmol), DIPEA (4.64 g, 35.9 mmol), and NaI (0.900 g, 6.00 mmol) in DMSO (100 mL) was stirred overnight at r.t. and then poured into cold water (500 mL). The precipitated solid was collected by filtration, washed with water, 2-propanol, and hexane, and dried to obtain 13.8 g (27.5 mmol, yield: 92%) of [2-oxo-2-(2-pyridylmethylcarbamoyl-amino)ethyl] 4-[(4-methyl-2-oxo-chromen-7-yl)oxymethyl]benzoate (MyoMed-203).

¹H NMR (400 MHz, DMSO-d₆): δ=10.65 (br s, 1H), 8.69 (br s, 1H), 8.47 (d, J=4.6 Hz, 1H), 8.01 (d, J=8.1 Hz, 2H), 7.73 (t, J=8.4 Hz, 1H), 7.67 (d, J=8.7 Hz, 1H), 7.61 (d, J=8.1 Hz, 2H), 7.28 (d, J=7.7 Hz, 1H), 7.26-7.20 (m, 1H), 7.08-6.97 (m, 2H), 6.19 (s, 1H), 5.33 (s, 2H), 4.91 (s, 2H), 4.46 (d, J=5.3 Hz, 2H), 2.36 (s, 3H).

HPLC-MS (Negative mode) m/z 502 (M−H)⁺; Retention time 1.176 min.

Example 8

Synthesis of 4-[(4-methyl-2-oxo-chromen-7-yl)oxymethyl]-N-[2-(2-thienylmethyl-carbamoylamino)ethyl]benzamide (MyoMed-205)

Preparation of tert-butyl N-[2-(2-thienylmethylcarbamoylamino)ethyl]carbamate

To a suspension of CDI (42.8 g, 264 mmol) in anhydrous acetonitrile (400 mL) 2-thienylmethanamine (14.9 g, 132 mmol) was added and the reaction mixture was maintained in an ultrasonic bath for 1 h at r.t. Then, water (2.5 mL) was added and the mixture was maintained in an ultrasonic bath for further 30 min. After the degassing of the solution, N-boc-ethylenediamine (21.1 g, 132 mmol) was added and the reaction was stirred for 2 h at 50° C. Then, the mixture was cooled to r.t. and evaporated under reduced pressure. The residue was triturated with water (100 mL), filtered, and dried to obtain 35.2 g (118 mmol, 89%) of tert-butyl N-[2-(2-thienylmethylcarbamoylamino)-ethyl]carbamate.

¹H NMR (400 MHz, DMSO-d₆): δ=7.35 (d, J=5.8 Hz, 1H), 6.97-6.88 (m, 2H), 6.83-6.72 (m, 1H), 6.55-6.38 (m, 1H), 6.07-5.93 (m, 1H), 4.34 (d, J=5.9 Hz, 2H), 3.11-3.00 (m, 2H), 2.99-2.88 (m, 2H), 1.37 (s, 9H).

HPLC-MS (Positive mode) m/z 300 (M+H)⁺; Retention time 1.156 min.

Preparation of 2-(2-thienylmethylcarbamoylamino)ethylammonium chloride

To a solution of tert-butyl N-[2-(2-thienylmethylcarbamoylamino)-ethyl]carbamate (19.5 g, 65.1 mmol) in anhydrous dichloromethane (200 mL) 10% dioxane/HCl (50 mL) was added and the reaction mass was stirred for 2 h at r.t. The precipitated solid was collected by filtration and dried under vacuum to obtain 14.3 g (60.6 mmol, 95%) of 2-(2-thienylmethylcarbamoylamino)ethylammonium chloride.

¹H NMR (500 MHz, DMSO-d₆): δ=8.08 (br s, 3H), 7.35 (s, 1H), 6.93 (s, 2H), 6.78 (br s, 1H), 6.51 (br s, 1H), 4.38-4.29 (m, 2H), 3.31-3.19 (m, 2H), 2.88-2.74 (m, 2H).

HPLC-MS (Positive mode) m/z 200 (M+H)⁺; Retention time 0.428 min.

Preparation of 4-[(4-methyl-2-oxo-chromen-7-yl) oxymethyl]benzoic acid

To a solution of 7-hydroxy-4-methyl-chromen-2-one (80.6 g, 458 mmol) in acetone (1000 mL) K₂CO₃ (94.9 g, 687 mmol) and methyl 4-(bromomethyl)benzoate (110 g, 480 mmol) were added and the reaction mixture was refluxed for 3 h. Then, it was cooled to r.t. and filtered. The filtrate was evaporated under reduced pressure and the residue was mixed with water (1000 mL). The insoluble solid was collected by filtration, washed with water, 2-propanol, and hexane, dried, and dissolved in DMSO (500 mL). 20% aqueous KOH (150 mL) was added to the obtained solution of methyl 4-[(4-methyl-2-oxo-chromen-7-yl)oxymethyl]benzoate and the mixture was left to stir overnight at r.t. After the reaction was completed, it was poured into water (3000 mL) and acidified until pH 1-2 with 10% hydrochloric acid. After 30 min of stirring, the precipitated solid was collected by filtration, washed with water, 2-propanol, and hexane, and dried to obtain 106 g (342 mmol, yield: 75%) of 4-[(4-methyl-2-oxo-chromen-7-yl)oxymethyl]benzoic acid.

Methyl 4-[(4-methyl-2-oxo-chromen-7-yl)oxymethyl]benzoate

¹H NMR (500 MHz, DMSO-d₆): δ=7.98 (d, J=8.1 Hz, 2H), 7.68 (d, J=8.5 Hz, 1H), 7.60 (d, J=8.1 Hz, 2H), 7.12-6.96 (m, 2H), 6.20 (s, 1H), 5.32 (s, 2H), 3.85 (s, 3H), 2.38 (s, 3H).

4-[(4-Methyl-2-oxo-chromen-7-yl)oxymethyl]benzoic acid

¹H NMR (400 MHz, DMSO-d₆): δ=12.99 (br s, 1H), 7.96 (d, J=7.2 Hz, 2H), 7.67 (d, J=8.4 Hz, 1H), 7.57 (d, J=7.2 Hz, 2H), 7.11-6.99 (m, 2H), 6.20 (s, 1H), 5.31 (s, 2H), 2.37 (s, 3H).

HPLC-MS (Positive mode) m/z 311 (M+H)⁺; Retention time 1.242 min.

Preparation of 4-[(4-methyl-2-oxo-chromen-7-yl) oxymethyl]-N-[2-(2-thienyl-methylcarbamoylamino) ethyl]benzamide To a solution of 4-[(4-methyl-2-oxo-chromen-7-yl)oxymethyl]benzoic acid (12.6 g, 40.6 mmol) in DMA (150 mL) CDI (7.26 g, 44.8 mmol) was added and the mixture was stirred for 30 min at r.t. Then, 2-(2-thienylmethylcarbamoylamino)-ethylammonium chloride (10.1 g, 42.7 mmol) and triethylamine (4.90 g, 48.4 mmol) were added and the reaction mass was stirred at 50° C. for 16 h. After the mixture cooled down to r.t., water (600 mL) was added. The precipitated solid was collected by filtration, washed with water, 2-propanol, and hexane, and dried to obtain 13.3 g (27.1 mmol, 67%) of 4-[(4-methyl-2-oxo-chromen-7-yl) oxymethyl]-N-[2-(2-thienyl-methylcarbamoylamino)ethyl] benzamide (MyoMed-205).

¹H NMR (400 MHz, DMSO-d₆): δ=8.61-8.47 (m, 1H), 7.86 (d, J=7.9 Hz, 2H), 7.70 (d, J=8.7 Hz, 1H), 7.55 (d, J=7.9 Hz, 2H), 7.38-7.27 (m, 1H), 7.12-7.02 (m, 2H), 6.51 (t, J=6.0 Hz, 1H), 6.22 (s, 1H), 6.17-6.06 (m, 1H), 5.30 (s, 2H), 4.36 (d, J=5.9 Hz, 2H), 3.32-3.17 (m, 4H), 2.39 (s, 3H).

HPLC-MS (Positive mode) m/z 492 (M+H)⁺; Retention time 1.249 min.

II. BIOCHEMICAL ASSAY

1. MuRF1—Titin Interaction Assay:

Small molecule screens were performed using an ALPHA screen to identify compounds that inhibit interaction between MuRF1 and titin. This screen is based on MuRF1 and titin interaction studies that identified the MuRF1 B-box-coiled domain to interact with titin A169 (see for example Mrosek et al., *Biochemistry* 2008, 47, 10722-10730). A prototype of this ALPHA screen assay is described in WO 2009/077618.

Procedure:

These interacting fragments were expressed as GST and biotin fusion proteins so that complex formation could be monitored with glutathione acceptor and avidin donor beads, respectively, as described in WO 2009/077618. A survey of 280,000 compounds (in-house library, EMBL chemical core facility) identified a total of 40 molecules with Ki values of 5-25 μmol/L for the MuRF1-titin interaction.

2. Determination of the Inhibition of MuRF1 E3 Ligase Activity:

Compounds were then assessed for effects on MuRF1 E3 ligase activity directed to titin or to MuRF1 itself (self-ubiquitination) by mixing 75 nmol/L UBE1 (Boston Biochem), 1 μmol/L UbcH5c (Boston Biochem), 100 μmol/L Ubiquitin, 4 mmol/L ATP, 100 nmol/L Titin A168-170 with 20-100 μmol/L of respective compounds. Reactions were started by addition of 220 nmol/L MuRF1, followed by 1 h at 37° C., SDS PAGE and Western blot analysis with MuRF1 and titin specific antibodies. All reactions also included 5% DMSO. MyoMed-946, MyoMed-946-5, and MyoMed-946-8 were tested and could be identified to significantly inhibit MuRF1 E3 ligase activity, based on ubiquitination patterns.

3. Differential Scanning Fluorimetry (DSF) of MuRF1 Central Fragment in the Absence and Presence of the Compound MyoMed-946:

The effect of compound MyoMed-946 on MuRF1 protein stability was determined in vitro by differential scanning fluorimetry (DSF).

Method:

"MuRF1 central fragment" was expressed as previously described (Mrosek M et al., FASEB J, 2007, 21, 1383-1392) and used in DSF experiments at 75 μM final concentration. Compound MyoMed-946 was diluted from a 10 mM stock in DMSO to 100 μM in PBS as DSF assay buffer, resulting in a final concentration of 1% DMSO. After 1 hour pre-incubation at room temperature, the aqueous protein solutions were soaked into capillaries and placed into a Prometheus NT.48 nanoDSF device (NanoTemper Technologies, Munich, Germany). Changes in the intrinsic tryptophan or tyrosine fluorescence that occurred after LED laser excitement upon protein unfolding in a thermal gradient was detected at 330 nm and 350 nm, respectively. Changes in the intrinsic protein fluorescence in a thermal gradient were monitored at 350 nm and 330 nm, respectively. The first derivative of the fluorescence wavelength ratio of 350/330 nm upon thermal protein unfolding was used to calculate transition midpoint (Tm) of single and multiple transition states.

Results:

As can be seen from FIG. 55, Tm of MuRF1 central fragment in PBS was 65.2° C. (solid line) and was only negligibly changed to 65.8° C. by the addition of 1% DMSO (dashed line). In contrast, a strong effect on the thermal unfolding of MuRF1 was observed by the addition of compound MyoMed-946 (dotted line). Compound MyoMed-946 destabilized MuRF1 as indicated by the significantly reduced main Tm of 52.5° C.

III. BIOLOGICAL INVESTIGATIONS

1. Cell Culture Experiments

Murine C2C12 myoblasts (CRL-1772, ATCC) were cultured in DMEM (Lonza; Basel, Switzerland) supplemented with 10% fetal calf serum (FCS; Gibco®Invitrogen, Carlsbad, CA). For induction of differentiation into myotubes, subconfluent cultures were switched to DMEM containing 2% horse serum (Sigma-Aldrich; Seelze, Germany). Myotubes were subsequently pre-treated for 2 h with increasing compound concentrations (0.1 to 10 µmol/L, dissolved in DMSO) or with an equal volume of DMSO before treatment for 24 h with 10 µmol/L dexamethasone (DEX; Sigma-Aldrich; Seelze, Germany). Myotube diameter was then evaluated by image analysis software (Analysis 3.0, Olympus Soft Imaging Solutions GmbH, Munster, Germany). To determine cytotoxicity of selected compounds, myoblasts or myotubes were incubated with increasing concentrations for 24 h. Subsequently, the concentration of lactate dehydrogenase (LDH) activity was quantified in the cell culture supernatant as a measure for cell destruction as described in Bellocci et al., *Anal Biochem*, 2008, 374, 48-55. As can be seen from the FIGS. 1 and 2, the compound MyoMed-946 shows low toxicity in both, myoblasts and myotubes (myocytes).

2. Animal Experiments 2.1 Pulmonary Hypertension Mouse Model:

2.1.1 Test Series 1 with MuRF1 Inhibitor MyoMed-946:

The animal experiments were approved by the Regierungspräsidium Karlsruhe (35-9185.81/G-141/13) and the Regierungspräsidium Leipzig (TVV 40/16). Three groups of mice were included in this study, including: 1) saline-treated (sham; n=20); 2) monocrotaline (MCT)-treated fed normal chow (MCT; n=27); and 3) MCT-treated fed MuRF1 inhibitor chow (MCT+compound; n=27). Briefly, C57BL/6 mice (aged 8 weeks) were subcutaneously injected weekly with either MCT (600 mg/kg) or a matched volume of saline for 6 weeks, a time period where MCT is known to induce cardiac cachexia due to pulmonary hypertension and subsequent RV dysfunction rather than anorexia, as described by Ahn et al., *PLoS One*, 2013, 8:e62702. Mice were exposed to identical conditions under a 12:12 h light/dark cycle with food and water provided ad libitum. The MCT+compound group started receiving the inhibitor chow 1 week prior to the MCT injections, whereas the sham and MCT groups were fed an identical chow but without the addition of the selected compound. Body weight was recorded every week for each mouse. Mice were sacrificed following deep anesthetization with i.p. administration of fentanyl (0.05 mg/kg), medetomidine (0.5 mg/kg), midazolam (5 mg/kg) and ketamine (100 mg/kg). At sacrifice, the heart and lungs were dissected, cleaned, blotted dry and weighed, with the heart fixed in 4% PBS-buffered formalin. The left tibialis anterior (TA), soleus, extensor digitorum longus (EDL), and section of costal diaphragm were also dissected, weighed and fixed in 4% PBS buffered formalin, while the remaining muscle portions were immediately frozen in liquid $N_2$ for molecular analysis.

For histological evaluation, paraffin-embedded TA muscle sections (3 µm) were stained with H&E and fiber cross-sectional area (CSA) and then evaluated by imaging software (Analysis 3.0, Olympus Soft Imaging Solutions GmbH, Munster, Germany). In addition, medial cross sections (3 m) of the heart were mounted on glass slides and subsequently stained with H&E to assess RV wall thickness.

Figure 3:
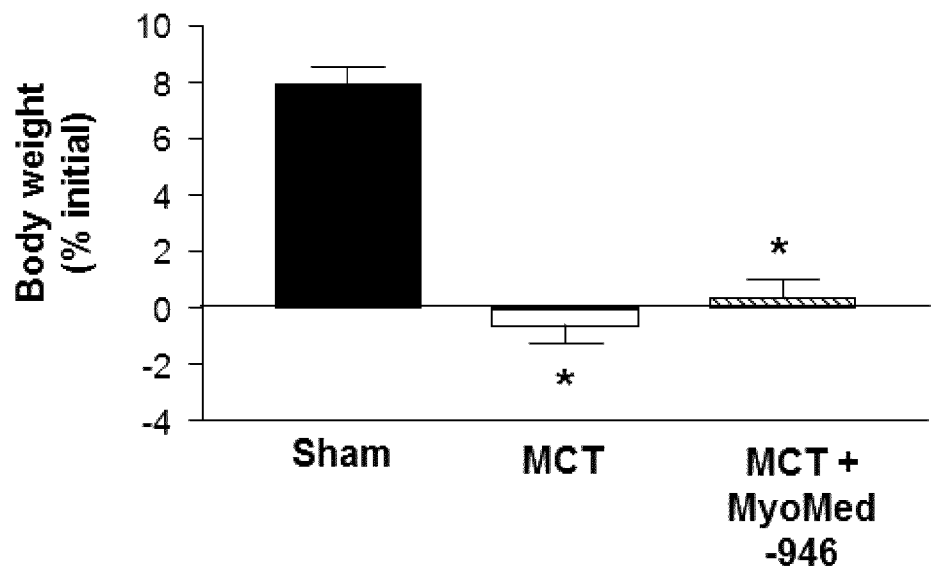
Figure 4:
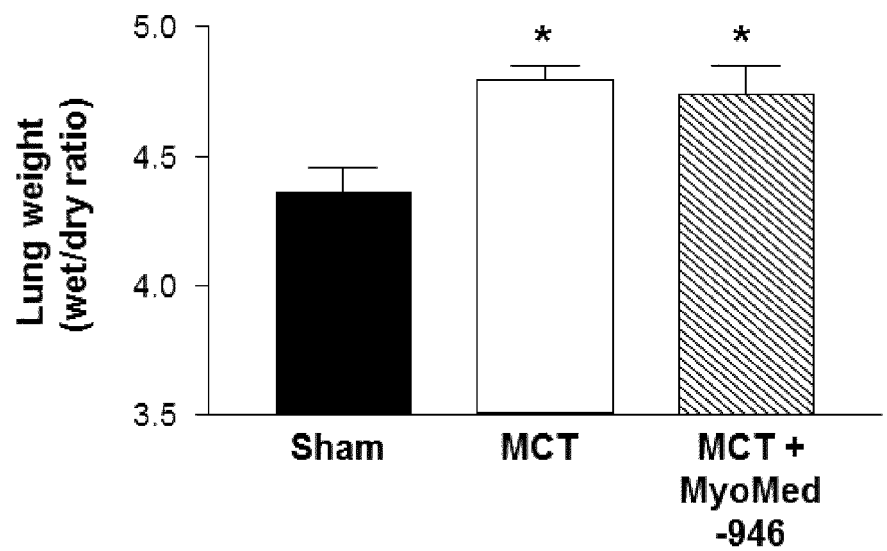
Figure 5:
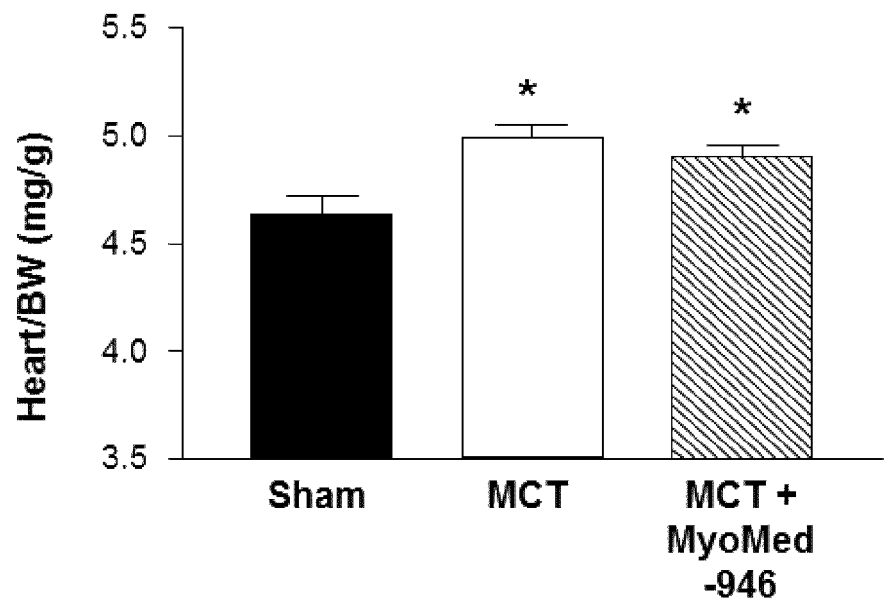
Figure 6:
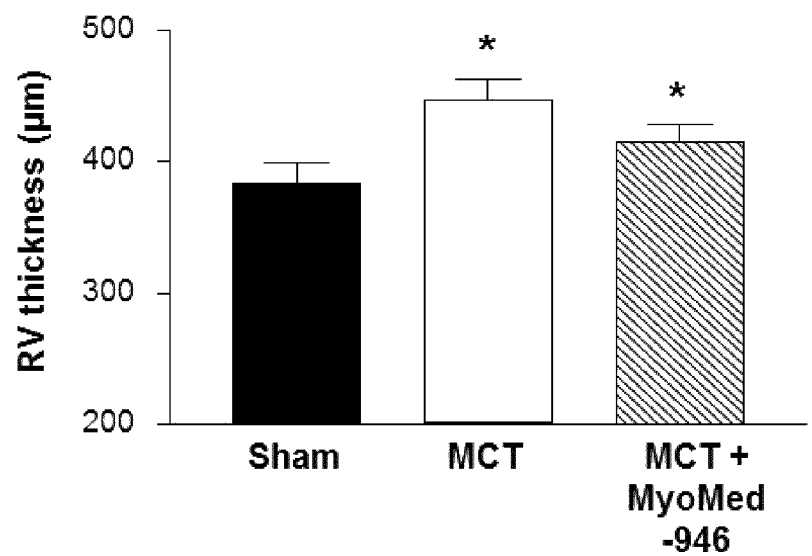
Figure 7:
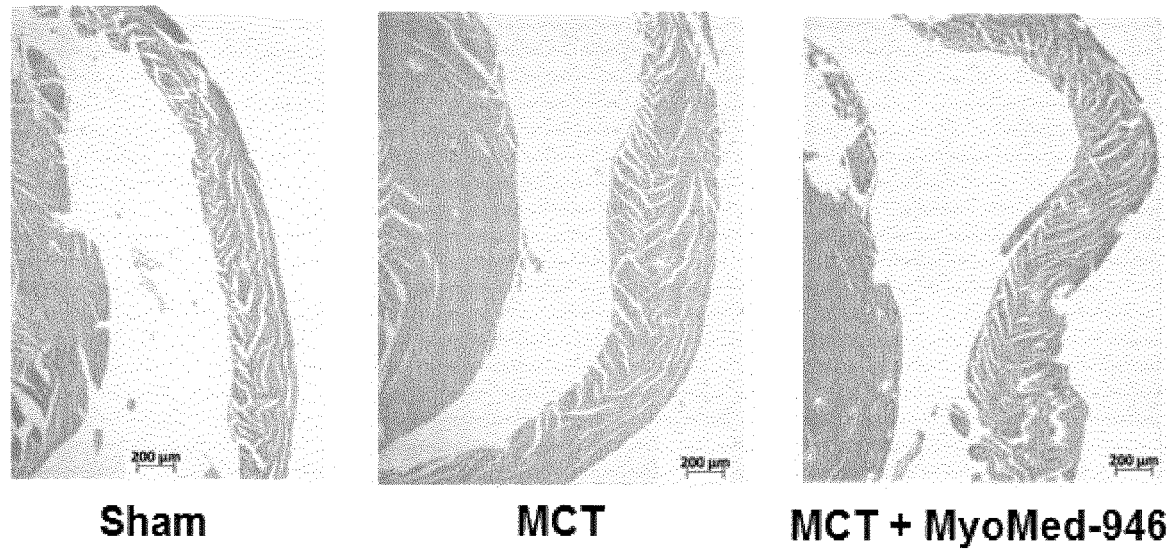
Figure 8:
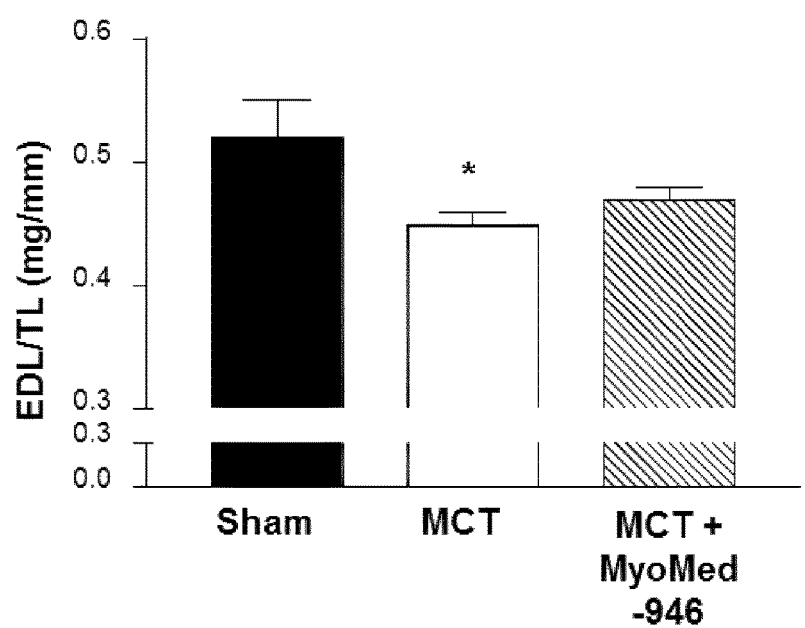
Figure 9:
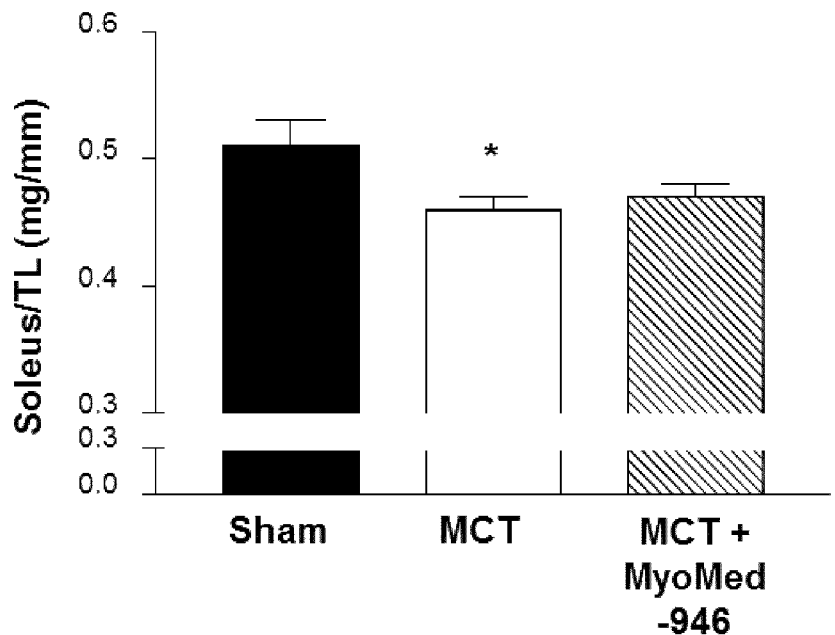
Figure 10:
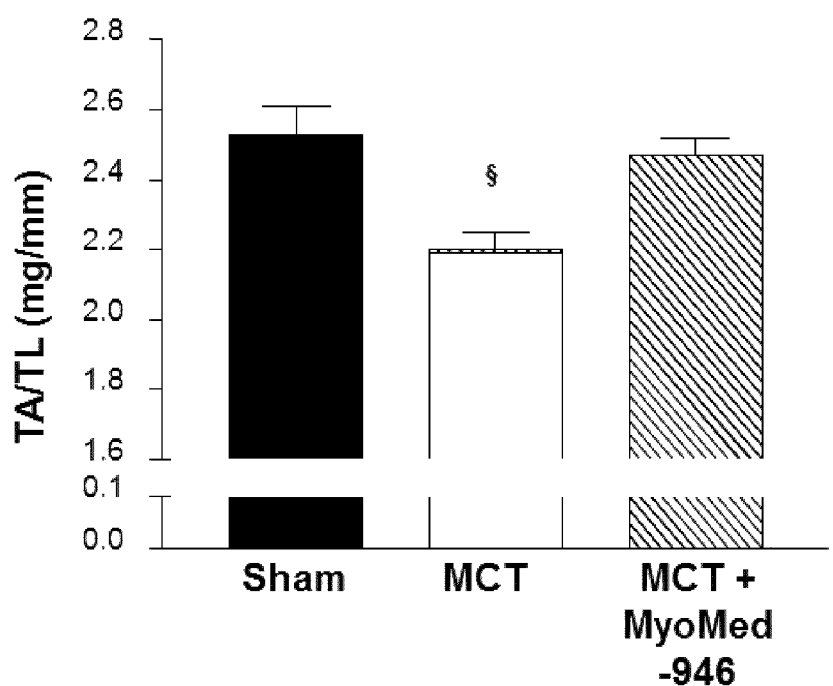
Figure 11:
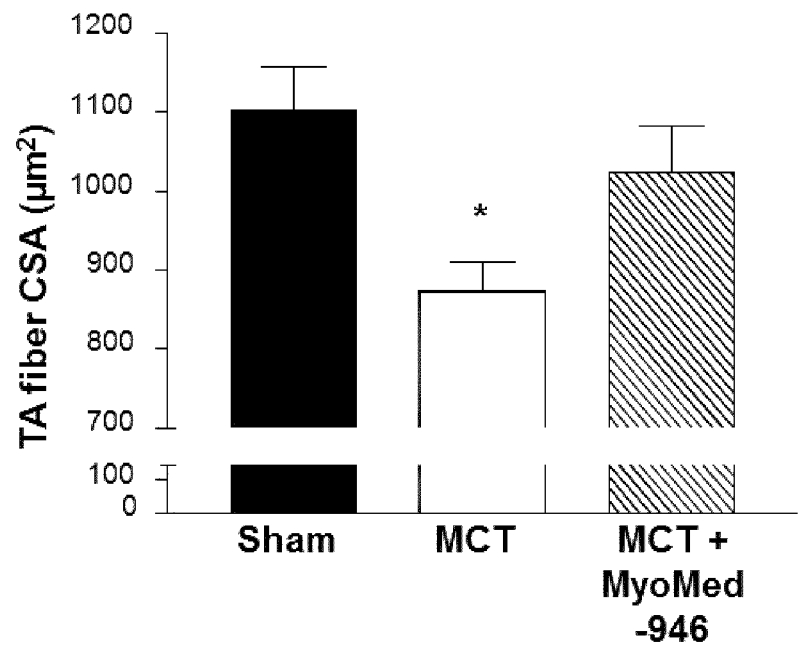
Figure 12:
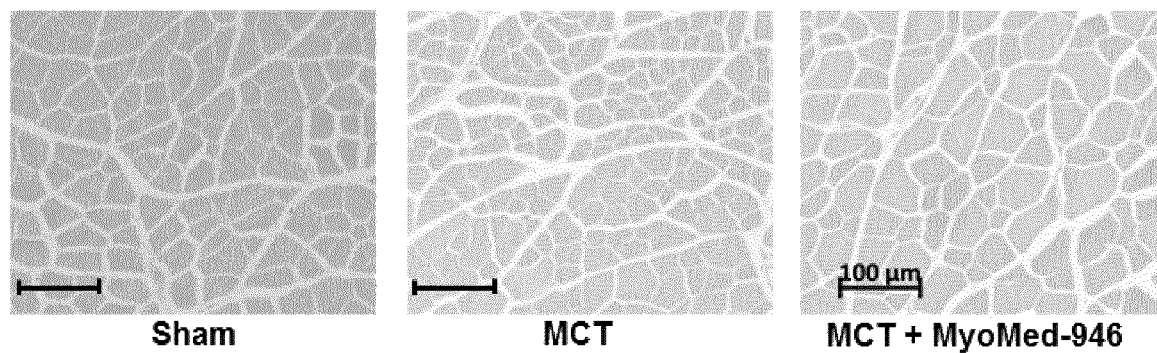

As can be seen from FIGS. 3 to 5, the weight gain, lung weight and heart weight were near identical between the MCT and MCT+MyoMed-946 fed mice, which suggests that the disease progressed in both groups independent of compound feeding. Importantly, as can be seen from FIGS. 6 and 7, the MuRF1 inhibitor MyoMed-946 attenuates the development of right ventricle hypertrophy. Furthermore, as can be seen from FIGS. 8 to 12, while MCT treated mice showed a progressive loss of skeletal muscle mass, the MCT+compound fed mice did not follow this trend and were protected—the most obvious effect seen in the TA muscle.

2.1.2 Test Series 2 with MuRF1 Inhibitors MyoMed-946, MyoMed-203 and MyoMed-205:

The test series 2 were performed analogous to test series 1. Briefly, Three groups of mice were included in this study: 1) saline-treated mice (sham; n=10); 2) monocrotaline (MCT)-treated mice fed with normal chow (MCT; n=10); and 3) MCT-treated mice fed with MuRF1 inhibitor chow (MCT+compound; n=10 for each compound). 8 weeks old C57BL/6 mice were subcutaneously injected weekly with either MCT (600 mg/kg) or a matched volume of saline for 8 weeks. The MCT+compound group started receiving the inhibitor chow 1 week prior to the MCT injections, whereas the sham and MCT groups were fed an identical chow but without the addition of the selected compound. The compound concentration in the chow was 0.1 weight-%, resulting in a daily compound intake per mouse of about 3 mg. Body weight was recorded every week for each mouse. Mice were sacrificed after 8 weeks treatment. At sacrifice, examination and tissue analysis were performed as described in test series 1.

As can be seen from FIGS. 13 to 15, the weight gain, lung weight and heart weight were similar between the MCT and MCT+compound fed mice, which suggest that the disease progressed in both groups independent of compound feeding. Also in this test series, as can be seen from FIGS. 16 to 18, the MuRF1 inhibitors MyoMed-946, MyoMed-203 and MyoMed-205 attenuate the development of right ventricle hypertrophy. Furthermore, as can be seen from FIGS. 19 to 21, while MCT treated mice showed a progressive loss of skeletal muscle mass, the MCT+compound fed mice did not follow this trend and were protected—the most pronounced effect seen for the compound MyoMed-203. Furthermore, the MuRF1-expression level in the TA muscle tissue is clearly reduced in MCT+compound fed mice, where the most pronounced reduction is seen for the compound MyoMed-205, as can be seen from FIG. 22. Also the expression level of telethonin, a MuRF1 target protein, is essentially normalized in the MCT+compound fed mice, as can be seen from FIG. 23.

2.2 Myocardial Infarction LAD Mouse Model:

A myocardial infarction mouse model suffering from a heart failure with reduced ejection fraction (HFrEF) was generated by ligating the left anterior dexterior coronary artery (LAD) as described below to induce an acute myocardial infarction (MI) followed by the development of a chronic (systolic) heart failure (CHF).

LAD Ligation Procedure:

A small animal surgery was carried out on C57/BL6 mice at 12 weeks of age in the Leipzig Heart Center following established and well known procedures in the field (see for example Bowen et al., J Appl Physiol, 2015, 118, 11-19; Mangner et al., J Cachexia Sarcopenia Muscle, 2015, 6, 381-390). Briefly, mice from the LAD group were anesthetized by i.p. injection of MMF; Medetomidin (0.5 mg/kg body weight), Midazolam (5.0 mg/kg body weight), Fentanyl (0.05 mg/kg body weight). Unconscious mice were fixed on an operation table. Ventral parts of the thorax were shaved, washed and sterilized. Unconscious mice were then intubated and ventilated with normal room air, using an animal respirator (TSE GmbH, Siemensstr. 21, 61352 Bad Homburg; product: http://tinateb.com/wp-content/uploads/2016/06/TSE_Respirator-Compact_20080724_HR.pdf).

For LAD operation, the thorax was opened about 1 cm above the *Processus xiphoideus* and about 1 cm left parasternally by dissecting the skin here. The below located M. pectoralis was moved to the sides without further injury to access the thorax wall. The intercostal muscles between two ribs were moved to the side without breaking the ribs. The thereby created intrathoracic access was widened by a surgical spreader inserted above the pericardium. The pericardium was opened surgically stump by using two anatomical forceps. The thymus, if present in the surgical field, was pushed to the side with a surgical swab to gain access to the aortic root. The heart was carefully moved out of the pericardium using a hook, and the left atrium was put to the side with a surgical swab. The LAD was then ligated with a 5.0 Prolene suture (Ethicon, see http://www.ethicon.com/healthcare-professionals/products/wound-closure/non-absorbable-sutures/prolene-polypropylene). The ligation was made close to the aortic root, and the suture was tightened until paleness of the coronary artery anterior wall was noted. After ligation, the thorax wall and then the skin were closed by a single button seam using a 4.0 Prolene suture (company: Ethicon).

As a control, sham operations were performed. For the sham control group, the procedure followed was exactly the same as described above, except that the 5.0 prolene suture was only loosely out around the LAD without tightening.

The operation is ended by extubation, and antagonizing the anesthesia by i.p. injection of Atipamezol (2.5 mg/kg body weight) and Flumazenil (0.5 mg/kg body weight). Mice were put onto a warming mate until waking up, and then were transferred back to animal cages. The time for the whole procedure above by expert staff was around 30 min.

One week after LAD ligation, echocardiography was performed in M-mode to confirm MI, i.e. the left ventricular end-diastolic (LVEDD) and systolic (LVESD) diameters were assessed to allow calculation of left ventricular (LV) fractional shortening (LVFS=[LVEDD_LVESDLVEDD]×100). Only mice with a large infarct (left ventricular ejection fraction (LVEF)<20%) were subsequently randomized into two groups, i.e. one group receiving normal chow (CHF, n=11) and a second group receiving chow supplemented with compound (0.1% of compound MyoMed-946, CHF+MyoMed-946, n=12). Sham operated animals received only normal chow (n=15). Nine weeks later, echocardiography was performed again.

TABLE 1

Animal characteristics after 10 weeks of intervention

|  | Sham (n=15) | CHF (n = 11) | CHF + MyoMed-946 (n = 12) |
|---|---|---|---|
| Physical |  |  |  |
| Body weight (g) | 22.6 ± 0.5 | 22.4 ± 0.6 | 23.8 ± 0.4 |
| Heart-to-body weight (g/mg) | 5.03 ± 0.11 | 7.87 ± 0.55*** | 7.52 ± 0.57*** |
| Lung weight (wet/dry) | 4.16 ± 0.07 | 4.48 ± 0.06* | 4.47 ± 0.10* |
| Histology |  |  |  |
| LV infarct size (%) | — | 30.5 ± 4.6 | 27.1 ± 2.9 |
| Echocardiography |  |  |  |
| LVEDD (mm) | 3.8 ± 0.1 | 6.2 ± 0.2*** | 5.9 ± 0.2*** |
| LVESD (mm) | 2.6 ± 0.1 | 5.8 ± 0.3*** | 5.3 ± 0.2*** |
| LVEF (%) | 59.6 ± 2.7 | 16.1 ± 2.9*** | 21.1 ± 2.5*** |
| LVFS (%) | 31.8 ± 1.9 | 7.5 ± 1.4*** | 9.9 ± 1.2*** |

*$P < 0.05$ vs. sham;
***$P < 0.001$ vs. sham.

The animals were sacrificed to collect tissues, in particular diaphragm tissue, for functional and molecular characterization. All experiments and procedures were approved by the local Animal Research Council, University of Leipzig, and the Landesbehörde Sachsen (TVV 36/15).

2.3 Contractile Function:

To provide a direct functional assessment, the contractility in skeletal muscle fiber bundles, i.e. fibre bundle from the diaphragm of MCT mice and CIF mice, was measured as follows. A fiber bundle from the diaphragm was isolated to allow in vitro contractile function to be assessed using a length-controlled lever system (301B, Aurora Scientific Inc., Aurora, Canada), as described by Bowen et al., FASEB J, 2017, 31. Briefly, a muscle bundle was mounted vertically in a buffer-filled organ bath (~22° C.), set at optimal length, and after 15 min was stimulated over a force-frequency protocol between 1-300 Hz (600 mA; 500 ms train duration; 0.25 ms pulse width). The muscle then underwent a force-velocity protocol whereby the muscle was allowed to shorten against external loads (80-10% of the maximal tetanic force; each separated by 1 min) after being stimulated at 150 Hz for 300 ms. Shortening velocity was determined 10 ms after the first change in length and on the linear section of the transient (DMA software, Aurora Scientific). Force (N) was normalized to muscle cross-sectional area (CSA; $cm^2$) by dividing muscle mass (g) by the product of $L_o$ (cm) and estimated muscle density (1.06), which allowed specific force in $N/cm^2$ to be calculated. Shortening velocity was normalized to optimal muscle length (in $L_o$/s), while power was calculated for each load as the product of shortening velocity and specific force (in $W/cm^2$).

Figure 27:
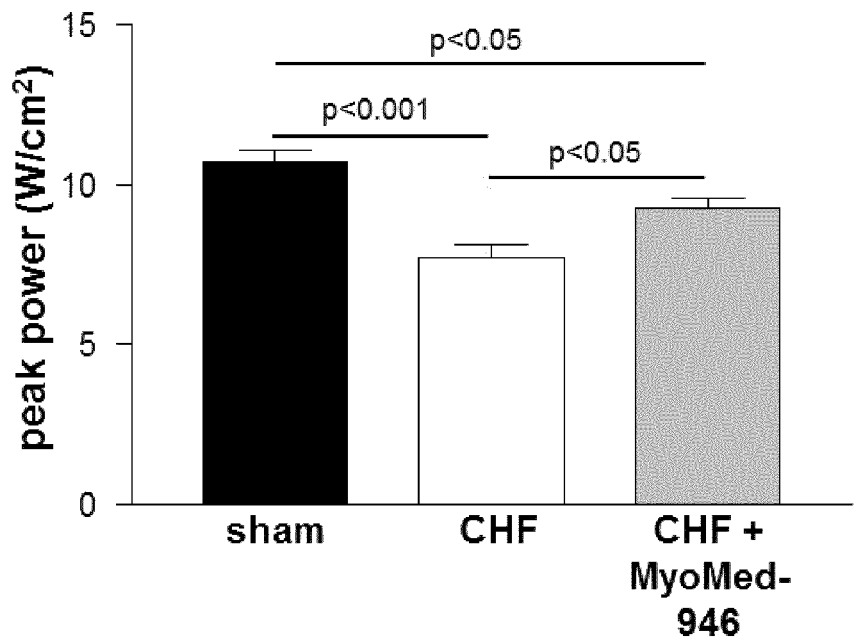

As can be seen from FIGS. 24 to 27, the diaphragm myofiber bundles from chronic heart failure mice (CHF mice) developed less force during electric stimulation (FIG. 24), and had also reduced maximal force (FIGS. 25 and 26) and peak power (FIG. 27). Thus, compared with sham animals, mice with CHF on control chow developed a diaphragm myopathy at week 10. Feeding with compound MyoMed-946 protected mice from such a post-infarct diaphragm weakness. The loss of diaphragm function and diaphragm maximal force due to chronic heart failure can be significantly reduced in mice fed with the compound MyoMed-946 compared to the untreated group of CHF mice. This indicates that the selective inhibition of MuRF1 by the compound MyoMed-946 mediates a benefit to diaphragm function after heart failure with reduced ejection fraction (HFrEF) induced by myocardial infarction.

Likewise, as can be seen from FIGS. 28 to 30 the contractile dysfunction of the diaphragm (in terms of shortening velocity and power) in mice suffering from MCT-induced pulmonary hypertension was also essentially prevented when the MCT mice were fed with the compound MyoMed-946 (MCT+MyoMed-946).

Collectively, therefore, the above findings suggest that the selective inhibition of MuRF1 by the compound MyoMed-946 mediates a benefit to both skeletal muscle quantity (i.e., mass) and quality (i.e. contractile function) in chronic heart failure and in cardiac cachexia.

2.4 Tumor Mouse Model:

8 weeks old female C57BL/6N mice were inoculated with B16F10 melanoma cells ($9 \times 10^5$ cells) or saline (sham, n=10). Within the first 3 days after tumor inoculation, the B16F10 mice as well as the sham mice received regular chow. Then the B16F10 mice were randomly divided in three groups, where the first group received MyoMed-946 chow (Tumor+MyoMed-946, n=10), the second group received MyoMed-205 chow (Tumor+MyoMed-205, n=10) and the third group received an identical chow but without the addition of the selected compounds (Tumor, n=10). The compound concentration in the chow was 0.1 weight-%, resulting in a daily compound intake per mouse of about 3 mg. Also the sham group was fed with an identical chow but without the addition of the selected compound. Wire-hang tests (muscle function) were performed with each mouse 9, 16 and 23 days after tumor inoculation. For this purpose, a standard wire hang construction was used with a wire (length: of 40 cm, diameter: 2.5 mm) at a height of 70 cm above the floor. Under the center of the wire a large box with sawdust was placed. For testing, the mouse was hung to the wire with the two limbs and hang time was recorded. Each animal had three attempts for 180 sec. max each. After three attempts, the maximal holding impulse was calculated (hanging time×body weight).

Mice were sacrificed 25 days after tumor inoculation. At sacrifice, examination and tissue analysis were performed as described above.

As can be seen from FIG. 31, tumor induced skeletal muscle atrophy (based on TA muscle weight) could be attenuated in the tumor+MyoMed-946 mice and the tumor+MyoMed-205 mice at least to certain extent when compared to the tumor mice. This effect is more pronounced in the wire-hang test (FIG. 32), where the administration of compounds MyoMed-946 and MyoMed-205 (tumor+MyoMed-946 mice and the tumor+MyoMed-205 mice) significantly attenuates the loss of muscle function compared to the tumor mice on normal diet.

2.5 Myocardial and Skeletal Muscle Alterations in Heart Failure with Preserved Ejection Fraction (HFpEF)—Rat Model A schematic drawing of the study design is shown in FIG. 56. For this test, ZSF1 rats were used. After 20 weeks of age, ZSF1 rats lose diastolic compliance, leading to increased end-diastolic volumes, and thus mimic human HFpEF (also known as diastolic heart failure.

Female ZSF1 lean (control, n=25) and ZSF1 obese (n=40) rats were included into the study. At the age of 20 weeks the development of HFpEF was confirmed by echocardiography/invasive hemodynamic measurements, and tissue material from a subset of animals were collected (control n=10; ZSF1 obese n=10). The remaining control rats (control, n=15) were kept sedentary for another 12 weeks whereas the remaining ZSF1 obese animals (n=30) were randomized into the following groups: (1) rats receiving normal chow (HFpEF group, n=15) or chow supplemented with compound MyoMed-205 (0.1% of MyoMed-205, HFpEF+MyoMed-205, n=15). Rats were exposed to identical conditions in a 12 h light/dark cycle, with food and water provided ad libitum. Twelve weeks after randomization, echocardiography and invasive hemodynamic measurements were performed to elucidate the degree of diastolic dysfunction. Rats were subsequently sacrificed (opening of the chest in deep anesthesia), and skeletal muscle and myocardial tissue was harvested for functional and molecular analyses (formalin fixation and snap frozen in liquid nitrogen). All experiments and procedures were approved by the local animal research council, TU Dresden and the Landesbehörde Sachsen (TVV 42/2018).

Echocardiography

Rats were anesthetized by isoflurane (1.5-2%) and transthoracic echocardiography was performed using a Vevo 3100 system and a 21-MHz transducer (Visual Sonic, Fujifilm) to assess cardiac function as previously described (T. S. Bowen et al., Eur. J. Heart Fail., 2015, 17, 263-272). For systolic function, B- and M-Mode of parasternal long- and short axis were measured at the level of the papillary muscles. Diastolic function was assessed in the apical 4-chamber view using pulse wave Doppler (for measurement of early (E) and atrial (A) waves of the mitral valve velocity) and tissue Doppler (for measurement of myocardial velocity (E' and A')) at the level of the basal septal segment in the septal wall of the left ventricle. Functional parameters (i.e. LV ejection fraction (LVEF) and stroke volume (SV)) and ratios of [E/E'] and [E/A]) were obtained using the Vevo LAB 2.1.0 software.

Invasive Hemodynamic Measurements

Invasive hemodynamic pressure measurements were performed as the terminal procedure. In anesthetized (ketamine, xylazine) but spontaneous breathing rats the right carotid artery was cannulated with a Rat PV catheter (SPR-838, ADInstruments Limited) which was gently placed in the middle of the left ventricle. The LV end-diastolic and end-systolic pressure, maximum rate of pressure rise (dP/dtmax), maximum rate of pressure fall (dP/dtmin), and time constant ($\tau$) for LV relaxation, after which withdrawal of the catheter into the aorta followed, and phasic and mean arterial pressures were measured. Mean arterial pressure was measured in the ascending aorta. Data were recorded in LabChart8 software (ADInstruments).

Skeletal Muscle Function

The right EDL and the left soleus were dissected and mounted vertically in a Krebs-Henseleit buffer-filled organ bath between a hook and force transducer, with the output continuously recorded and digitized (1205A: Isolated Muscle System—Rat, Aurora Scientific Inc., Ontario, Canada). In vitro muscle function was assessed by platinum electrodes stimulating the muscle with a supra-maximal current (700 mA, 500 ms train duration, 0.25 ms pulse width) from a high-power bipolar stimulator (701C; Aurora Scientific Inc., Ontario, Canada). The muscle bundle was set at an optimal length (Lo) equivalent to the maximal twitch force produced, after which bath temperature was increased to 25° C. and a 15-minute thermos equilibration period followed. A force-frequency protocol was then performed at 1, 15, 30, 50, 80, and 120 Hz, separated by 1-minute rest intervals. After a 5-minute rest period, the muscles then under-went a fatigue protocol over 5 minutes (40 Hz every 2 seconds). Forces generated during the fatigue protocol were normalized to the initial force generated to provide a relative assessment of fatigability.

Results:

Animal Characteristics at 20 Weeks (Time Point of Randomization)

To verify the development of HFpEF before the animals were randomized into the different treatment groups, 10 ZSF1-lean and 10 ZSF1-obese animals were analyzed by echocardiography, invasive hemodynamic measurements and measurements of skeletal muscle function. The ZSF1-obese animals exhibited an increased body weight (sign of obesity), and signs of myocardial hypertrophy (increased heart weight when normalized to tibia length) were evident. With respect to markers for diastolic function the ratio E/6 and the left ventricular end-diastolic pressure (LVEDP) were significantly increased in the ZSF1-obese animals. Despite of a disturbance of diastolic function, left ventricular ejection fraction (LVEF) was normal (>60%) and even a little bit higher when compared to the lean control rats. With respect to mean arterial blood pressure (MABP) a significant elevation was seen in the ZSF1-obese animals. This increase in MABP is a sign of a hypertonic state in the animals, a feature which is well known from HFpEF patients. With respect to the peripheral skeletal muscle, the ZSF1-obese animals developed muscle atrophy and skeletal muscle dysfunction. In summary, the animals at an age of 20 week developed features which are in accordance with the diagnosis of HFpEF.

Impact of MyoMed-205 Treatment on Cardiac Parameters in HFpEF

To evaluate the impact of MyoMed-205 on myocardial function echocardiography and invasive hemodynamic measurements were performed. As shown in FIG. 57, the left ventricular ejection fraction (LVEF) (FIG. 57A) was significantly reduced in the non-treated HFpEF animals when compared to the control ZSF1-lean animals. This reduction is significantly attenuated by the 12 week treatment with MyoMed-205. With respect to the parameters for diastolic function, the ratio E/6 (FIG. 57B) and LVEDP (FIG. 57C), the treatment with MyoMed-205 attenuated the increase seen in the ZSF1-obese untreated animals. No treatment effect of MyoMed-205 was seen MABP (FIG. 57D). Taken together, these results show that the treatment with MyoMed-205 improved systolic as well as diastolic function significantly and this effect is not mediated by modulating the blood pressure.

Impact of MyoMed-205 Treatment on Skeletal Muscle Mass and Function

The skeletal mass and skeletal muscle function was already impaired in the ZSF1-obese animals at the time point of randomization into the different treatment groups. The present test examined whether MyoMed-205 was able to modulate skeletal muscle mass and function. The results can be seen in FIG. 58. Analysis of the muscle weight of the tibialis anterior muscle (TA) (FIG. 58A) revealed a significant drop in muscle wet weight in the HFpEF untreated animals. This muscle atrophy was attenuated by MyoMed-205. With respect to the EDL (FIG. 58C) and soleus muscle (FIG. 58B) the development of HFpEF had no impact on muscle wet weight. However, in the EDL muscle the treatment with MyoMed-205 resulted in a small but significant increase in muscle weight (FIG. 58C).

Besides measuring muscle weight for the development of muscle atrophy, the assessment of muscle function is very important. As shown in FIG. 58D, ZSF1-obese animals which were not treated develop a skeletal muscle dysfunction when compared to the ZSF1-lean control group. This drop in muscle force is evident in the soleus muscle (FIG. 58D) when measuring the absolute specific muscle force. Treating the HFpEF animals for 12 weeks with MyoMed-205 resulted in an attenuation of functional loss.

Conclusion

The results show that in HFpEF MyoMed-205 attenuates the development of myocardial diastolic dysfunction and attenuates skeletal muscle atrophy and skeletal muscle dysfunction.

2.6 Doxorubicin-Induced Muscle Atrophy and Cardiac Toxicity

Doxorubicin (DOX) is an efficient chemotherapeutic drug used in various cancer treatments. However, its use is associated with early and chronic cardiotoxicity and myotoxicity. In rodents, a single injection of Doxorubicin is capable of reducing heart and skeletal muscle mass, followed by a marked impairment of function.

The effects of MyoMed-205 enriched food in a mouse model that was treated with Doxorubicin was evaluated. C57bl/6 mice were acclimated at the vivarium for three days, then randomly sorted into four groups, as follows: 1. Control (placebo food+0.9% saline i.p. injections); 2. MyoMed-205 (MyoMed-205-food, food supplemented with 1 g/kg MyoMed-205; +0.9% saline injections); 3. DOX (placebo food+DOX injections): 4. DOX+MyoMed-205 (MyoMed-205 food+DOX injections). Animals were pre-fed with either MyoMed-205 food or placebo for seven days before the first DOX injection. DOX treatment was at a total dosage of 25 mg/kg, given in five injections at days 10, 12, 16, 25, and 28, respectively. Animals' weight and food intake were measured daily at the same hour of the day to assess food consumption and weight gain. Cardiac functions were evaluated at days 19 and 42 by echocardiography. As shown in FIG. 59, feeding with MyoMed-205 was capable to reduce features of cachexia wasting and body stress markedly by day 43: MyoMed-205-fed mice had higher lean mass (FIG. 59A), retained more body fat (FIG. 59B), and had about two-fold less interstitial edema free liquids (FIG. 59C). * means $p<0.05$ v. control; $ means $p<0.05$ vs. MyoMed-205; § means $p<0.05$ vs. DOX+MyoMed-205 (Tukey post-test).

Echocardiography at day-15 and after 25 mg/Kg accumulated DOX dosage indicated cardiac toxicity and failure, as can be seen from FIG. 60, i.e. a decreased heart weight (corrected by tibial length) (FIG. 60C), reduced ejection fractions (calculated from long axis plan) (FIG. 60A), and reduced fractional shortening (calculated from short axis plan) (FIG. 60B), respectively. MyoMed-205 treatment until day 43 prevented this. In summary, administration of MyoMed-205 during DOX chemotherapy is useful to protect the heart. * means $p<0.05$ v. control; $ means $p<0.05$ vs. MyoMed-205; § means $p<0.05$ vs. DOX+MyoMed-205 (Tukey post-test).

2.7 Muscle Function in Obese Mice with Type 2 Diabetes During Diet-Induced Weight Loss (DIO Mouse Model: Diabetes with Insulin Resistance and Obesity)

The effects of compound-feeding in a mouse model for diabetes that also develops myopathy during the progression of diabetes were tested. Diabetes was induced by a high-fructose high-fat diet (HFD) for 4 months in DIO mice. The body weight gain was 22.2%. The mice developed increased fasting glucose and insulin resistance. Control group animals received a normal rodent diet (regular diet). Weight loss was then induced during a 30 days test period. In a first stage, the animals were fed normal rodent diet for 16 days. Then in a second stage the animals received a low-calory diet for 14 days. The body weight decreased by 12.4% on average at the endpoint. Two days after start of the first stage, the diet was supplemented with MyoMed-205 (at 1 g compound/1 kg food). At start of the first stage and then at days 3, 7, 14, 21 and 28 of the test period, compound-fed and control mice were compared for their muscle strength by wire hang tests.

Test design: ICR-DIO male mice were randomly assigned to groups of 8-10 animals each. Three control groups were included: Control group of mice without obesity (Control; regular diet (RD); n=10), obese mice fed with high-fructose high-fat diet during the entire study period (DIO HFD; n=8); and obese mice with initiated weight loss (DIO control; n=8).

Wire hang test: For the wire hang tests (WHT), a standard wire hang construction was used with a wire (length: of 40 cm, diameter: 2.5 mm) at a height of 70 cm above the floor. Under the center of the wire a large box with sawdust was placed. For testing, the mouse was hung to the wire with the two limbs and the time that mice were able to hold onto the wire before falling off was recorded. Each animal had three attempts for a maximum of 180 sec. After the three attempts, the maximal holding impulse was calculated (hanging time× body weight).

Results:

| Groups | Observed effects on muscle strength in wire hang test (WHT) |
|---|---|
| 1 Control (RD) | No effect on WHT, control group |
| 2 DIO control | Decreased WHT performance, compared to group 1 |
| 3 DIO HFD | Decreased WHT performance, compared to groups 1 and 2 |
| 5 MyoMed-205-treated DIO | Significant improvement of muscle strength in WHT by week 4 compared to groups 2 and 3 |

FIG. 61 is the graphical illustration of the results of the WHT of MyoMed-205-treated DIO mice as compared to DIO control mice. As can be seen, MyoMed-205 significantly improved the muscle strength as compared to DIO control mice by week 4 (28 days). The muscle strength was also improved significantly as compared to DIO HFD mice and did not differ significantly from the control (RD) mice group by week 4 (not shown in FIG. 61).

2.8 Glucose and Insulin Regulation in Obese Mice with Type 2 Diabetes During Diet-Induced Weight Loss (DIO Mouse Model: Diabetes with Insulin Resistance and Obesity)

Analogously to example 2.7, diabetes was induced by a high-fructose high-fat diet (HFD) for 4 months in DIO mice. The mice developed increased fasting glucose and insulin resistance. Control group animals received a normal rodent diet (regular diet). Weight loss was then induced during a 30 days test period. In a first stage, the animals were fed normal rodent diet for 16 days. Then in a second stage the animals received a low-calorie diet for 14 days. Two days after start of the first stage, the diet was supplemented with MyoMed-203 (at 1 g compound/1 kg food).

Test design: ICR-DIO male mice were randomly assigned to groups of 8-10 animals each. Three control groups were included: Control group of mice without obesity (control; regular diet (RD); n=10), obese mice fed with high-fructose high-fat diet during the entire study period (DIO HFD; n=8); and obese mice with initiated weight loss (DIO control; n=8).

Determination of Blood Glucose Level

Determining the level of blood glucose was performed after 6-hour fasting. An On Call Plus glucometer (Acon Laboratories, Inc., USA) and specific test strips (REF G133-111) were used for determination of glucose levels. Blood was obtained from the tail vein by incision of the tail tip. 5-6 µl of blood were used for each assay.

In MyoMed-203-treated animals, the blood glucose level was significantly lower compared with the DIO control group throughout the treatment period where the fasting blood glucose value significantly changed on the $2^{nd}$ and $21^{st}$ day of the study. FIG. 62 shows the comparison of MyoMed-203-treated DIO mice with DIO control mice.

Glucose Tolerance Test

For oral glucose tolerance test (OGTT), mice were orally treated with glucose at dose of 2 g/kg at the dose volume of 10 ml/kg after a 6-hour fasting. Glucose measurements were performed immediately before treatment and at 15, 30, 60 and 120 min after glucose administration. The AUC describing the rate of blood glucose output in each mouse during the test was calculated using the formula:

$$S = \int_a^b f(x)\,dx$$

MyoMed-203 showed mild hypoglycemic effect in obese mice after 14 days of weight loss and treatment according to OGTT data. Blood glucose levels in the animals of this group tended to be lower at 30 minutes of OGTT test compared to DIO control group. The same is true for the calculated AUCs describing glucose elimination. A similar trend continued in the $28^{th}$ day of the study: significant decrease in the glucose level at 120 min was observed in MyoMed-203 treated group compared with all control groups; the calculated area under the glucose elimination curve tended to be lower as well. FIG. 63 and FIG. 64 show the OGTT data at days 14 and 28, respectively, of MyoMed-203-treated DIO mice and DIO control mice.

Test of Tolerance to Insulin Action

For insulin tolerance test (ITT), mice were injected intraperitoneally with recombinant human insulin solution (Lilly, France; REF C620001K) at the dose of 0.75 or 0.60 IU/g of body weight in the volume of 5 ml/kg after 6-hour fasting. Glucose measurements were performed immediately before treatment and at 15, 30, 60 and 120 min after insulin administration. The results of the rate of blood glucose output were expressed as area under the curve (AUC).

A significant decrease of glucose level was observed in MyoMed-203-treated mice at 120 minutes after insulin injection compared with all control groups. FIG. 65 shows the ITT results in MyoMed-203-treated DIO mice and DIO control mice.

3. Tissue Analyses
3.1 Proteomic and Western Blot Analysis:
3.1.1 MCT Mice:
Proteomic Analysis:

Proteins from frozen diaphragm samples in sham, MCT, and MCT+compound mice (n=3 per group) were powdered under liquid $N_2$. Mass spectrometry was then performed at the DZHK mass spectrometry core facility at Bad Nauheim, as described in Konzer et al., Methods in molecular biology, 2013, 1005, 39-52. The relative ratios for MCT/sham and MCT+compound/MCT were determined, with only hits deemed to be differentially expressed and highly significant (P<0.01) further studied by Western blot.

Western Blot Analysis:

The Western blot analyses consisted of frozen TA muscle samples being homogenized in RIPA buffer (50 mmol/L Tris, 150 mmol/L sodium chloride, 1 mmol/L EDTA, 1% NP-40, 0.25% sodium-deoxycholate, 0.1% SDS, 1% Triton X-100; pH 7.4) or relax buffer (90 mmol/L HEPES, 126 mmol/L potassium chloride, 1 mmol/L MgCl, 50 mmol/L EGTA, 8 mmol/L ATP, 10 mmol/1 Creatinephosphate; pH 7.4) containing a protease inhibitor mix (Inhibitor mix M, Serva, Heidelberg, Germany), sonicated, and centrifuged at 16,000×g for 5 min. Protein concentration of the supernatant was determined (BCA assay, Pierce, Bonn, Germany) and aliquots (5-20 μg) were separated by SDS-polyacrylamide gel electrophoresis. Proteins were transferred to a polyvinylidene fluoride membrane (PVDF) and incubated overnight at 4° C. with the following primary antibodies: MAFbx (1/2000, Eurogentec, Seraing, Belgium), MuRF1 (1/1000, Myomedix Ltd., Neckargemünd, Germany), CARP (1/500, Myomedix Ltd., Neckargemünd, Germany), BAX (1/1000; Abcam, Cambridge, UK), and eIF2B-delta (1/200; Santa Cruz Biotechnolgy, Santa Cruz, USA). Membranes were subsequently incubated with a horseradish peroxidase-conjugated secondary antibody and specific bands visualized by enzymatic chemiluminescence (Super Signal West Pico, Thermo Fisher Scientific Inc., Bonn, Germany) and densitometry quantified using a 1D scan software package (Scanalytics Inc., Rockville, USA). Blots were then normalized to the loading control GAPDH (1/30000; HyTest Ltd, Turku, Finland). All data are presented as fold change relative to sham.

The expression levels of 5 proteins were found to specifically respond to the compound, as indicated by comparison of the MCT and MCT+MyoMed-946 proteomes. The expression levels of these proteins are summarized in Table 2.

et al., *J Am Coll Cardiol*, 1999, 33, 959-965 and Vescovo et al., *Heart*, 2000, 84, 431-437). Indeed, it has been noted before that BAX is elevated in cardiac cachexia and associated with an increased MuRF1 expression (see for example Dalla Libera et al., *Am J Physiol Cell Physiol*, 2004, 286, C138-144 and Rezk et al., PLoS One, 2012, 7, e30276).

As can be further seen from FIGS. 36 to 38, the proteomic analysis confirmed that the increased protein expression of MuRF1 in MCT mice is prevented by the compound MyoMed-946 yet no effects were observed for MAFBx (another key atrogin E3 ligase). This indicates the underlying mechanism of the compound appears to be MuRF1 specific, which would be expected based on the preliminary in vitro studies. MuRF1 is also known to interact with numerous substrates, with one in particular being CARP (a member of the muscle ankyrin repeat proteins (MARP) family), which is a purported nuclear- and sarcomere(titin)-based protein with transcriptional functions (see for example Miller et al., *J Mol Biol*, 2003, 333, 951-964). CARP is known to be upregulated in stress-related conditions and is associated with contractile dysfunction and muscle atrophy (see for example Laure et al., *The FEBS* journal, 2009, 276, 669-684 and Moulik et al., *J Am Coll Cardiol*, 2009, 54, 325-333). In line with such evidence, an increase in CARP expression in MCT-stressed mice is observed, while this effect is abolished in the MyoMed-946 fed mice, suggesting that this compound may blunt CARP expression via its inhibition on MuRF1, which in turn may contribute to maintenance of muscle mass and function.

3.1.2 CHF Mice:

To analyze the molecular mechanisms underlying the observed physiological changes and benefits of MyoMed-946-treated mice suffering from CHF, comparative quanti-

TABLE 2

| Gen | Function | Group | P-value | Protein Ratio ($\log_2$) | $-\log_{10}$ P value |
|---|---|---|---|---|---|
| eIF2B4 | protein synthesis | MCT/sham | 0.005 | −0.46 | 2.29 |
|  |  | MCT + MyoMed-946/MCT | 0.005 | 0.32 | 2.28 |
| AS3MT | methylation | MCT/sham | 0.008 | 0.16 | 2.09 |
|  |  | MCT + MyoMed-946/MCT | 0.009 | −0.31 | 2.05 |
| ATPAF1 | oxidative phosphorylation | MCT/sham | 0.006 | 0.27 | 2.26 |
|  |  | MCT + MyoMed-946/MCT | 0.001 | −0.68 | 3.69 |
| GHDC | unknown | MCT/sham | 0.005 | 0.54 | 2.32 |
|  |  | MCT + MyoMed-946/MCT | 0.005 | −0.39 | 2.33 |
| BAX | apoptosis | MCT/sham | 0.005 | 0.97 | 2.28 |
|  |  | MCT + MyoMed-946/MCT | 0.006 | −0.73 | 2.25 |

This included an upregulation of eIF2B (delta subunit) and downregulation of BAX, which was subsequently confirmed by immunoblotting, as can be seen from FIGS. 33 to 35. The eIF2B pathway is a known translational regulator of protein synthesis. eIF2B was previously identified as a MuRF1 interacting factor, suggesting that MuRF1-mediated a depletion of the translation initiation factor eIF2B under MCT stress, but this was relieved by the compound. In addition, the compound also modulated the pro-apoptotic regulator BAX, with this protein upregulated in MCT mice compared to shams and normalized in the MCT+MyoMed-946 group. In human patients with chronic heart failure, apoptosis is increased in skeletal muscle and is closely correlated to the degree of atrophy (see for example Adams tative proteomic analysis as well as Western blot analysis of diaphragm tissue from sham, CHF, and CHF+MyoMed-946-treated mice were performed.

Proteomic Analysis:

Mass spectrometry-based proteomic analysis was performed at the DZHK Core Facility, Bad Nauheim, Germany. Obtained MS raw data were processed by MaxQuant (1.6.0.1) using the Andromeda search engine and the Uniprot database for *Mus musculus* (as of 20 Apr. 2017). At a false discovery rate of 1% (both peptide and protein levels), >2600 protein groups were identified. The reductive dimethylation protocol employed (see Boersema et al., *Nat Protoc*, 2009, 4, 484-494) yielded pairwise relative comparative quantitation (ratios) between proteins from CHF+

MyoMed-946, CHF, and sham conditions, which were statistically queried for significant differences using standard statistical tests. Several proteins were identified to be statistically different (e.g. TNNT3, Timm9, Ccdc5, Adi1, Ptges3, and Ndufa3). After applying multiple hypothesis testing (Benjamini-Hochberg; corrected P<0.05) for comparison of CHF mice with and without compound feeding, only Mrps5 (mitochondrial ribosomal protein 5), a mitochondrial-cytosolic shuttle protein in charge of protein initiation and elongation in the mitochondrial ribosome, remained as a significantly up-regulated protein (P=0.02; FIG. 4A) and was further studied by Western blot analysis as described below.

As can be seen from FIG. 39, Western blot analysis of the diaphragm of all animals included into the CHF study reveals a significant reduction of Mrps5 expression in the CHF group in comparison with the sham control group, which was reversed by compound MyoMed-946 feeding. Data are presented as mean±standard error of the mean.

Western Blot Analysis:

For western blot analyses, frozen diaphragm was homogenized in relaxing buffer (90 mmol/L HEPES, 126 mmol/L potassium chloride, 36 mmol/L sodium chloride, 1 mmol/L magnesium chloride, 50 mmol/L EGTA, 8 mmol/L ATP, and 10 mmol/L creatine phosphate, pH 7.4) containing a protease inhibitor mix (Inhibitor Mix M, Serva, Heidelberg, Germany) and sonicated. Protein concentration of the supernatant was determined (bicinchoninic acid assay, Pierce, Bonn, Germany), and aliquots (5-20 µg) were separated by sodium dodecyl sulfate-polyacrylamide gel electrophoresis. Proteins were transferred to a polyvinylidene fluoride membrane and incubated overnight at 4° C. using the following primary antibodies: porin and telethonin (both 1/1000, Abcam, Cambridge, UK), MRPS-5 (1/500, Thermo Fisher, Rockford, IL, USA), MuRF1 and MuRF2 (both 1/1000; commercially available from Myomedix, Neckargemünd, Germany), and Tom20 (1:200, Santa Cruz Biotechnologies, Heidelberg, Germany). Membranes were subsequently incubated with a horseradish peroxidase conjugated secondary antibody, specific bands were visualized by enzymatic chemiluminescence (Super Signal West Pico, Thermo Fisher Scientific Inc., Bonn, Germany), and densitometry was quantified using a one-dimensional scan software package (Scanalytics Inc., Rockville, MD, USA). Measurements were normalized to the loading control GAPDH (1/30000; HyTest Ltd, Turku, Finland) or α-tubulin (1:1000, Santa Cruz Biotechnologies). All data are presented as fold change relative to sham.

As can be seen from FIGS. 40 to 42, MuRF1 and MuRF2 expression is significantly up-regulated in the CHF group, and this was prevented by treatment with compound MyoMed-946 (FIGS. 40 and 41). Quantifying the expression of telethonin, a MuRF1 target protein, a trend (P=0.08) towards a reduced expression in the CHF group was observed, which was not evident in the compound MyoMed-946-treated group (FIG. 42).

3.1.3 B16F10 Mice (Tumor Mice):

Protein expression of MuRF1, Nox 2 and LC3 I/II in muscle tissue of B16F10 mice was determined as described above for the MCT and CHF mice. In addition, the level of the reactive oxygen species marker nitrotyrosine was determined.

Figure 43:
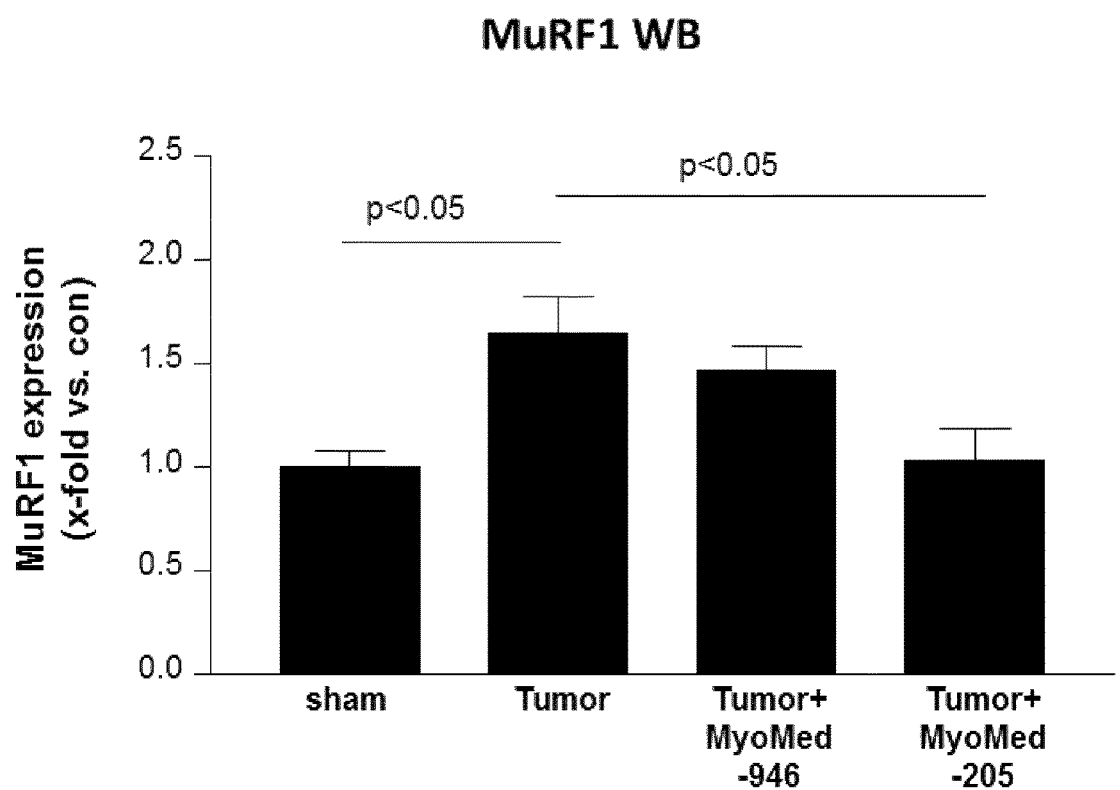
Figure 44:
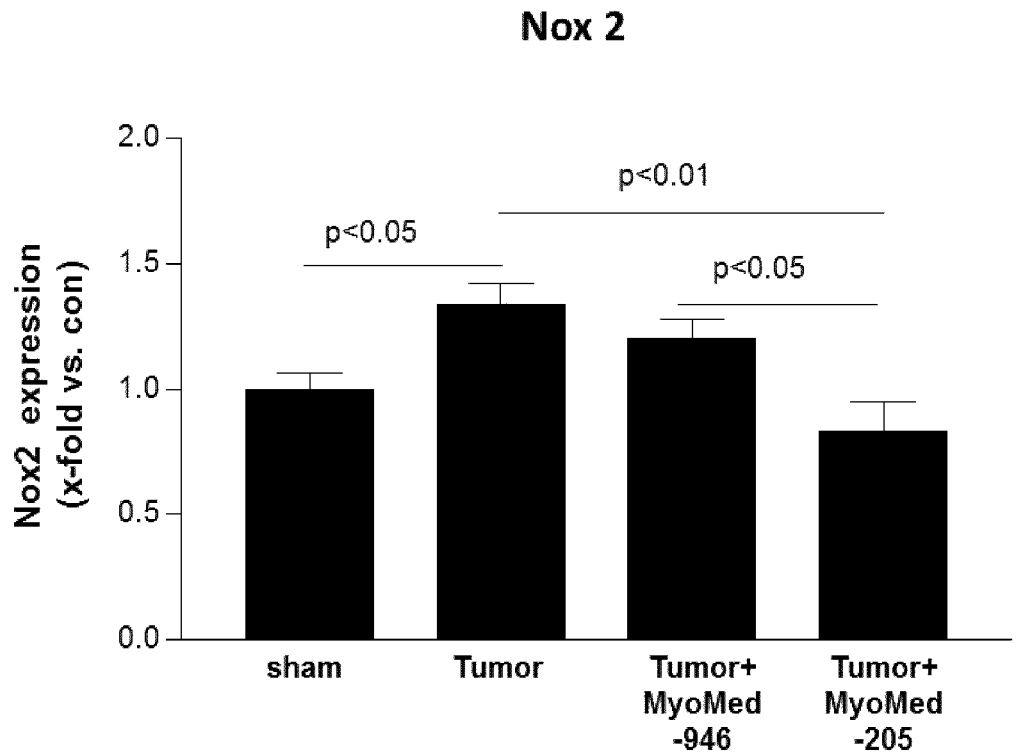
Figure 45:
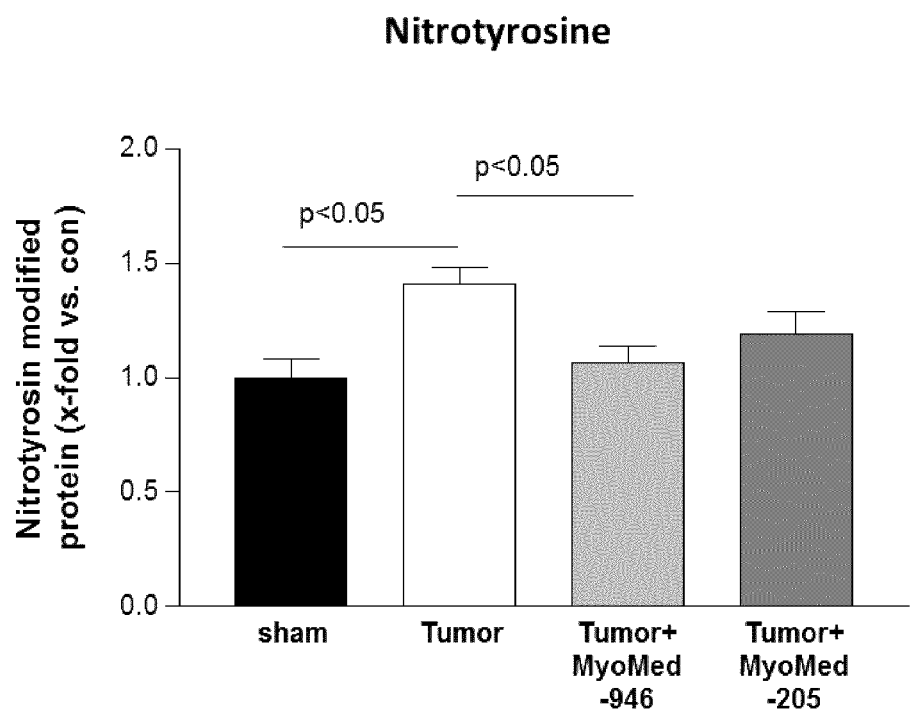
Figure 46:
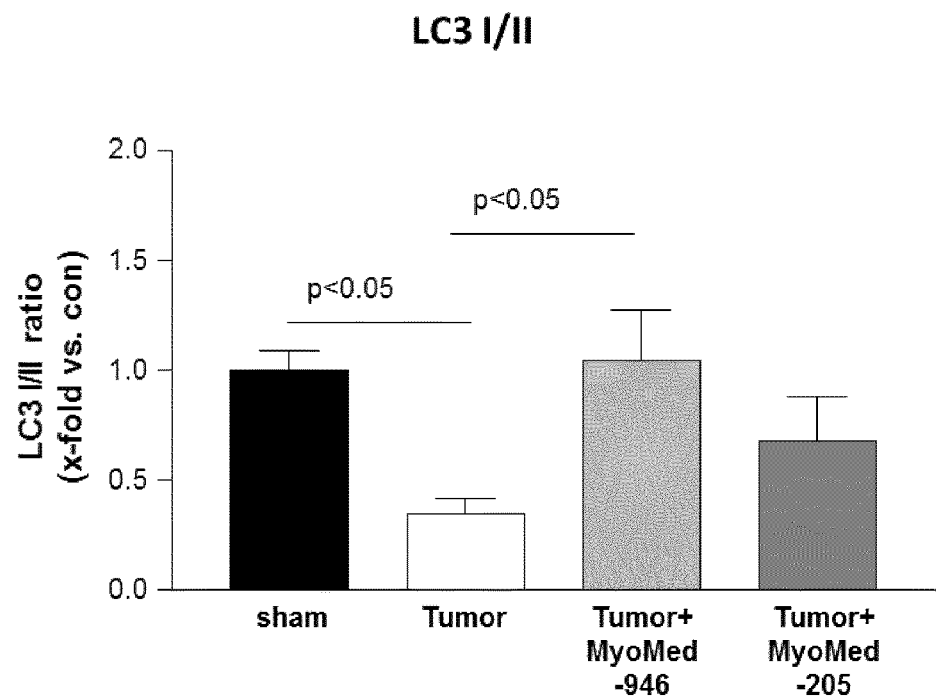

As can be seen from FIGS. 43 to 46, MuRF1 expression is significantly up-regulated in the tumor group, and this was prevented by treatment with compounds MyoMed-946 and MyoMed-205 (FIG. 43). Furthermore, the expression of Nox 2, which is a known endogenous reactive oxygen species (ROS), as well as the tissue level of nitrotyrosine is also significantly up-regulated in the tumor mice group, whereas in the tumor+MyoMed-946 and in the tumor+MyoMed-205 mice groups the amounts of these species are significantly reduced in the muscle tissue (FIGS. 44 and 45). On the other hand, the expression levels of LC3 I/II, which are key proteins involved in autophagocytosis, are down-regulated in the tumor group, which is not observed in the the tumor+MyoMed-946 and in the tumor+MyoMed-205 groups (FIG. 46).

3.2 Enzyme activity measurements:

3.2.1 CHF mice:

Since proteomic profiling data suggests an impaired mitochondrial homeostasis, the enzymatic activities of key mitochondrial enzymes in the diaphragm tissue of CHF mice were measured.

Diaphragmatic tissue was homogenized in relaxing buffer, and aliquots were used for enzyme activity measurements. Enzyme activities for lactate dehydrogenase (EC 1.1.1.27), pyruvate kinase (EC 2.7.1.40), succinate dehydrogenase (SDH, EC 1.3.5.1), citrate synthase (CS, EC 2.3.3.1), β-hydroxyacyl-COA dehydrogenase (EC 1.1.1.35), and mitochondrial complex I were measured spectrophotometrically as previously described in detail (Mukherjee et al., J Biol Chem, 1976, 251, 2155-2160; Vanderlinde et al., Ann Clin Lab Sci, 1985, 15, 13-31; Dzeja et al., Mol Cell Biochem, 1999, 201, 33-40; Takashi et al., Biochim Biohphys Acta, 1979, 574, 258-267; Schwarzer et al., J Physiol, 2014, 592, 3767-3782). Enzyme activity data are presented as the fold change relative to sham.

As can be seen from FIGS. 47 to 51 the enzyme activity of mitochondrial enzymes including citrate synthase (FIG. 47), succinate dehydrogenase (FIG. 48), and mitochondrial complex I (FIG. 49) is significantly reduced by 21, 28, and 27%, respectively, in the diaphragm of CHF animals when compared with sham. No difference was noted for creatine kinase. The amount of mitochondria in diaphragm tissue, as assessed by the protein expression of the mitochondrial porin expression (FIG. 50) and TOM-20 (FIG. 51), was also significantly reduced in CHF mice. Consistent with effects on mitochrondrial functions, treatment with compound MyoMed-946 partially improved citrate synthase, succinate dehydrogenase, and mitochondrial complex I enzyme activity (FIGS. 47 to 49) and resulted in near-normal porin and a modest, but statistically significant, improvement in TOM-20 expression (FIGS. 50 and 51).

In contrast, when assessing cytoplasmic enzymes for glycolysis and fatty acid metabolism (glycolysis: pyruvate kinase and lactate dehydrogenase; fatty acid metabolism: β-hydroxyacyl-COA dehydrogenase), no difference was detected between these three groups.

3.2.2 B16F10 Mice (Tumor Mice):

The enzyme activities of citrate synthase and mitochondrial complex I in muscle tissue of B16F10 inoculated mice were determined as described above for the CIF mice.

As can be seen from FIGS. 52 and 53, the enzyme activities of the mitochondrial enzymes citrate synthase (FIG. 52) and mitochondrial complex I (FIG. 53) are significantly reduced in the muscle tissue of the tumor group when compared with sham. Treatment with compounds MyoMed-946 and MyoMed-205 partially or complete restores the citrate synthase and mitochondrial complex I enzyme activities in the muscle tissue of B16F10 inoculated mice (FIGS. 52 and 53).

4. C2C12 Myotube Cell Culture, Reverse Transcription PCR

C2C12 myotubes were incubated with or without compound MyoMed-946 for 20 min at a final concentration of 10 µmol/L. After the incubation period, Total RNA was isolated from C2C12 cells and reverse transcribed into cDNA using random hexamers and Sensiscript reverse transcriptase (Qiagen, Hilden, Germany). An aliquot of the cDNA was used for quantitative RT-PCR, applying the Light Cycler system (Roche Diagnostics, Mannheim, Germany). The expression of specific genes was normalized to the expression of hypoxanthin-phosphoribosyl-transferase (HPRT)-mRNA. For quantification of MuRF-1 expression fluorescence resonance energy transfer (FRET) technology was applied using the following primers (TIB MolBiol, Berlin, Germany) and conditions: HPRT: 5'-CTCATggACTgAT-TATggACAggAC-3' (SEQ IN NO:1) and 5'-gCAggTCAgCAAAgAACTTATAgCC-3' (SEQ ID NO:2), 60° C. annealing; MuRF-1: 5'-gATgTgCAAggAACACgAA-3' (SEQ ID NO:3), 5'-CCTTCACCTggTggCTATTC-3' (SEQ ID NO: 4), LC640-gCACAAggAgCAAgTAggCACCTCAC-PH (SEQ ID NO: 5), 5'-gCCTggTgAgCCCCAAACACCT-FL (SEQ ID NO:6), annealing 58° C. LC640 stands for LC Red 640, a fluorescent dye. FL stands for fluorescein. PH stands for a phosphate group (blocks the free 3-hydroxyl group against undesired extension by the polymerase).

As can be seen from FIG. 54, the increased protein expression of MuRF1 in MCT mice was prevented by the compound MyoMed-946.

5. Statistical Analysis:

Data are presented as mean±SEM. One-way analysis of variance (ANOVA) followed by Bonferroni post hoc was used to compare groups, while two-way repeated measures ANOVA followed by Bonferroni post hoc was used to assess contractile function (GraphPad Prism). Significance was accepted as $P<0.05$.

The invention claimed is:

1. A compound of the general formula I

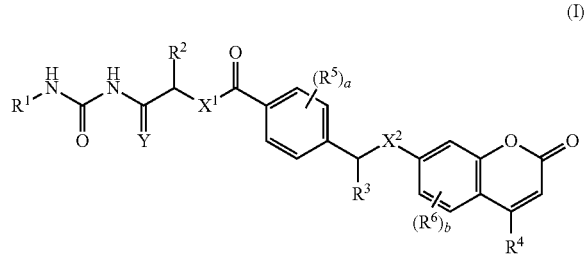

(I)

wherein $R^1$ is hydrogen or a group —$CH_2R^{1a}$, where $R^{1a}$ is selected from the group consisting of hydrogen, $C_1$-$C_3$-alkyl, phenyl, where phenyl is unsubstituted or may carry 1, 2 or 3 radicals independently selected from halogen, cyano, $C_1$-$C_3$-alkyl, $C_1$-$C_3$-haloalkyl and $C_1$-$C_3$-alkoxy; and a 5- to 10-membered heteroaromatic ring containing 1 to 4 heteroatoms or heterogroups independently selected from the group consisting of N, $NR^c$, O and S as ring member, where the 5- to 10-membered heteroaromatic ring is unsubstituted or may carry 1, 2 or 3 radicals $R^7$;

$R^2$ is selected from the group consisting of hydrogen, methyl and fluorinated methyl;

$R^3$ is selected from the group consisting of hydrogen, methyl and fluorinated methyl;

$R^4$ is selected from the group consisting of hydrogen and $C_1$-$C_4$-alkyl;

each $R^5$ is independently selected from the group consisting of halogen, cyano, $C_1$-$C_3$-alkyl, $C_1$-$C_3$-haloalkyl, $C_1$-$C_3$-alkoxy and $C_1$-$C_3$-haloalkoxy;

each $R^6$ is independently selected from the group consisting of halogen, cyano, $C_1$-$C_3$-alkyl, $C_1$-$C_3$-haloalkyl, $C_1$-$C_3$-alkoxy and $C_1$-$C_3$-haloalkoxy;

each $R^7$ is independently selected from the group consisting of halogen, cyano, $C_1$-$C_3$-alkyl, $C_1$-$C_3$-haloalkyl, $C_1$-$C_3$-alkoxy and $C_1$-$C_3$-haloalkoxy;

$X^1$ is $NR^a$ or O;

$X^2$ is $NR^b$, O or S;

Y represents an oxygen atom or two hydrogen atoms;

$R^a$, $R^b$, $R^c$ are each independently selected from the group consisting of hydrogen and $C_1$-$C_4$-alkyl;

a is 0, 1, 2, 3 or 4; and b is 0, 1, 2 or 3;

or a pharmaceutically acceptable salt thereof.

2. The compound or pharmaceutically acceptable salt as claimed in claim 1, wherein $R^1$ is selected from the group consisting of hydrogen and a group —$CH_2R^{1a}$, where $R^{1a}$ is selected from the group consisting of hydrogen, methyl and a 5- to 6-membered monocyclic heteroaromatic ring containing 1 to 3 heteroatoms, independently selected from the group consisting of N, O and S, as ring member, where the 5- to 6-membered monocyclic heteroaromatic ring is unsubstituted or carries 1 radical $R^7$, where $R^7$ is selected from the group consisting of halogen, $C_1$-$C_3$-alkyl and $C_1$-$C_2$-alkoxy.

3. The compound or pharmaceutically acceptable salt as claimed in claim 2, wherein $R^1$ is selected from the group consisting of hydrogen and a group —$CH_2R^{1a}$, where $R^{1a}$ is selected from the group consisting of hydrogen and an unsubstituted 5- to 6-membered monocyclic heteroaromatic ring containing 1 to 3 heteroatoms, independently selected from the group consisting of N, O and S, as ring member.

4. The compound or pharmaceutically acceptable salt as claimed in claim 1, wherein $R^2$ is hydrogen or methyl;

$R^3$ is hydrogen;

$R^4$ is methyl;

each $R^5$ is independently selected from the group consisting of halogen, $C_1$-$C_3$-alkyl and $C_1$-$C_2$-alkoxy;

each $R^6$ is independently selected from the group consisting of halogen, $C_1$-$C_3$-alkyl and $C_1$-$C_2$-alkoxy;

$X^1$ is NH or O;

$X^2$ is O;

a is 0, 1 or 2; and b is 0 or 1.

5. The compound or pharmaceutically acceptable salt as claimed in claim 1, wherein $R^1$ is selected from the group $CH_2$-I' or $CH_2$-II'

($CH_2$-I')

($CH_2$-II')

wherein * indicates the point of attachment to the urea nitrogen atom;

each R⁷ is independently selected from the group consisting of halogen, cyano, $C_1$-$C_3$-alkyl, $C_1$-$C_3$-haloalkyl, $C_1$-$C_3$-alkoxy and $C_1$-$C_3$-haloalkoxy;
$X^3$ is $NR^c$, O or S;
R is selected from the group consisting of hydrogen and $C_1$-$C_4$-alkyl; and
c is 0, 1, 2 or 3.

6. The compound or pharmaceutically acceptable salt as claimed in claim 5, wherein
$R^2$ is hydrogen or methyl;
$R^3$ is hydrogen;
$R^4$ is methyl;
each $R^5$ is independently selected from the group consisting of halogen, $C_1$-$C_3$-alkyl and $C_1$-$C_2$-alkoxy;
each $R^6$ is independently selected from the group consisting of halogen, $C_1$-$C_3$-alkyl and $C_1$-$C_2$-alkoxy;
each $R^7$ is independently selected from the group consisting of halogen, $C_1$-$C_3$-alkyl and $C_1$-$C_2$-alkoxy;
$X^1$ is NH or O;
$X^2$ is O;
$X^3$ is O or S;
a is 0, 1 or 2;
b is 0 or 1; and
c is 0 or 1.

7. The compound or pharmaceutically acceptable salt as claimed in claim 6, wherein
$R^2$ is hydrogen;
$R^3$ is hydrogen;
$R^4$ is methyl;
$X^1$ is NH or O;
$X^2$ is O;
$X^3$ is O or S;
a is 0;
b is 0; and
c is 0.

8. The compound or pharmaceutically acceptable salt of formula I as defined in claim 1, which corresponds to the formula I-A,

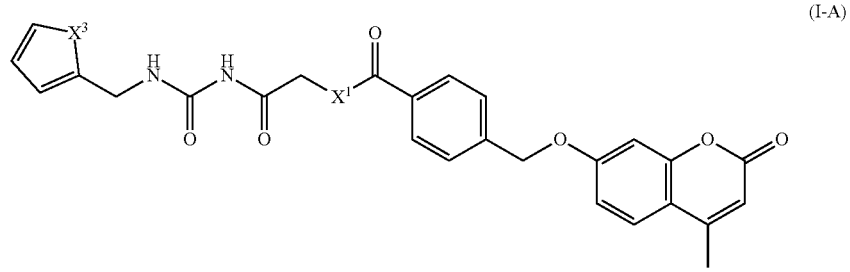

(I-A)

wherein
$X^1$ is NH or O; and
$X^3$ is O or S;
or a pharmaceutically acceptable salt thereof,
or to the formula I-B,

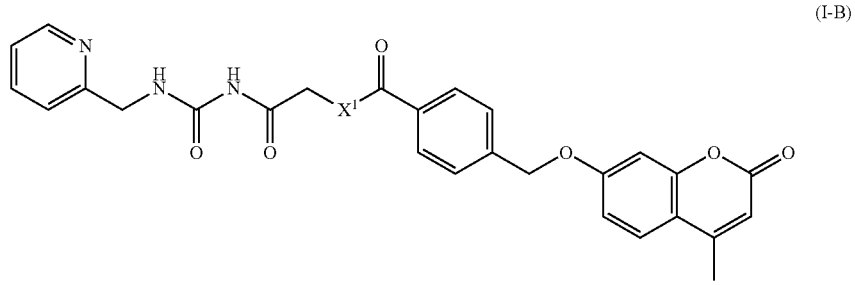

(I-B)

wherein
$X^1$ is NH or O;
or a pharmaceutically acceptable salt thereof,
or to the formula I-C,

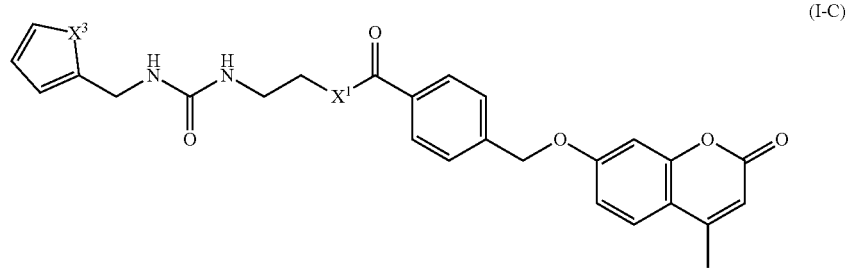

(I-C)

wherein

X¹ is NH or O; and

X³ is O or S;

or a pharmaceutically acceptable salt thereof, or to the formula I-D,

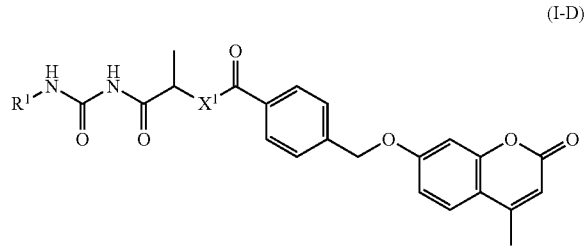

(I-D)

wherein

R¹ is hydrogen or methyl; and

X¹ is NH or O;

or a pharmaceutically acceptable salt thereof.

9. The compound or pharmaceutically acceptable salt of formula I as defined in claim 1, which is [2-(2-furylmethylcarbamoylamino)-2-oxo-ethyl] 4-[(4-methyl-2-oxo-chromen-7-yl)oxymethyl]benzoate or a pharmaceutically acceptable salt thereof.

10. The compound or pharmaceutically acceptable salt of formula I as defined in claim 1, which is 4-[(4-methyl-2-oxo-chromen-7-yl)oxymethyl]-N-[2-(2-thienylmethylcarbamoylamino)ethyl]benzamide or a pharmaceutically acceptable salt thereof.

11. The compound or pharmaceutically acceptable salt of formula I as defined in claim 1, which is [2-oxo-2-(2-pyridylmethylcarbamoylamino) ethyl] 4-[(4-methyl-2-oxo-chromen-7-yl)oxymethyl]benzoate or a pharmaceutically acceptable salt thereof.

12. The compound of formula I as defined in claim 1, which is N-[2-(2-furylmethylcarbamoylamino)-2-oxo-ethyl]-4-[(4-methyl-2-oxo-chromen-7-yl)oxymethyl]benzamide, [2-oxo-2-(2-thienylmethylcarbamoylamino)ethyl] 4-[(4-methyl-2-oxo-chromen-7-yl)oxymethyl]-benzoate, or 4-[(4-methyl-2-oxo-chromen-7-yl)oxymethyl]-N-[2-oxo-2-(2-thienylmethylcarbamoylamino)ethyl]-benzamide, or a pharmaceutically acceptable salt thereof.

13. The compound of formula I as defined in claim 1, which is (1-methyl-2-oxo-2-ureido-ethyl) 4-[(4-methyl-2-oxo-chromen-7-yl)oxymethyl]benzoate or [1-methyl-2-(methylcarbamoylamino)-2-oxo-ethyl] 4-[(4-methyl-2-oxo-chromen-7-yl)oxymethyl]benzoate, or a pharmaceutically acceptable salt thereof.

14. A pharmaceutical composition comprising a compound of formula I as defined in claim 1 or a pharmaceutically acceptable salt thereof and at least one pharmaceutically acceptable carrier.

15. A method for treating or preventing muscle wasting conditions in a subject in need thereof, comprising administering a therapeutically effective amount of a compound of formula I, as defined in claim 1, or a pharmaceutically acceptable salt thereof to the subject in need thereof.

16. A method for treating or preventing skeletal or cardiac muscle atrophy resulting from one of the following diseases or conditions: congestive heart failure, chronic heart failure, cancer, cancer treatment with myotoxic and/or cardiotoxic substances, congenital myopathy, AIDS, chronic obstructive pulmonary disease (COPD), chronic renal diseases, renal failure, diabetes, severe burns, sarcopenia during aging, reduction in blood supply, temporary or long term immobilization, long term mechanical ventilation, denervation, prolonged weightlessness and malnutrition in a subject in need thereof, comprising administering a therapeutically effective amount of a compound of formula I, as defined in claim 1, or a pharmaceutically acceptable salt thereof to the subject in need thereof.

17. A method for treating or preventing conditions which are associated with an increased Muscle RING Finger 1 (MuRF1) expression in a subject in need thereof, comprising administering a therapeutically effective amount of a compound of formula I, as defined in claim 1, or a pharmaceutically acceptable salt thereof to the subject in need thereof.

18. A method for treating or preventing cardiac conditions associated with systolic or diastolic dysfunction in a subject in need thereof, comprising administering a therapeutically effective amount of a compound of formula I, as defined in claim 1, or a pharmaceutically acceptable salt thereof to the subject in need thereof.

19. A method for treating or preventing diabetes in a subject in need thereof, comprising administering a therapeutically effective amount of a compound of formula I, as defined in claim 1, or a pharmaceutically acceptable salt thereof to the subject in need thereof.

20. A method for treating or preventing skeletal or cardiac muscle atrophy resulting from or associated with heart failure with reduced ejection fraction (HF-rEF), heart failure with preserved ejection fraction (HF-pEF), hypertension or tumor cachexia;

muscle atrophy and/or cardiac toxicity induced by Doxorubicin;

sarcopenia and/or cardiomyopathy due to aging;

muscle atrophy due to chronic renal disease;

diaphragm weakness due to mechanical ventilation or congestive heart failure;

congenital myopathy;

diabetes-induced muscle atrophy; and/or diabetes in a subject in need thereof, comprising administering a therapeutically effective amount of a compound of formula I, as defined in claim 1, or a pharmaceutically acceptable salt thereof to the subject in need thereof.

21. The method of claim 17, wherein the condition which is associated with an increased Muscle RING Finger 1 (MuRF1) expression, is a myopathy which is associated with an increased Muscle RING Finger 1 (MuRF1) expression.

22. The method of claim 21, where the myopathy is selected from critical illness myopathy, nemaline myopathy, inflammatory myopathy, myopathy from diabetes, myopathy from pulmonary hypertension, myopathy from chronic heart failure, myopathy from kidney failure and myopathy from tumor cachexia.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: PCR Primer

<400> SEQUENCE: 1
ctcatggact gattatggac aggac                                        25

<210> SEQ ID NO 2
<211> LENGTH: 25
<212> TYPE: DNA
<213> ORGANISM: Artificial Sequence
<220> FEATURE:
<223> OTHER INFORMATION: PCR Primer

<400> SEQUENCE: 2
gcaggtcagc aaagaactta tagcc                                        25

<210> SEQ ID NO 3
<211> LENGTH: 19
<212> TYPE: DNA
<213> ORGANISM: Artificial Sequence
<220> FEATURE:
<223> OTHER INFORMATION: PCR Primer

<400> SEQUENCE: 3
gatgtgcaag gaacacgaa                                               19

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
ccttcacctg gtggctattc                                              20

<210> SEQ ID NO 5
<211> LENGTH: 26
<212> TYPE: DNA
<213> ORGANISM: Artificial Sequence
<220> FEATURE:
<223> OTHER INFORMATION: PCR Primer
```

```
<400> SEQUENCE: 5
gcacaaggag caagtaggca cctcac                                    26

<210> SEQ ID NO 6
<211> LENGTH: 22
<212> TYPE: DNA
<213> ORGANISM: Artificial Sequence
<220> FEATURE:
<223> OTHER INFORMATION: PCR Primer

<400> SEQUENCE: 6
gcctggtgag ccccaaacac ct                                        22
```